United States Patent
Regev et al.

(10) Patent No.: US 11,197,467 B2
(45) Date of Patent: Dec. 14, 2021

(54) DELIVERY, USE AND THERAPEUTIC APPLICATIONS OF THE CRISPR-CAS SYSTEMS AND COMPOSITIONS FOR MODELING MUTATIONS IN LEUKOCYTES

(71) Applicants: The Broad Institute, Inc., Cambridge, MA (US); Massachusetts Institute of Technology, Cambridge, MA (US); The General Hospital Corporation, Boston, MA (US)

(72) Inventors: Aviv Regev, Cambridge, MA (US); Oren Parnas, Jerusalem (IL); Marko Jovanovic, Boston, MA (US); Nir Hacohen, Brookline, MA (US); Thomas Eisenhaure, North Reading, MA (US)

(73) Assignees: The Broad Institute, Inc., Cambridge, MA (US); Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/468,652

(22) Filed: Mar. 24, 2017

(65) Prior Publication Data
US 2018/0255751 A1   Sep. 13, 2018

Related U.S. Application Data

(63) Continuation-in-part of application No. PCT/US2015/051815, filed on Sep. 24, 2015.

(60) Provisional application No. 62/180,759, filed on Jun. 17, 2015, provisional application No. 62/054,501, filed on Sep. 24, 2014.

(51) Int. Cl.
| | | |
|---|---|---|
| A01K 67/027 | (2006.01) |
| C12N 15/63 | (2006.01) |
| C12N 15/79 | (2006.01) |
| C07H 21/02 | (2006.01) |
| C12N 15/113 | (2010.01) |
| C12N 15/11 | (2006.01) |
| A61K 48/00 | (2006.01) |
| C12N 7/04 | (2006.01) |
| C12N 9/22 | (2006.01) |
| C12N 15/10 | (2006.01) |

(Continued)

(52) U.S. Cl.
CPC ...... *A01K 67/0271* (2013.01); *A01K 67/0275* (2013.01); *A61K 48/005* (2013.01); *C12N 7/04* (2013.01); *C12N 9/22* (2013.01); *C12N 15/1082* (2013.01); *C12N 15/111* (2013.01); *C12N 15/113* (2013.01); *C12N 15/85* (2013.01); *C12N 15/907* (2013.01); *A01K 2207/05* (2013.01); *A01K 2207/12* (2013.01); *A01K 2217/052* (2013.01); *A01K 2217/077* (2013.01); *A01K 2227/105* (2013.01); *A01K 2267/0312* (2013.01); *A01K 2267/0331* (2013.01); *A01K 2267/0362* (2013.01); *C07K 2319/09* (2013.01); *C12N 2310/10* (2013.01); *C12N 2310/20* (2017.05); *C12N 2310/3513* (2013.01); *C12N 2310/531* (2013.01); *C12N 2320/12* (2013.01); *C12N 2330/31* (2013.01); *C12N 2330/51* (2013.01); *C12N 2740/15043* (2013.01); *C12N 2750/14143* (2013.01)

(58) Field of Classification Search
CPC ............ A01K 67/0275; A01K 67/0278; C12N 15/63; C12N 15/85; C12N 2310/20; C07H 21/02
See application file for complete search history.

(56) References Cited

U.S. PATENT DOCUMENTS

| 4,186,183 A | 1/1980 | Alving et al. |
| 4,217,344 A | 8/1980 | Handjani et al. |

(Continued)

FOREIGN PATENT DOCUMENTS

| EP | 0264166 A1 | 4/1988 |
| EP | 2764103 A2 | 8/2014 |

(Continued)

OTHER PUBLICATIONS

Kotterman et al., 2014, Nature Reviews, vol. 15, p. 445-451.*

(Continued)

*Primary Examiner* — Shin Lin Chen
(74) *Attorney, Agent, or Firm* — Johnson, Marcou, Isaacs & Nix, LLC; F. Brent Nix, Esq.; Michael B. Scher, Esq

(57) ABSTRACT

The invention involves a method for modulating leukocyte activity, comprising delivering to a leukocyte a vector containing nucleic acid molecule(s), whereby the leukocyte contains Cas9 and the vector expresses one or more RNAs to guide the Cas9 to introduce mutations in one or more target genetic loci in the leukocyte, thereby modulating expression of one or more genes expressed in the leukocyte. The invention also involves identifying genes associated with leukocyte responses and experimental modeling of aberrant leukocyte activation and diseases associated with leukocytes by introducing mutations into leukocytes. The invention comprehends testing putative treatments with such models, e.g., testing putative chemical compounds that may be pharmaceutically relevant for treatment or gene therapy that may be relevant for treatment, or combinations thereof. The invention allows for the study of genetic diseases and putative treatments to better understand and alleviate leukocyte associated diseases.

6 Claims, 44 Drawing Sheets

Specification includes a Sequence Listing.

(51) Int. Cl.
  *C12N 15/85* (2006.01)
  *C12N 15/90* (2006.01)

(56) References Cited

U.S. PATENT DOCUMENTS

| | | | |
|---|---|---|---|
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,797,368 | A | 1/1989 | Carter et al. |
| 4,837,028 | A | 6/1989 | Allen |
| 4,873,316 | A | 10/1989 | Meade et al. |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |
| 5,846,946 | A | 12/1998 | Huebner et al. |
| 6,750,059 | B1 | 6/2004 | Blakesley et al. |
| 7,776,321 | B2 | 8/2010 | Cascalho et al. |
| 8,404,658 | B2 | 3/2013 | Hajjar et al. |
| 8,454,972 | B2 | 6/2013 | Nabel et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 2004/0171156 | A1 | 9/2004 | Hartley et al. |
| 2011/0027239 | A1 | 2/2011 | Paek |
| 2011/0059502 | A1 | 3/2011 | Chalasani |
| 2011/0265198 | A1 | 10/2011 | Gregory et al. |
| 2012/0003201 | A1 | 1/2012 | Nicholas et al. |
| 2012/0017290 | A1 | 1/2012 | Cui et al. |
| 2013/0236946 | A1 | 9/2013 | Gouble |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |
| 2014/0287938 | A1 | 9/2014 | Zhang et al. |
| 2014/0310830 | A1 | 10/2014 | Zhang et al. |
| 2018/0255751 | A1 | 9/2018 | Regev et al. |

FOREIGN PATENT DOCUMENTS

| | | | |
|---|---|---|---|
| EP | 2771468 | B1 | 2/2015 |
| EP | 2784162 | B1 | 4/2015 |
| WO | 9116024 | A1 | 10/1991 |
| WO | 9117424 | A1 | 11/1991 |
| WO | 9324641 | A2 | 12/1993 |
| WO | 9639154 | A1 | 12/1996 |
| WO | 9703211 | A1 | 1/1997 |
| WO | 2011028929 | A3 | 3/2011 |
| WO | 2013138585 | A1 | 9/2013 |
| WO | 2014018423 | A2 | 1/2014 |
| WO | 2014093595 | A1 | 6/2014 |
| WO | 2014093622 | A2 | 6/2014 |
| WO | 2014093635 | A1 | 6/2014 |
| WO | 2014093655 | A2 | 6/2014 |
| WO | 2014093661 | A2 | 6/2014 |
| WO | 2014093694 | A1 | 6/2014 |
| WO | 2014093701 | A1 | 6/2014 |
| WO | 2014093709 | A1 | 6/2014 |
| WO | 2014093712 | A1 | 6/2014 |
| WO | 2014093718 | A1 | 6/2014 |
| WO | 2014204723 | | 12/2014 |
| WO | 2014204724 | A1 | 12/2014 |
| WO | 2014204725 | A1 | 12/2014 |
| WO | 2014204726 | A1 | 12/2014 |
| WO | 2014204727 | A1 | 12/2014 |
| WO | 2014204728 | A1 | 12/2014 |
| WO | 2014204729 | A1 | 12/2014 |
| WO | 2016049251 | A1 | 3/2016 |

OTHER PUBLICATIONS

Kaur et al., 2009, Current Gene Therapy, vol. 9. p. 434-458.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Yang et al., 2016, PNAS, 113(41), E6209-E6218, p. 1-10.*
Guo et al., 2015, Cell Research, vol. 25, p. 767-768.*
Lee et al., 2016, Drug Discovery Today: Disease Models, vol. 20, p. 13-20.*
International Search Report dated Dec. 12, 2015, which issued during prosecution of International Application No. PCT/US2015/051815.
Chen, et al., "Genome-wide CRISPR Screen in a Mouse Model of Tumor Growth and Metastasis", Cell, 2015, 160:1246-1260.
Hiroko Koike-Yusa, et al. "Genome-wide recessive genetic screening in mammalian cells with a lentiviral CRISPR-guide RNA library", Nature Biotechnology, 2014, 32:267-273.
Pankaj, et al., "Efficient Ablation of Genes in Human Hematopoietic Stem and Effector Cells using CRISPR/Cas9", Cell Stem Cell, 2014, 15:643-652.
Parnas, et al., "A Genome-wide CRISPR Screen in Primary Immune Cells to Dissect Regulatory Networks", Cell, 2015, 162:675-686.
Platt, et al., "CRISPR-Cas9 Knocking Mice for Genome Editing and Cancer Modeling", Cell, 2014, 159:440-455.
Shalem, et al., "Genome-Scale CRISPR-Cas9 Knockout Screening in Human Cells", Science, 2014, 343:84-87.
Wang, et al., "Genetic Screens in Human Cells Using the CRISPR-Cas9 System", Science, 2014, 343:80-84.
Yuexin Zhou, et al., "High-throughput screening of a CRISPR/Cas9 library for functional genomics in human cells", Nature, 2014, 509:487-491.
Amit, et al., "Strategies to Discover Regulatory Circuits of the Mammalian Immune System", Nature Reviews, Immunology, vol. 11, No. 12, Nov. 18, 2011, 873-880.
Amit, et al., "Unbiased Reconstruction of a Mammalian Transcriptional Network Mediating the Differential Response to Pathogens", Science, vol. 326, No. 5950, Oct. 9, 2009, 257-263.
Bell, et al., "The AAV9 Receptor and its Modification to Improve in Vivo Lung Gene Transfer in Mice", The Journal of Clinical Investigation, vol. 121, No. 6, Jun. 2011, 2427-2435.
Chevrier, et al., "Systematic Discovery of TLR Signaling Components Delineates Viral-Sensing Circuits", Cell, vol. 147, No. 4, Nov. 11, 2011, 853-867.
Cong, et al., "Multiplex Genome Engineering Using CRISPR/Cas Systems", Science, vol. 339, No. 6121, Feb. 14, 2013, 819-823.

(56) References Cited

OTHER PUBLICATIONS

Garber, et al., "A High Throughput Chromatin Immunoprecipitation Approach Reveals Principles of Dynamic Gene Regulation in Mammals", Molecular Cell, vol. 47, No. 5, Sep. 14, 2012, 810-822.
Klein, et al., "Droplet Barcoding for Single-Cell Transcriptomics Applied to Embryonic Stem Cells", Cell, vol. 161, No. 5, May 21, 2015, 1187-1201.
Konermann, et al., "Genome-Scale Transcriptional Activation by an Engineered CRISPR-Cas9 Complex", Nature, vol. 517, No. 7536, Dec. 10, 2014, 583-588.
Macosko, et al., "Highly Parallel Genome-Wide Expression Profiling of Individual Cells Using Nanoliter Droplets", Cell, Voume 161, No. 5, May 21, 2015, 1202-1214.
Mali, et al., "RNA-Guided Human Genome Engineering via Cas9", Science, vol. 339, No. 6121, Feb. 15, 2013, 823-826.
Mandal, et al., "Efficient Ablation of Genes in Human Hematopoietic Stem and Effector Cells Using CRISPR/Cas9", Cell Stem Cell, vol. 15, No. 5, Nov. 2014, 643-652.
Sanjana, et al., "Improved Vectors and Genome-Wide Libraries for CRISPR Screening", Nature Methods, vol. 11, No. 8, Aug. 2014, 783-784.
Shalek, et al., "Single-cell transcriptomics reveals bimodality in expression and splicing in immune cells", Nature, 498, 2013, pp. 236-240.
Swiech, et al., "In Vivo Interrogation of Gene Function in the Mammalian Brain using CRISPR-Cas9", Nature Biotechnology, vol. 33, No. 1, Oct. 19, 2014, 102-106.
The Broad Institute, Inc., et al., "International Preliminary Report on Patentability and Written Opinion issued in International Application No. PCT/US2015/051815", dated Mar. 28, 2017, 7 pages.
Wang, et al., "One-Step Generation of Mice Carrying Mutations in Multiple Genes by CRISPR/Cas-Mediated Genome Engineering", Cell, vol. 153, No. 4, May 9, 2013, 910-918.
Xue, et al., "CRISPR-Mediated Direct Mutation of Cancer Genes in the Mouse Liver", Nature, vol. 514, No. 7522, Oct. 16, 2014, 380-384.

Kim et al., "Transcriptional Regulatory Circuits: Predicting Numbers from Alphabets," Science, Jul. 24, 2009; 325(5939), pp. 429-432.
Parnas et al., "A Genome-wide CRISPR Screen in Primary Immune Cells to Dissect Regulatory Networks," Cell, 2015, 162(3), pp. 675-686.
Chou et al., "Generation and Characterization of a Transgenic Pig Carrying a DsRed-Monomer Reporter Gene," PLos One, vol. 9, Issue 9, e106864, 10 pages, Sep. 2014.
Li et al., "Efficient Production of Fluorescent Transgenic Rats using the piggyBac Transposon," Scientific Reports, 8 pages, 2016.
Liu et al., "Highly Efficient Generation of Transgenic Sheep by Lentivirus Accompanying the Alteration of Methylation Status," PLos One, vol. 8, Issue 1, e54614, 9 pages, Jan. 2013.
Peng, "Transgenic Rabbit Models for Studying Human Cardiovascular Diseases," Comparative Medicine, vol. 62, No. 6, pp. 472-479, Dec. 2012.
Tomita et al., "Visual Properties of Transgenic Rats Harboring the Channelrhodopsin-2 Gene Regulated by the Thy-1.2 Promoter," PLos One, vol. 4, issue 11, e7679, 13 pages, Nov. 2009.
Wherry et al., "Molecular Signature of CD8+ T Cell Exhaustion during Chronic Viral Infection," Immunity, 27, pp. 670-684, Oct. 2007.
Yang et al., "Towards a transgenic model of Huntington's disease in a nonhuman primate," Nature, 453(7197), pp. 921-924, Jun. 2008.
Cortez et al., "CRISPR Screen in Regulatory T Cells Reveals Modulators of Foxp3", Nature, 582(7812), pp. 416-420, Jun. 2020.
Loo et al., A Genome-wide CRISPR Screen Reveals a Role for the Non-canonical Nucleosome-Remodeling BAF Complex in Foxp3 Expression and Regulatory T Cell Function, Immunity, 53, pp. 143-157, Jul. 14, 2020.
Chu, et al., "Efficient CRISPR-mediated mutagenesis in primary immune cells using CrispRGold and a C57BL/6 Cas9 transgenic mouse line", Proc Natl Acad Sci USA. 2016;113(44):12514-12519.

* cited by examiner

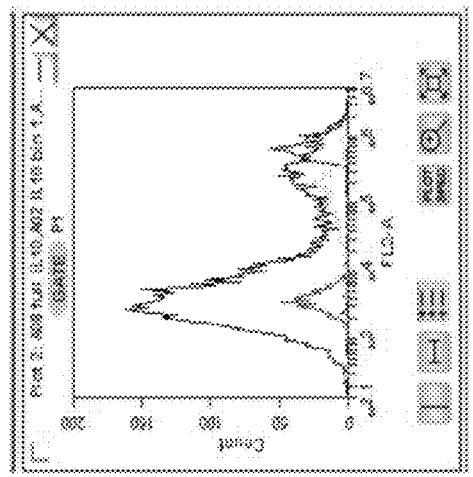
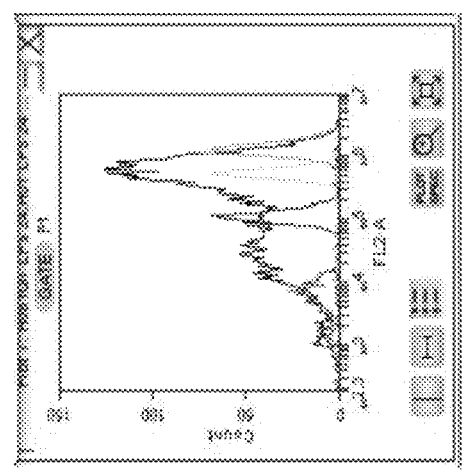
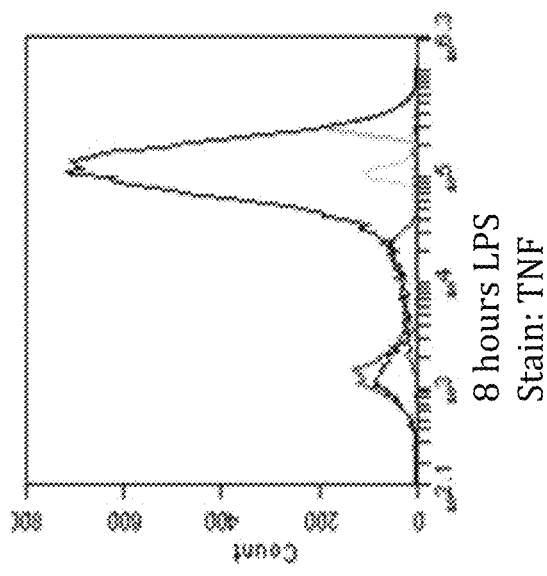
FIG. 12

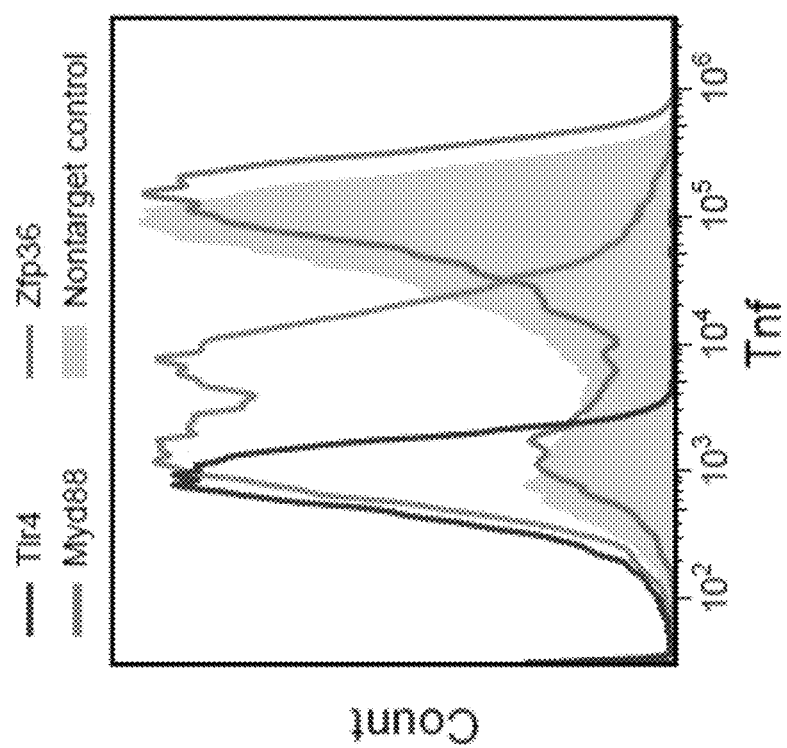

FIG. 19A
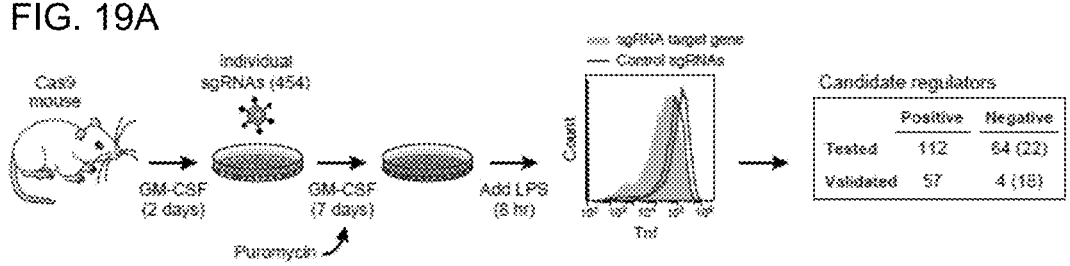
FIG. 19B
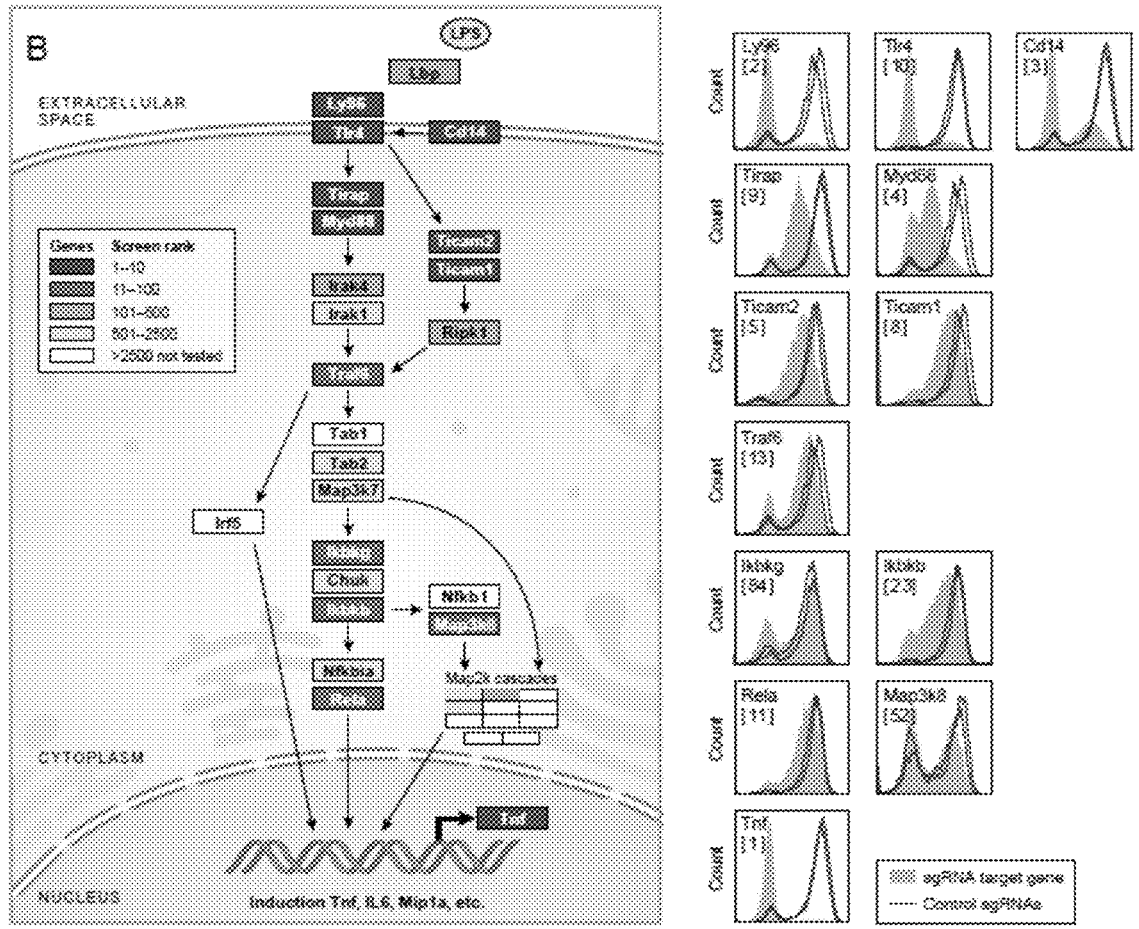
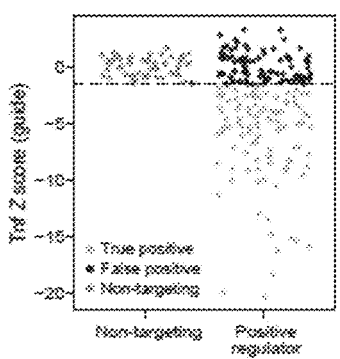
FIG. 19C
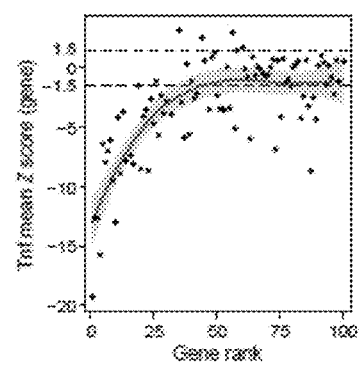
FIG. 19D
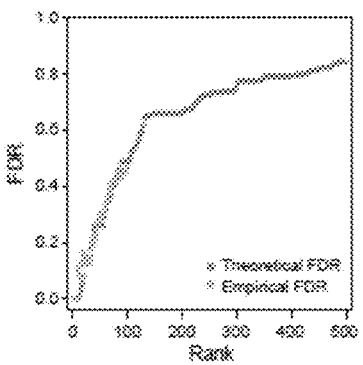
FIG. 19E

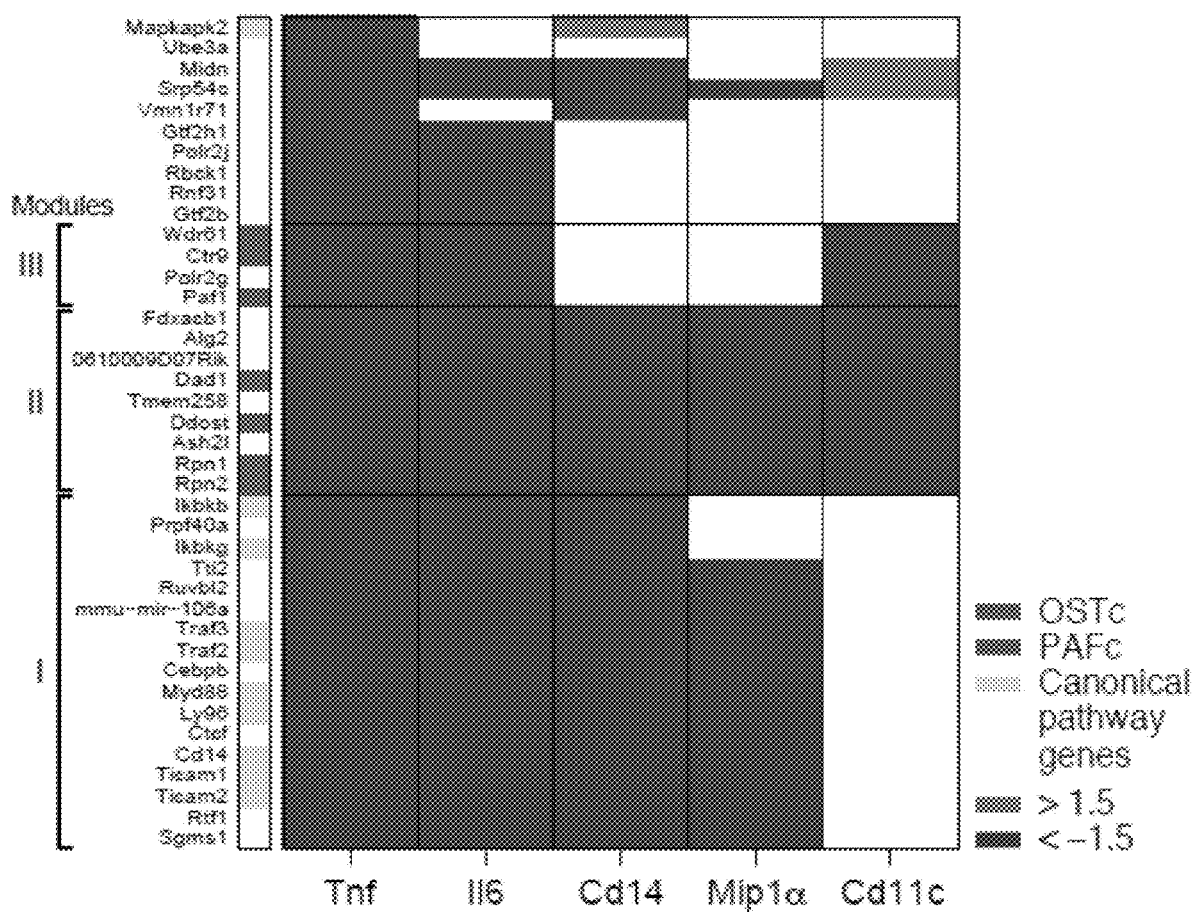

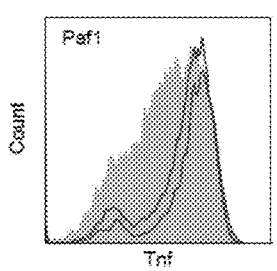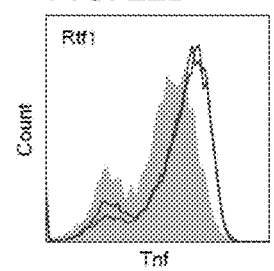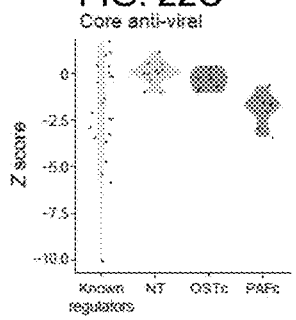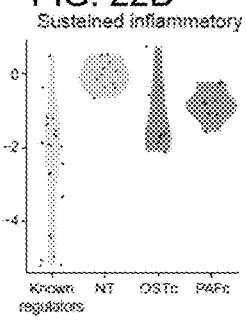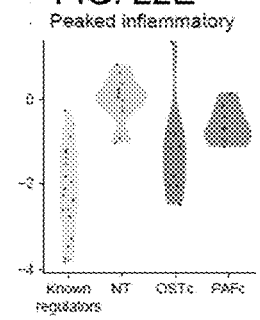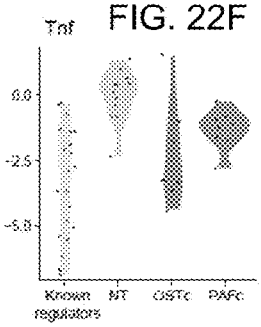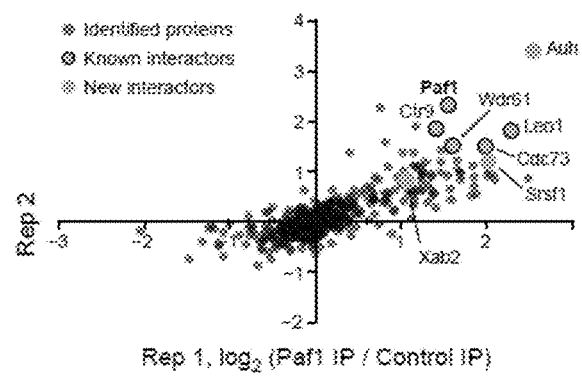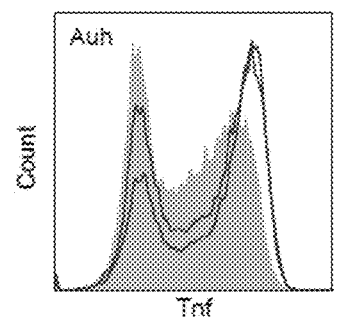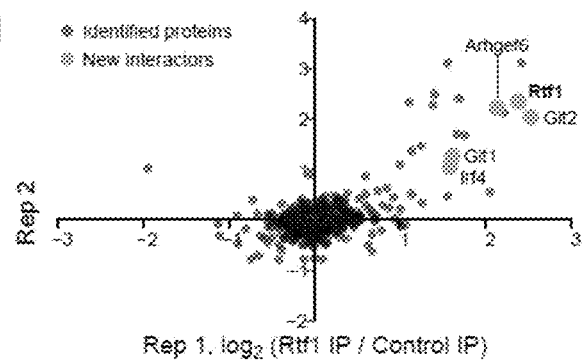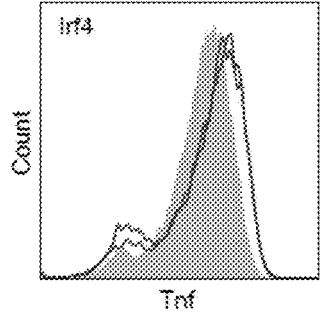

FIG. 27A
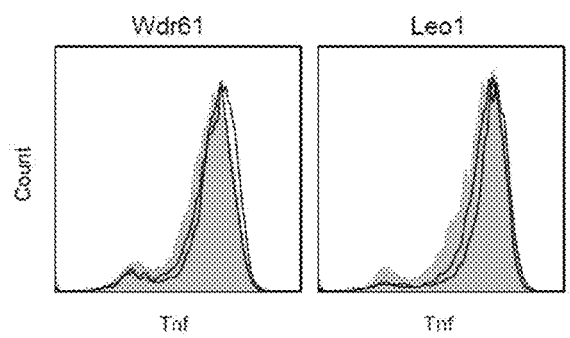
FIG. 27B
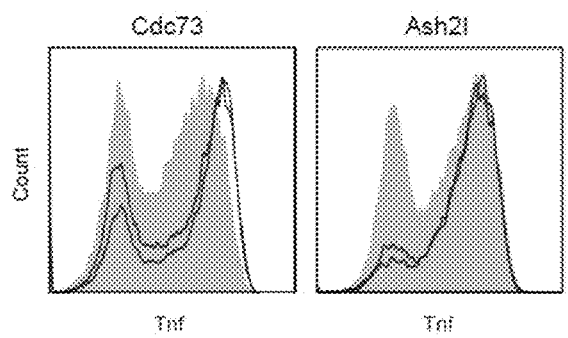
FIG. 27C
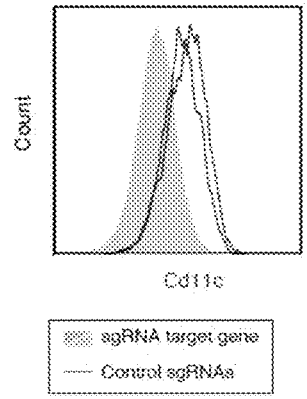
FIG. 27D
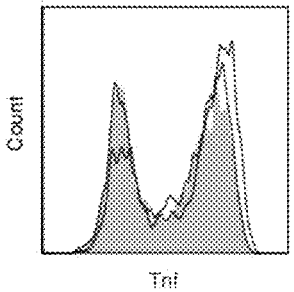
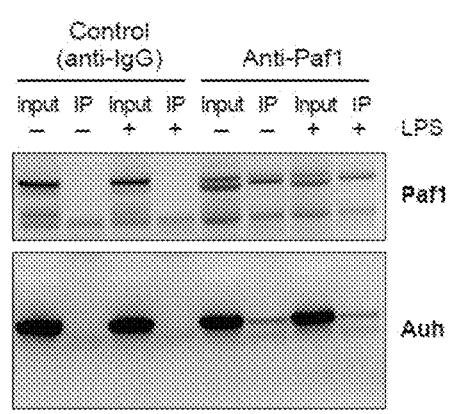
FIG. 27E

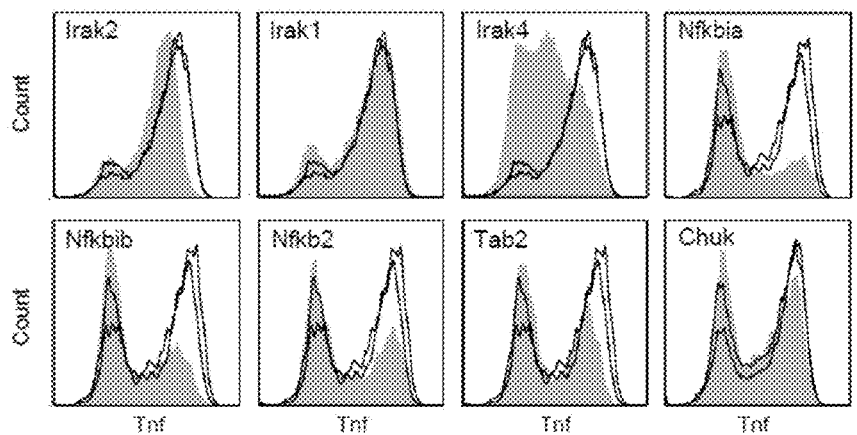
FIG. 28A
FIG. 28B
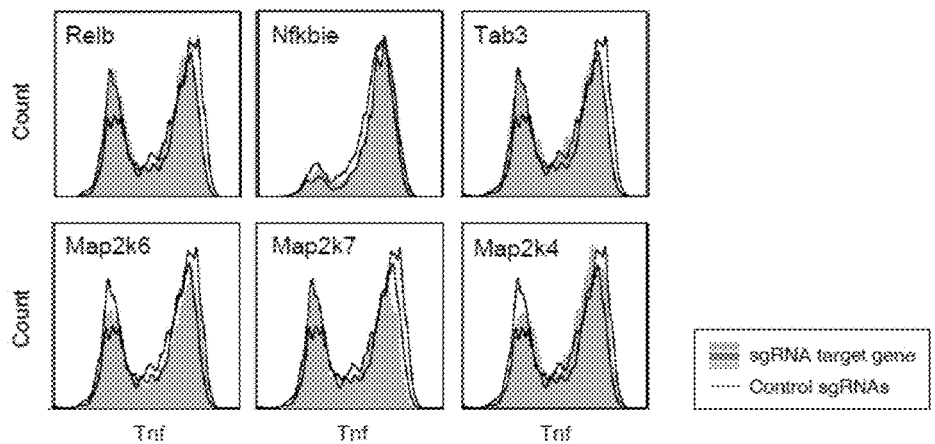
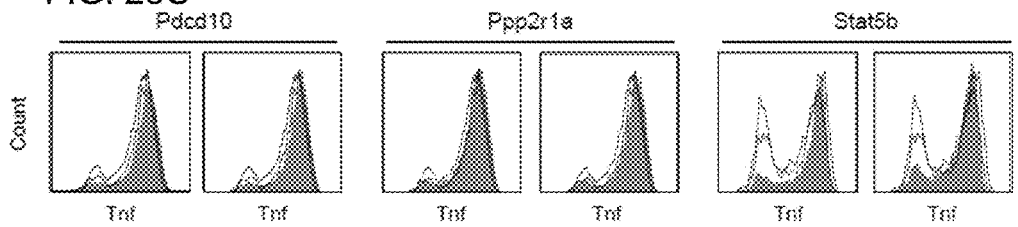
FIG. 28C
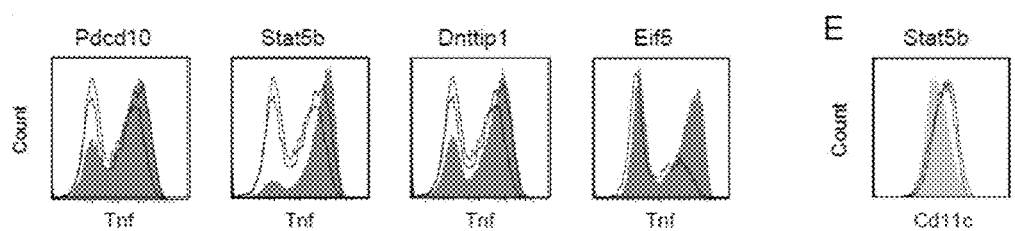
FIG. 28D
FIG. 28E

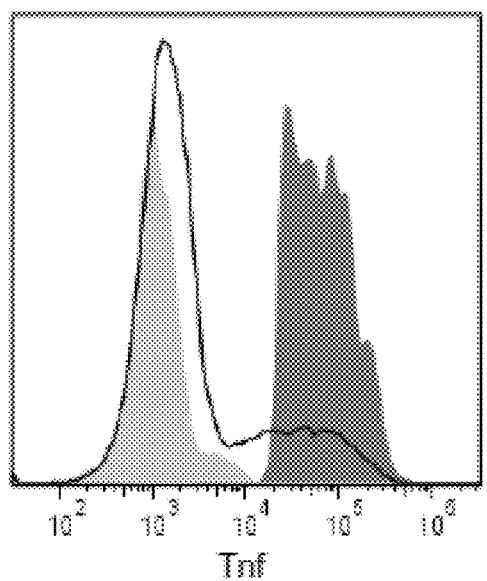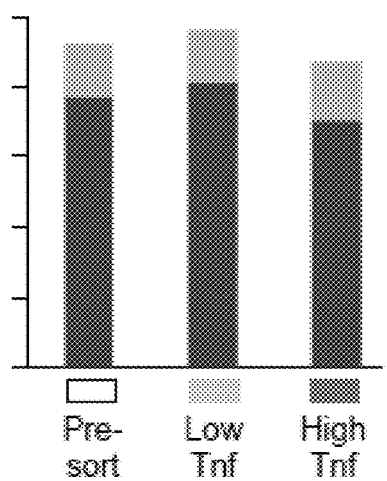
FIG. 30C

DELIVERY, USE AND THERAPEUTIC APPLICATIONS OF THE CRISPR-CAS SYSTEMS AND COMPOSITIONS FOR MODELING MUTATIONS IN LEUKOCYTES

RELATED APPLICATIONS AND/OR INCORPORATION BY REFERENCE

This application is a Continuation-In-Part of International Application Number PCT/US2015/51815 filed on Sep. 24, 2015, which published as WO2016/049251 on Mar. 31, 2016 and claims benefit of and priority to U.S. provisional patent application Ser. No. 62/054,501, filed Sep. 24, 2014, and U.S. provisional patent application Ser. No. 62/180,759 filed Jun. 17, 2015.

Reference is also made to U.S. provisional patent applications 61/770,036, filed Feb. 27, 2013; 61/787,378, filed Mar. 15, 2013, 62/094,859, filed Dec. 19, 2014, and 62/176,796 filed Feb. 26, 2015 incorporated herein by reference.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant number HG006193 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created Mar. 23, 2017 is named 48009992079 SL.txt and is 8.516 bytes in size.

FIELD OF THE INVENTION

The present invention generally relates to the Clustered Regularly Interspaced Short Palindromic Repeats (CRISPR)-Cas System and components thereof. More specifically, the present invention relates to modulating leukocyte activity, identifying genes or genomic elements associated with leukocyte responses, and modeling aberrant leukocyte responses and diseases associated with leukocytes by introducing mutations into the genome of leukocytes ex vivo and/or in vivo using a transgenic CRISPR-Cas9 animal (e.g., mouse) model, including the model(s) and methods for generation and uses thereof.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual DNA and/or RNA elements and their combinations, as well as to advance synthetic biology, biotechnological, and medical applications.

A major challenge facing the continued study of genetics is distinguishing which mutations are drivers from those that are not ("passengers") (Garraway and Lander, 2013; Lawrence et al. 2013). The difficulty of elucidating these distinctions in animal models lies in precisely generating such mutation(s) and measuring the influence of specific mutations throughout the subject's condition. These challenges apply to other areas of genetic and tissue-specific biological studies as well.

Citation or identification of any document in this application is not an admission that such document is available as prior art to the present invention.

SUMMARY OF THE INVENTION

While observational strategies have become a cornerstone of circuit inference from genomic data, perturbational strategies have been more challenging to apply on a genomic scale, especially in primary mammalian cells. RNAi, which until recently was the main available tool in mammals, is limited by off-target effects and lack of sufficient suppression of gene expression (Echeverri et al., 2006), whereas more effective strategies based on haploid cell lines (Carette et al., 2009) are not applicable to the diversity of primary cell types and their specialized circuitry. As a result, a hybrid approach has emerged (Amit et al., 2011) where genomic profiles (e.g., of mRNAs, protein-DNA binding, protein levels, protein phosphorylation, etc.) are used to build observational models from which a smaller set of dozens of candidate regulators are identified. These candidates are in turn tested by perturbation.

The recent introduction of genome editing in mammalian cells using the clustered, regularly interspaced, short palindromic repeats CRISPR-associated nuclease Cas9 system opens new possibilities for pooled genome-wide screens of gene function (Shalem et al., 2014; Wang et al., 2014), but substantial challenges remain in adapting it for dissecting gene regulation in primary cells.

In one aspect, the invention adapts CRISPR-Cas9 technology to develop a marker based genome-wide knockout screen in primary mammalian cells derived from Cas9-expressing transgenic mice, and apply it to dissect gene regulatory circuits in the response of dendritic cells ("DCs") to lipopolysaccharide ("LPS.")

There exists a pressing need for alternative and robust systems and techniques for modulating leukocyte activity, as well as for identifying genes or genomic elements associated with leukocyte responses and for experimental modeling of aberrant leukocyte activation and diseases associated with leukocytes. Such processes may be achieved by introducing mutations into leukocytes, especially multiple mutations, to enable the study of the effects of specific, multiple mutagenic events. Mutagenic events can include knock out events. Aspects of this invention may address this need and provide related advantages. Aspects of the present invention may address herein discussed challenges and need in the art by advantageously providing methods, systems, compositions and models for ex vivo and in vivo modeling of processes involving leukocytes, by introducing mutations into leukocytes, including in specific subsets thereof, for instance in order to modulate leukocyte responses such as e.g. activation or differentiation or to identify genes associated with such responses.

In one aspect the invention provides a method for modulating leukocyte activity, comprising delivering to a leukocyte a vector containing nucleic acid molecule(s), whereby the leukocyte contains Cas9 and the integrated vector expresses one or more RNAs to guide the Cas9 to introduce mutations in one or more target genetic loci in the leukocyte, thereby modulating expression of one or more genes in the leukocyte.

In another aspect the invention provides a method of identifying a gene associated with a leukocyte response, comprising (a) delivering to a plurality of leukocytes a plurality of different vectors containing nucleic acid molecule(s), whereby the leukocytes contain Cas9 and each vector expresses one or more RNAs to guide the Cas9 to introduce mutations in different target genetic loci in the leukocytes, thereby modulating expression of different genes expressed in the leukocytes; (b) measuring a response in the leukocytes; (c) isolating leukocyte(s) in which the response is modulated following delivery of the vector; and (d) thereby identifying gene(s) associated with the leukocyte response.

In a further aspect, the invention provides a method for modeling an aberrant leukocyte response or a disease associated with leukocytes, comprising delivering to leukocytes a vector containing nucleic acid molecule(s), whereby the leukocytes contain Cas9 and the integrated or non-integrated vector expresses one or more RNAs to guide the Cas9 to introduce mutations in one or more target genetic loci in the leukocytes, thereby modulating expression of one or more genes expressed in the leukocytes, and wherein expression of the one or more genes is associated with the response or disease.

In a further aspect, the invention provides an individualized or personalized treatment of a leukocyte-associated disease in a subject in need of such treatment comprising (a) delivering to leukocytes ex vivo a vector containing nucleic acid molecule(s), whereby the leukocytes express Cas9 and the vector expresses one or more RNAs to guide the Cas9 to introduce mutations in one or more target genetic loci in the leukocytes, thereby modulating expression of one or more genes expressed in the leukocytes, and wherein expression of the one or more genes is correlated to the disease; (b) testing treatment(s) for the disease on the leukocytes to which the vector has been delivered that comprise mutations in genes correlated to the disease; and (c) treating the subject based on results from the testing of treatment(s) of step (b).

In a further aspect, the invention provides an isolated leukocyte comprising a vector containing a nucleic acid molecule(s), wherein the leukocyte contains or conditionally or inducibly expresses Cas9 and the vector encodes one or more RNAs capable of guiding the Cas9 to introduce mutations in one or more target genetic loci in the leukocyte, and thereby modulating expression of one or more genes expressed in the leukocyte.

In a further aspect, the invention provides an isolated leukocyte comprising a vector containing a nucleic acid molecule(s), wherein the leukocyte contains or conditionally or inducibly expresses Cas9, one or more target genetic loci in the leukocyte comprise mutations derived from Cas9 activity guided by one or more RNAs encoded by the vector, and the mutations modulate expression of one or more genes expressed in the leukocyte.

Aspects of the invention provide methods for enabling rapid and direct in vivo and ex vivo modeling of the dynamics of leukocyte responses (e.g. activation and differentiation) associated with mutations in leukocytes. Aspects of the present invention involve sequence targeting, such as genome perturbation or induction of multiple mutations using the Clustered Regularly Interspaced Short Palindromic Repeats (CRISPR) system or components thereof. The invention provides systematic reverse engineering of causal genetic variations, including through selective perturbation of individual, and moreover, multiple genetic elements. For instance, in non-human eukaryote, e.g., animal, such as fish, e.g., zebra fish, mammal, e.g., primate, e.g., ape, chimpanzee, macaque, rodent, e.g., mouse, rabbit, rat, canine or dog, livestock (cow/bovine, sheep/ovine, goat or pig), fowl or poultry, e.g., chicken, models that constitutively or through induction or through administration or delivery, have cells that contain Cas9. The invention provides tools for studying genetic interaction between multiple individual genetic elements by allowing selective perturbation of e.g., one or more gene(s)/genetic element(s) in leukocytes or a subset thereof. In an aspect, the invention provides methods for using one or more elements/components of a CRISPR-Cas system via a vector and/or particle and/or nanoparticle delivery formulation or system as a means to modify a target polynucleotide in leukocytes. In preferred embodiments, the delivery is via a viral vector (e.g., AAV, adenovirus, lentivirus, preferably a lentivirus) or a cell-penetrating peptide (CPP) (e.g., a peptide of about 8-13 amino acids, typically about 11 amino acids, having an amino acid composition that either contains a high relative abundance of positively charged amino acids such as lysine or arginine or has sequences that contain an alternating pattern of polar/charged amino acids and non-polar, hydrophobic amino acids—polycationic or amphipathic, respectively). The CRISPR complex of the invention provides an effective means for modifying a target polynucleotide in leukocytes or a subset thereof. The CRISPR complex of the invention has a wide variety of utilities including modifying (e.g., deleting, inserting, translocating, inactivating, activating) a target polynucleotide in leukocytes or a subset thereof, e.g. in dendritic cells, monocytes, macrophages, T cells, B cells, natural killer (NK) T cells, NK cells, neutrophils, eosinophils, basophils, mast cells, innate lymphoid cells, follicular dendritic cells, stellate cells as well as precursors of mature leukocytes such as hematopoietic stem and progenitor cells. As such the CRISPR complex of the invention has a broad spectrum of applications in modeling of effects of mutations in leukocytes, and hence gene therapy, drug discovery, drug screening, disease diagnosis, and prognosis.

It will be appreciated that in the present methods, the modification may occur ex vivo or in vitro in leukocytes derived from a non-human transgenic Cas9 organism, for instance in a cell culture and in some instances not in vivo. In a preferred embodiment, the modification occurs ex vivo in primary cells, e.g. in primary leukocytes extracted from a human or non-human animal or in cells derived from primary leukocytes by differentiation ex vivo. In other embodiments, it may occur in vivo. In some embodiments, leukocytes are modified ex vivo and then reintroduced into a different individual human or non-human animal, e.g. via adoptive transfer. In an aspect, the invention provides a method of modifying an organism or a non-human organism, or leukocytes derived from an organism or non-human organism, by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition into leukocytes of or from the organism.

The composition can comprise: A) I. RNA(s) having polynucleotide sequence(s), e.g., a CRISPR-Cas system chimeric RNA (chiRNA) having a polynucleotide sequence, wherein the polynucleotide sequence comprises: (a) a guide sequence capable of hybridizing to a target sequence in a leukocyte, (b) a tracr mate sequence, and (c) a tracr sequence; wherein (a), (b) and (c) are arranged in a 5' to 3' orientation. The composition can also comprise A) II. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridizable to the target sequence, and (2) the tracr mate sequence that is hybridizable to the tracr sequence. The polynucleotide sequence encoding a CRISPR enzyme is DNA or RNA. When the Cas9 is already present in the leukocyte, e.g., through the leukocyte having already been provided (A) II. or through the leukocyte expressing Cas9, e.g., through the leukocyte having been transformed to express Cas9, e.g., Cas9 is expressed constitutively or conditionally or inducibly—for instance when the leukocyte is part of or from a non-human transgenic eukaryote, e.g., animal, mammal, primate, rodent, etc as herein discussed—then (A) I. is provided as the CRISPR complex is formed in situ or in vivo. In an aspect, the invention provides a method of modifying an organism or a non-human organism, or leukocytes derived from an organism or non-human organism, by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition into leukocytes of or from the organism. The composition can comprise (B) I. polynucleotides comprising: (a) a guide sequence capable of hybridizing to a target sequence in a leukocyte, and (b) at least one or more tracr mate sequences. The composition can also comprise (B) II. a polynucleotide sequence comprising a tracr sequence. The composition can also comprise (B) III. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence. The CRISPR complex comprises the CRISPR enzyme complexed with (1) the guide sequence that is hybridizable to the target sequence, and (2) the tracr mate sequence that is hybridizable to the tracr sequence, and the polynucleotide sequence encoding a CRISPR enzyme is DNA or RNA. When the Cas9 is already present in the leukocyte, e.g., through the leukocyte having already been provided (B) III. or through the leukocyte expressing Cas9, e.g., through the leukocyte having been transformed to express Cas9, e.g., Cas9 is expressed constitutively or conditionally or inducibly—for instance when the leukocyte is part of or from a non-human transgenic eukaryote, e.g., animal, mammal, primate, rodent, etc as herein discussed—then (B) I. and (B) II. are provided as the CRISPR complex is formed in situ or in vivo. Accordingly, components I and II or I, II and III or the foregoing embodiments can be delivered separately; for instance, in embodiments involving components I, II and III, components I and II can be delivered together, while component III can be delivered separately, e.g., prior to components I and II, so that the leukocyte expresses Cas9.

In some embodiments the invention comprehends delivering a CRISPR enzyme comprising delivering to a leukocyte mRNA encoding the CRISPR enzyme, e.g., via nanoparticle complex(es). In some of these methods the CRISPR enzyme is a Cas9. In certain preferred embodiments the Cas9 enzyme is constitutively present, e.g., through knock-in. Thus, in a preferred embodiment of the invention, the Cas9 enzyme is constitutively present in vivo (e.g, a non-human transgenic eukaryote, animal, mammal, primate, rodent, etc) or ex vivo (comprising a vector containing nucleic acid molecule(s) for in vivo expression of the Cas9). The CRISPR enzyme is a type I or III CRISPR enzyme, preferably a type II CRISPR enzyme. This type II CRISPR enzyme may be any Cas enzyme. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, SpCas9 or SaCas9. It will be appreciated that SpCas9 or SaCas9 are those from or derived from *S. pyogenes* or *S. aureus* Cas9. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. The Cas enzyme can be for instance any naturally-occurring bacterial Cas9 as well as any chimaeras, mutants, homologs or orthologs. Many of the residue numberings used herein refer to the Cas9 enzyme from the type II CRISPR locus in *Streptococcus pyogenes* (annotated alternatively as SpCas9 or spCas9). However, it will be appreciated that this invention includes many more Cas9s from other species of microbes, e.g., orthologs of SpCas9, or Cas9s derived from microbes in addition to *S. pyogenes*, e.g., SaCas9 derived from *S. aureus*, St1Cas9 derived from *S. thermophilus* and so forth. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence. The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Francisella novicida* type II CRISPR locus), and the conserved Asp residue (D10) is mutated to alanine to convert Cas9 into a complementary-strand nicking enzyme. Similarly, the conserved His and Asn residues in the HNH domains are mutated to Alanine to convert Cas9 into a non-complementary-strand nicking enzyme. In some embodiments, both sets of mutations may be made, to convert Cas9 into a non-cutting enzyme (i.e. lacking nuclease activity). Thus, the Cas9 may comprise one or more mutations and may be used as a generic DNA binding protein with or without fusion to a functional domain, e.g. a domain which activates or inhibits gene expression. Thus in embodiments of the invention as describes herein, the Cas9 may be a mutant Cas9 lacking nuclease activity that activates or inhibits expression of a target gene guided by the RNA expressed by the vector. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the CRISPR enzyme or has a mutation as otherwise as discussed herein. In one aspect of the invention, the Cas9 enzyme may be fused to a protein, e.g., a TAG, and/or an inducible/controllable domain such as a chemically inducible/controllable domain. The Cas9 in the invention may be a chimeric Cas9 proteins; e.g., a Cas9 having enhanced function by being a chimera. Chimeric Cas9 proteins may be new Cas9 containing fragments from more than one naturally occurring Cas9. These may comprise fusions of N-terminal fragment(s) of one Cas9 homolog with C-terminal fragment(s) of another Cas9 homolog. The Cas9 can be delivered into the leukocyte in the form of mRNA. The expression of Cas9 can be under the control of an inducible promoter.

The tracrRNA and direct repeat sequences can be mutant sequences or the invention can encompass RNA of the CRISPR-Cas system that includes mutant chimeric guide sequences that allow for enhancing performance of these RNAs in leukocytes. A suitable promoter, such as the Pol III promoter, such as a U6 promoter, can be added onto the guide RNA that is advantageously delivered via AAV or particle or nanoparticle. Aspects of the invention also relate to the guide RNA being transcribed in vitro or ordered from a synthesis company and directly transfected. Expression of RNA(s), e.g., guide RNAs or sgRNA under the control of the T7 promoter driven by the expression of T7 polymerase in the leukocyte is also envisioned. In an advantageous embodiment, the leukocyte is a human leukocyte. In another preferred embodiment, the leukocyte is a non-human mammalian, e.g., primate, rodent, e.g., mouse, rat, rabbit. In a more preferred embodiment the leukocyte is a patient-specific leukocyte, e.g., a leukocyte in which one or more, e.g., a plurality, such as 3 or more, e.g., 3-50 or more, mutations associated or correlated with a patient's genetic disease, e.g., a leukocyte-associated disease, are expressed in the leukocyte, e.g., via Cas9 being present in the leukocyte and RNA(s) for such mutations delivered to the leukocyte (e.g., any whole number between 1 and 50, e.g., between 2 and 50, such as between 3 and 50 of mutations, with it noted that in some embodiments there can be up to 16 different RNA(s), e.g., sgRNAs, e.g., each having its own a promoter, in a vector, such as a lentiviral vector, and that when each sgRNA does not have its own promoter, there can be twice to thrice that amount of different RNA(s), e.g., sgRNAs, e.g., 32 or even 48 different guides delivered by one vector), whereby the CRISPR-Cas complexes result in the leukocytes having the mutations and the eukaryote, e.g., animal, containing the leukocytes being a model for the patient's genetic disease. In an advantageous embodiment, the vector may package promoter-sgRNAs targeting up to about 50 genes.

A codon optimized sequence can be a sequence optimized for a eukaryote, or for specific cells such as leukocytes. It will be appreciated that where reference is made to a polynucleotide, where that polynucleotide is RNA and is said to 'comprise' a feature such as a tracr mate sequence, the RNA sequence includes the feature. Where the polynucleotide is DNA and is said to comprise a feature such as a tracr mate sequence, the DNA sequence is or can be transcribed into the RNA that comprises the feature at issue. Where the feature is a protein, such as the CRISPR enzyme, the DNA or RNA sequence referred to is, or can be, translated (and in the case of DNA transcribed first). Furthermore, in cases where an RNA encoding the CRISPR enzyme is provided to a leukocyte, it is understood that the RNA is capable of being translated by the leukocyte into which it is delivered. By manipulation of a target sequence, Applicants mean the alteration of the target sequence, which may include the epigenetic manipulation of a target sequence. This epigenetic manipulation may be of the chromatin state of a target sequence, such as by modification of the methylation state of the target sequence (i.e. addition or removal of methylation or methylation patterns or CpG islands), histone modification, increasing or reducing accessibility to the target sequence, increasing or decreasing recruitment of the RNA polymerase II complex to the target sequence, or by promoting 3D folding. It will be appreciated that where reference is made to a method of modifying an organism or mammal including human or a non-human mammal or organism by manipulation of a target sequence in a genomic locus of interest, this may apply to the organism (or mammal) as a whole or just leukocytes or a subset thereof from that organism. Applicants envisage, inter alia, a single leukocyte or a population of leukocytes and these may preferably be modified ex vivo and then reintroduced, e.g., transplanted to make transgenic organisms that express Cas9 in certain cells. The invention in some embodiments comprehends a method of modifying a eukaryote, such as a Cas9 transgenic eukaryote comprising delivering, e.g., via vector(s) and/or particle(s) and/or nanoparticles a non-naturally occurring or engineered composition. The composition comprises: I. a first regulatory element operably linked to (a) a first guide sequence capable of hybridizing to a first target sequence, and (b) at least one or more tracr mate sequences, II. a second regulatory element operably linked to (a) a second guide sequence capable of hybridizing to a second target sequence, and (b) at least one or more tracr mate sequences, III. a third regulatory element operably linked to (a) a third guide sequence capable of hybridizing to a third target sequence, and (b) at least one or more tracr mate sequences, and IV. a fourth regulatory element operably linked to a tracr sequence. There can be additional regulatory element(s) operably linked to additional guide sequence(s). Optionally, the composition can involve V. a fifth regulatory element operably linked to an enzyme-coding sequence encoding a CRISPR enzyme (e.g., for establishing the Cas9 transgenic eukaryote). Components I, II, III and IV (as well as any other regulatory element(s) linked to additional guide sequence(s)) are located on the same or different vectors and/or particles and/or nanoparticles of the system. When transcribed, the tracr mate sequence hybridizes to the tracr sequence and the first, second and the third guide sequences direct sequence-specific binding of a first, second and third CRISPR complexes to the first, second and third target sequences respectively, wherein the first CRISPR complex comprises the CRISPR enzyme complexed with (1) the first guide sequence that is hybridizable to the first target sequence, and (2) the tracr mate sequence that is hybridizable to the tracr sequence, wherein the second CRISPR complex comprises the CRISPR enzyme complexed with (1) the second guide sequence that is hybridizable to the second target sequence, and (2) the tracr mate sequence that is hybridizable to the tracr sequence, and wherein the third CRISPR complex comprises the CRISPR enzyme complexed with (1) the third guide sequence that is hybridizable to the third target sequence, and (2) the tracr mate sequence that is hybridizable to the tracr sequence, whereby in a Cas9 transgenic eukaryote or leukocyte thereof, at least three (3) mutations may be induced, and advantageously the mutations are correlated or associated with an aberrant leukocyte response or a leukocyte-associated disease condition, whereby the eukaryote or leukocyte becomes a model of the response or disease, e.g., an immune system disorder. The invention also provides a vector system as described herein. The system may comprise one, two, three or four different vectors; and the system may comprise one, two, three or four different nanoparticle complex(es) delivering the component(s) of the system. Components I, II, III and IV may thus be located on one, two, three or four different vectors, and may be delivered by one, two, three or four different particle or nanoparticle complex(es) or AAVs or components I, II, III and IV can be located on same or different vector(s)/particle(s)/nanoparticle(s), with all combinations of locations envisaged. And complexes that target leukocytes or subsets thereof are advantageous.

In some methods of the invention any or all of the polynucleotide sequence encoding the CRISPR enzyme, the first and the second guide sequence, the first and the second tracr mate sequence or the first and the second tracr sequence, is/are RNA; and advantageously delivered via nanoparticle complex(es) or a cell-penetrating peptide (CPP). Embodiments of the invention also comprehend the guide RNAs comprising a guide sequence fused to a tracr mate sequence and a tracr sequence. In an aspect of the invention the Cas protein is codon optimized for expression in a eukaryotic cell, preferably a mammalian cell, e.g., a primate or rodent cell such as a mouse cell or a human cell (e.g. a mammalian, mouse or human leukocyte). The invention also comprehends an engineered, non-naturally occurring vector system. The system comprises one or more vectors comprising: (a) a first regulatory element operably linked to each of two or more e.g. three, CRISPR-Cas system guide RNAs that target a first strand, a second strand and a third strand respectively of a double stranded DNA molecule. The system can also comprise (b) a second regulatory element operably linked to a Cas protein. Components (a) and (b) are located on same or different vectors of the system, but advantageously separate vectors as it is preferred that leukocytes receiving (a) contain Cas9, e.g., via the leukocytes being those of a transgenic Cas9 eukaryote (whereby (b) may have been administered to cells that gave rise to the eukaryote). The guide RNAs target DNA and at least three mutations are induced in the leukocytes, e.g., mutations correlated to or associated with an aberrant leukocyte response or a disease associated with leukocytes, such as an immune system disorder or cancer.

In one aspect, the invention provides a method of modifying a target polynucleotide in a leukocyte, for instance in order to modulate leukocyte activity. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence; and advantageously the complex or a component thereof has been delivered via nanoparticle complex(es). In some embodiments, said cleavage comprises cleaving one or two strands at the location of the target sequence by said CRISPR enzyme. In some embodiments, said cleavage results in decreased transcription of a target gene. In some embodiments, said cleavage results in increased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. The mutation can be a mutation correlated to or associated with an aberrant leukocyte response or a leukocyte-associated disease condition, such as an immune system disorder. In some embodiments, said mutation results in one or more amino acid changes in a protein expressed from a gene comprising the target sequence. In some embodiments, said mutation results in one or more changes in promoter or enhancer sites that modulate gene expression. In some embodiments, said mutation results in one or more changes in splice sites that modulate splicing of the gene. In some embodiments, vectors are delivered to the leukocyte in a transgenic Cas9 eukaryote. In some embodiments, said modifying takes place in said leukocyte in a cell culture, preferably a primary cell culture. In one aspect, the invention provides a method of generating a model leukocyte or a model Cas9 transgenic eukaryote comprising mutated gene(s) in leukocytes, e.g., having one or more, e.g., a plurality, e.g., 3 or more, such as 3-50 or more mutations correlated to or associated with an aberrant leukocyte response or a leukocyte-associated disease such as an immune system disorder (e.g., any whole number between 1 and 50, e.g., between 2 and 50, such as between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector). In some embodiments, the mutated gene is any gene involved in leukocyte responses (e.g. leukocyte activation, inhibition, differentiation, exhaustion, adhesion, death or proliferation) or associated with an increase in the risk of having or developing a disease.

In some methods, a target polynucleotide can be inactivated to effect the modification of the expression in a leukocyte. For example, upon the binding of a CRISPR complex to a target sequence in a leukocyte, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In certain embodiments, the target sequence is flanked or followed, at its 3' end, by a PAM (protospacer-adjacent motif) suitable for the CRISPR enzyme, typically a Cas and in particular a Cas9. For example, a suitable PAM is 5'-NRG or 5'-NNGRR for SpCas9 or SaCas9 enzymes (or derived enzymes), respectively.

Delivery can be in the form of a vector which may be a plasmid or other nucleic acid molecule form, especially when the delivery is via a nanoparticle complex; and the vector also can be viral vector, such as a herpes, e.g., herpes simplex virus, *lenti-* or baculo- or adeno-viral or adeno-associated viral vectors, but other means of delivery are known (such as yeast systems, microvesicles, gene guns/ means of attaching vectors to gold nanoparticles and cell-penetrating peptides (CPP)) and are provided, especially as to those aspects of the complex not delivered via a nanoparticle complex. A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell; and advantageously the complex or a component thereof is delivered via nanoparticle complex(es). Also envisaged is a method of delivering the present CRISPR enzyme comprising delivering to a leukocyte mRNA encoding the CRISPR enzyme; and advantageously the complex or a component thereof has been delivered via nanoparticle complex(es). It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed. When not delivering via a nanoparticle complex, lentivirus is a preferred vector. In certain embodiments, multiple RNA(s) or guide RNAs or sgRNAs formulated in one or more delivery vehicles (e.g., where some guide RNAs are provided in a vector and others are formulated in nanoparticles); and these may be provided alone (e.g., when Cas9 is already in a leukocyte) or with a Cas9 delivery system. In certain embodiments, the Cas9 is also delivered in a nanoparticle formulation. In certain instances the RNA(s) or guide RNA or sgRNA-vector and/or particle and/or nanoparticle formulation(s) and the Cas9 vector and/or particle and/or nanoparticle formulation(s) may be delivered separately or may be delivered substantially contemporaneously (i.e., co-delivery). Sequential delivery could be done at separate points in time, separated by days, weeks or even months. And as Cas9 is advantageously present in a transgenic organism or leukocytes derived therefrom in the practice of the invention, e.g., through being constitutively or conditionally or inducibly present, sequential delivery can include initially administering or delivering the Cas9 vector and/or particle and/or nanoparticle formulation(s) to cells that give rise to the non-human Cas9 transgenic eukaryote, and thereafter, at a suitable time in the life of the transgenic eukaryote, administering the RNA(s) or guide RNA or sgRNA-vector and/or particle and/or nanoparticle formulation(s), e.g., so as to give rise to one or more, advantageously e.g., a plurality, e.g., 3 or more, advantageously 3-50 or more mutations in leukocytes in or derived from the transgenic eukaryote (e.g., any whole number between 1 and 50, e.g., between 2 and 50 such as between 3 and 50, of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), and advantageously the mutations are associated or correlated with a leukocyte response or a leukocyte-associated disease, whereby the transgenic eukaryote or leukocytes derived therefrom is a model of response or a disease, e.g., an immune system disorder. Multiple mutations may thus be introduced using any number of sgRNAs, e.g. the vector may comprise at least 3 sgRNAs, at least 8 sgRNAs, at least 16 sgRNAs, at least 32 sgRNAs, at least 48 sgRNAs, or at least 50 sgRNAs. Alternatively, the vector may comprise 1-2 sgRNAs, 1-3 sgRNAs, 1-4 sgRNAs, 1-5 sgRNAs, 3-6 sgRNAs, 3-7 sgRNAs, 3-8 sgRNAs, 3-9 sgRNAs, 3-10 sgRNAs, 3-16 sgRNAs, 3-30 sgRNAs, 3-32 sgRNAs, 3-48 sgRNAs or 3-50 sgRNAs. In certain embodiments, vector (e.g., AAV, adenovirus, lentivirus) and/or particle and/or nanoparticle formulations comprising one or more RNA(s) e.g. guide RNAs or sgRNA are adapted for delivery in vitro, ex vivo or in vivo in the context of the CRISPR-Cas system, e.g., so as to form CRISPR-Cas complexes in vitro, ex vivo or in vivo, to different target genes in leukocytes. Multiplexed gene targeting using nanoparticle formulations comprising one or more guide RNAs are also envisioned. In an embodiment, a nanoparticle formulation comprising one or more components of the CRISPR-Cas system is provided. In an embodiment, a RNA(s) or gRNA or sgRNA-nanoparticle formulation comprising one or more guide RNAs or sgRNA is provided. In certain embodiments, a composition comprising a nanoparticle formulation comprising one or more components of the CRISPR-Cas system is provided. In certain embodiments, a composition, e.g., a pharmaceutical or veterinary composition, comprising a vector (e.g., AAV, adenovirus, lentivirus) and/or particle and/or nanoparticle formulation comprising one or more components of the CRISPR-Cas system and/or nucleic acid molecule(s) coding therefor, advantageously with such nucleic acid molecule(s) operably linked to promoter(s) is provided. Accordingly, in certain embodiments, it may be useful to deliver the RNA(s) or guide RNA or sgRNA, e.g., vector and/or particle and/or nanoparticle formulations separately from the Cas9 or nucleic acid molecule(s) coding therefor. A dual-delivery system is envisaged such that the Cas 9 may be delivered via a vector and the RNA(s), e.g., guide RNAs or sgRNA are/is provided in a particle or nanoparticle formulation, for example, first Cas9 vector is delivered via a vector system followed by delivery of sgRNA-nanoparticle formulation. Vectors may be considered in the broadest light as simply any means of delivery, rather than specifically viral vectors.

In one aspect, the present invention provides a Cas9 transgenic eukaryote, e.g., mouse. In certain preferred embodiments, the Cas 9 transgenic eukaryote, e.g., mouse comprises a Cas9 transgene knocked into the Rosa26 locus. In one aspect, the present invention provides a Cas9 transgenic eukaryote, e.g., mouse wherein Cas9 transgene is driven by the ubiquitous CAG promoter thereby providing for constitutive expression of Cas9 in all tissues/cells/cell types of the mouse. In one aspect, the present invention provides a Cas9 transgenic eukaryote, e.g., mouse wherein the Cas9 transgene driven by the ubiquitous CAG promoter further comprises a Lox-Stop-polyA-Lox (LSL) cassette (Rosa26-LSL-Cas9 mouse) thereby rendering Cas9 expression inducible by the Cre recombinase. In one aspect, the present invention provides a constitutive Cas9 expressing eukaryote, e.g., mouse line obtained by crossing of the Rosa26-LSL-Cas9 mouse with a beta-actin-Cre eukaryote, e.g., mouse line. In certain embodiments, progeny(ies) derived from said Cas9 expressing eukaryote, e.g., mouse line may be successfully bred over at least five generations without exhibiting increased levels of genome instability or cellular toxicity. In one aspect, the present invention provides a modular viral vector construct comprising a plurality of sgRNAs driven by a single RNA polymerase III promoter (e.g., U6), wherein the sgRNAs are in tandem, or where each of the sgRNAs in driven by one RNA polymerase III promoter. In one aspect, the present invention provides a modular viral vector construct comprising one or more cassettes expressing Cre recombinase, a plurality of sgRNAs to guide Cas9 cutting, and a HDR template to model the dynamics of a complex pathological disease or disorder involving two or more genetic elements simultaneously using a single vector construct. In certain non-limiting embodiments, the complex pathological disease or disorder is a disease associated with leukocytes, e.g. an immune system disorder or cancer. It can be appreciated that any kind of disease associated with leukocytes is within the scope of the present invention. In a preferred embodiment, the present invention provides for modeling of immune system disorders. In one aspect, the present invention provides a modular viral vector construct to model the dynamics of multiple gene mutations in leukocytes simultaneously using a single vector. In certain embodiments, the modular viral vector construct comprises one or more cassettes expressing Cre recombinase, a plurality of sgRNAs to guide Cas9 cutting, and optionally including a Homology Directed Repair (HDR) template to introduce specific gain-of-function mutations or precise sequence substitution in target loci. In one aspect, the present invention provides a method for simultaneously introducing one or more mutations ex vivo in leukocytes, or in vivo in the same animal comprising delivering a single viral vector construct, wherein the viral vector construct comprises one or more cassettes expressing Cre recombinase, a plurality of sgRNAs to guide Cas9 cutting, and a HDR template for achieving targeted insertion or precise sequence substitution at specific target loci of interest. The present invention provides a method for generating loss-of-function mutation or mutations and/or gain-of-function mutation or mutations. It can be readily appreciated that mutations in any gene expressed in leukocytes is within the scope of the present invention, particularly genes associated or correlated with leukocyte activity and responses such as activation, inhibition, differentiation, exhaustion, adhesion, death and proliferation. In one aspect, the present invention provides a method for delivering ex vivo or in vivo of any of the constructs disclosed herein into leukocytes. When AAV is used selection of the AAV serotype is based on its suitability and specificity for a tissue type. In certain preferred embodiments, a lentiviral vector is used for delivery to leukocytes. In one aspect, the present invention provides a method for ex vivo and/or in vivo genome editing comprising delivering any of the above modular viral vector constructs, which comprise one or more cassettes expressing Cre recombinase, a plurality of sgRNAs to guide Cas9 cutting, and optionally one or more HDR template(s), into a Cas9 transgenic mouse (e.g., Rosa26-LSL-Cas9) or into leukocytes from a Cas9 transgenic mouse (e.g., Rosa26-LSL-Cas9). In certain embodiments, the viral vector is lentivirus. In one aspect, the present invention provides a Cas9 transgenic non-human eukaryote, or leukocytes derived therefrom, e.g., an animal or cellular model for an aberrant leukocyte response or a disease associated with leukocytes, e.g. an immune system disorder or cancer, said model having loss-of-function mutations and/or gain-of-function mutation in leukocytes in one or more genes associated with the response or disease. It can be appreciated that using the novel CRISPR-Cas9 tools disclosed herein, a Cas9 transgenic non-human eukaryote and leukocytes derived therefrom, e.g., an animal or cellular model with multiple mutations in any number of loci in leukocytes can be envisioned and are within the scope of the present invention. It will be appreciated that such a transgenic non-human eukaryote or leukocytes derived therefrom, e.g., an animal or cellular model provides a valuable tool for research purposes, e.g., to delineate specific roles/contribution of individual genes expressed in leukocytes in leukocyte responses and to progression of a disease associated with leukocytes, to recapitulate specific combinations of mutations in a given leukocyte type, and opens the door for developing and testing new therapeutic interventions for diseases associated with leukocytes involving mutations at one or multiple loci. Such uses are within the scope of the present invention. In one aspect, the present invention provides a method of treating or inhibiting the development of a disease associated with leukocytes in a subject in need thereof, comprising providing individualized or personalized treatment (or an individualized or personalized model or patient specific-modeling) comprising: delivering RNA(s), e.g., sgRNA, that targets a genetic locus correlated or associated with the disease, e.g. an immune system disorder or cancer, to a Cas9 non-human transgenic eukaryote (e.g., animal, mammal, primate, rodent, fish etc as herein discussed) or leukocytes derived therefrom, e.g., via vector such as AAV, adenovirus, lentivirus, or particle(s) or nanoparticle(s), whereby mutation(s), advantageously a plurality, e.g., 1 or more, e.g., a plurality, such as 3 or more or 3-50 or more mutations (e.g., any whole number between 3 and 50 or more of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), are induced in the eukaryote or leukocytes derived therefrom and the eukaryote or leukocytes therefrom is/are a model for the disease; and obtaining and/or extrapolating data from the Cas9 non-human transgenic eukaryote or leukocytes derived therefrom to humans to provide individualized or personalized treatment. The obtaining and/or extrapolating data can be subjecting the eukaryote or leukocytes derived therefrom to putative treatment(s) and/or therapy(ies), e.g., gene therapy, ascertaining whether such putative treatment(s) and/or therapy(ies) give rise to remission or treatment or alleviation or remission of the disease or to a process associated with disease remission (e.g. leukocyte activation, inactivation or differentiation), and if so, then administering in dosing scaled to a 70 kg individual or subject, the putative treatment(s) and/or therapy(ies). The invention thus allows for one to ascertain whether a particular treatment and/or therapy may be effective as to a particular individual's disease.

In certain aspects the invention provides vector(s), particle(s) or nanoparticle(s) containing nucleic acid molecule(s), whereby in vivo in a eukaryotic cell containing or conditionally or inducibly expressing Cas9: the vector(s) express(es) a plurality of RNAs to guide the Cas9 and optionally delivers donor templates (e.g., HDR templates, and in certain embodiments advantageously includes and delivers such donor templates), and optionally in the event Cas9 is conditionally or inducibly expressed in the cell that which induces Cas9, e.g., Cre recombinase; whereby a plurality of specific mutations or precise sequence substitutions in a plurality of target loci are introduced. The vector(s) can be a viral vector such as lentivirus, adenovirus, or adeno-associated virus (AAV), e.g., AAV6 or AAV9. The Cas9 can be from S. thermophiles, S. aureus, or S. pyogenes. The eukaryotic cell (e.g. leukocyte) can comprise a Cas9 transgene functionally or operatively linked to a constitutive promoter, or a tissue specific promoter, or an inducible promoter; and, the eukaryotic cell (e.g., leukocyte) can be part of a non-human transgenic eukaryote, e.g., a non-human mammal, primate, rodent, mouse, rat, rabbit, canine, dog, cow, bovine, sheep, ovine, goat, pig, fowl, poultry, chicken, fish; advantageously a mouse. The leukocyte can be an isolated eukaryotic cell, e.g., from any of the foregoing non-human animals or from a human or the leukocyte can be part of a non-human transgenic animal as herein discussed. The leukocyte or non-human transgenic animal can express an additional protein or enzyme, such as Cre; and, the expression of Cre can be driven by coding therefor functionally or operatively linked to a constitutive promoter, or a tissue specific promoter, or an inducible promoter.

The RNAs to guide Cas9 can comprise CRISPR RNA and transactivating (tracr) RNA. Advantageously, the RNAs to guide Cas9 can comprise chimeric single guide RNA (sgRNA). Indeed, it is advantageous that the RNAs to guide Cas9 can comprise chimeric single guide RNA (sgRNA). The tracr sequence and tracr mate sequence along the length of the shorter of the two when optimally aligned can be about or more than about 25%, 30%, 40%, 50%, 60%, 70%, 80%, 90%, 95%, 97.5%, 99%, or higher. The tracr sequence can be about or more than about 5, 6, 7, 8, 9, 10, 11, 12, 13, 14, 15, 16, 17, 18, 19, 20, 25, 30, 40, 50, or more nucleotides in length. The degree of complementarity between a guide sequence and its corresponding target sequence can be about or more than about 50%, 60%, 75%, 80%, 85%, 90%, 95%, 97.5%, 99%, or 100%. A guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. A guide or RNA or sgRNA can be less than about 75, 50, 45, 40, 35, 30, 25, 20, 15, 12, or fewer nucleotides in length.

The vector(s) can include the regulatory element(s), e.g., promoter(s). The vector(s) can comprise at least 3 or 8 or 16 or 32 or 48 or 50 RNA(s) (e.g., sgRNAs), such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as lentivirus or AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (http://www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV or lentivirus vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., http://nar.oxfordjournals.org/content/34/7/e53.short, http://www.nature.com/mt/journal/v16/n9/abs/mt2008144a.html). In an advantageous embodiment, AAV or lentivirus may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters—especially as to the numbers of RNAs or guides or sgRNAs discussed herein, without any undue experimentation.

The RNA(s), e.g., sgRNA(s), can be functionally or operatively linked to regulatory element(s) and hence the regulatory element(s) drive expression. The promoter(s) can be constitutive promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter U6.

Advantageously, each RNA (e.g., sgRNA) is specific to a different target sequence. Each different target sequence can be associated with or correlated to a form of disease associated with or correlated to or related to leukocytes or white blood cells or a leukocyte response or associated with an immune system disorder or with a cancer or with the response of leukocytes to cancer. Each RNA or sgRNA can be specific to a different target sequence but these RNA(s) or sgRNA(s) target specific gene sequences associated with or correlated to a disease of leukocytes or white blood cells or a leukocyte response or associated with an immune system disorder or with a cancer or with the response of leukocytes to cancer, advantageously a particular type or form of disease of leukocytes or white blood cells or a leukocyte response or associated with an immune system disorder or with a cancer or with the response of leukocytes to cancer; for instance each RNA or sgRNA can be specific to a different target sequence but the target sequences of the RNA(s) or sgRNA(s) are associated with or correlated to the same type or form of disease associated with or correlated to or related to leukocytes or white blood cells or a leukocyte response or associated with an immune system disorder or with a cancer or with the response of leukocytes to cancer; such as leukopenia, or leukemia (e.g., lymphocytic leukemia, myelogenous leukemia).

Advantageously, each sgRNA can be driven by an independent promoter, e.g., U6 promoter. The vector can be a lentiviral vector, e.g., a U6-sgRNA lentiviral vector. Each of the sgRNAs can target a different gene expressed in leukocytes, e.g. a gene involved in a leukocyte response or associated with an immune system disorder. The sgRNAs can target one or more genes expressed in leukocytes so as to introduce loss-of-function mutation(s) and/or gain-of-function mutation(s). From 1 to 50 or more, e.g., a plurality, such as 3 or more or 3-50 or more specific mutations or precise sequence substitutions in from 1 to 50 or more e.g., a plurality, such as 3 or more or 3-50 or more target loci can be introduced. The eukaryotic cell can be a mammalian leukocyte, e.g., a mouse leukocyte, such as a mouse leukocyte that is part of or derived from a transgenic mouse having cells that express Cas9. The invention also comprehends a method for introducing one or more mutations ex vivo in Cas9-expressing leukocyte(s), or in vivo in a transgenic non-human mammal having leukocytes that express Cas9, comprising delivering to leukocytes of the mammal the vector as herein-discussed. The method can comprise delivering to leukocytes of or from the transgenic non-human mammal, and the transgenic non-human mammal is a transgenic mouse having leukocytes that express Cas9, e.g., a mouse that has had a Cas9 transgene knocked into the Rosa26 locus. The Cas9 transgene can further comprise a Lox-Stop-polyA-Lox(LSL) cassette thereby rendering Cas9 expression inducible by Cre recombinase. The invention additionally comprehends a method for modeling an aberrant leukocyte response or a disease associated with leukocytes comprising introducing one or more, advantageously multiple, mutations ex vivo in Cas9-expressing leukocyte(s), or in vivo in a transgenic non-human mammal having leukocytes that express Cas9, comprising delivering to the leukocyte(s) the vector as herein-discussed, wherein the specific mutations or precise sequence substitutions are or have been correlated to the disease. This method can comprise delivering to leukocytes of the transgenic non-human mammal the vector, and the transgenic non-human mammal is a transgenic mouse having cells that express Cas9, e.g., a mouse that has had a Cas9 transgene knocked into the Rosa26 locus; and, the Cas9 transgene can further comprise a Lox-Stop-polyA-Lox(LSL) cassette thereby rendering Cas9 expression inducible by Cre recombinase. The invention also envisions an individualized or personalized treatment of a disease associated with leukocytes in a subject in need of such treatment comprising: (a) introducing one or more, e.g., multiple mutations ex vivo in Cas9-expressing leukocyte(s), or in vivo in a transgenic non-human mammal having leukocytes that express Cas9, comprising delivering to leukocytes of the tissue, organ, cell or mammal the vector as herein-discussed, wherein the specific mutations or precise sequence substitutions are or have been correlated to the disease; (b) testing treatment(s) for the disease on the leukocytes to which the vector has been delivered that have the specific mutations or precise sequence substitutions correlated to the disease; and (c) treating the subject based on results from the testing of treatment(s) of step (b). The method can comprise delivering to leukocytes of the transgenic non-human mammal the vector, and the transgenic non-human mammal is a transgenic mouse having leukocytes that express Cas9, and the disease is a leukocyte-associated disease, e.g., an immune disorder or cancer.

The leukocyte can be a mammalian cell, e.g., a mouse cell, such as a mouse cell that is part of a transgenic mouse having cells that contain or express or that are able to be induced to express or that conditionally express Cas9. The invention also comprehends a method for introducing one or more, e.g., multiple mutations ex vivo in Cas9-expressing or—containing leukocytes or leukocytes containing or expressing or that are able to be induced to express or that conditionally express Cas9. Such leukocytes can be transplanted into a non-human animal of the species from which they came. For example, a transgenic mouse having cells that contain or express or that are able to be induced to express or that conditionally express Cas9 can have leukocytes removed therefrom. Those cells can be transplanted into a second mouse that has had its immune system altered, e.g., a mouse that has been irradiated and/or had bone marrow removed and/or irradiated, whereby the second mouse has had its immune system altered. That transplantation can be before or after one or more, e.g., multiple, mutations are introduced via delivery of RNA(s), e.g., sgRNA(s) via vector(s) as herein discussed. Accordingly, the second mouse may not be a transgenic mouse having cells that contain or express or that are able to be induced to express or that conditionally express Cas9; but, it can be a mouse that has been altered such that its immune system has leukocytes that contain or express or that are able to be induced to express or that conditionally express Cas9, e.g., such leukocytes into which one or more, e.g., multiple, mutations are introduced. The invention also comprehends a method for introducing one or more, e.g., multiple mutations, in vivo in a transgenic non-human animal, e.g., mammal (of the types herein discussed) having leukocyte(s) that express or contain Cas9 or that are able to be induced to express or that conditionally express Cas9, comprising delivering to leukocyte(s) of the tissue, organ, cell or mammal the vector as herein-discussed. The transgenic non-human mammal can be a transgenic mouse having cells that express or contain Cas9 or that are able to be induced to express or that conditionally express Cas9, e.g., a mouse that has had a Cas9 transgene knocked into the Rosa26 locus. The Cas9 transgene can further comprise a Lox-Stop-polyA-Lox(LSL) cassette thereby rendering Cas9 expression inducible by Cre recombinase. The invention additionally comprehends a method for modeling a leukocyte-associated disease, e.g., an immune disorder comprising introducing one or more, e.g., multiple, mutations ex vivo in a leukocytes that express or contain Cas9 or that are able to be induced to express or that conditionally express Cas9, or in vivo in a transgenic non-human animal, e.g., mammal (e.g., of the types herein discussed) having leukocytes that express or contain Cas9 or that are able to be induced to express or that conditionally express Cas9, comprising delivering to leukocytes of the animal, e.g., mammal a vector as herein-discussed, wherein the specific mutation(s) or precise sequence substitutions are or have been correlated to the leukocyte-associated disease, e.g., an immune disorder. This method can comprise delivering to leukocytes of the transgenic non-human animal, e.g., mammal the vector, and the transgenic non-human animal, e.g., mammal is a transgenic mouse having leukocytes that express Cas9, e.g., a mouse that has had a Cas9 transgene knocked into the Rosa26 locus; and, the Cas9 transgene can further comprise a Lox-Stop-polyA-Lox(LSL) cassette thereby rendering Cas9 expression inducible by Cre recombinase. The invention also envisions an individualized or personalized treatment of a leukocyte-associated disease, e.g., an immune disorder, in a subject in need of such treatment comprising: (a) introducing multiple mutations ex vivo in leukocytes that express or contain Cas9 or that are able to be induced to express or that conditionally express Cas9, or in vivo in a transgenic non-human animal, e.g., mammal having leukocytes that express or contain Cas9 or that are able to be induced to express or that conditionally express Cas9, comprising delivering to the leukocyte(s)a vector as herein-discussed, wherein the specific mutations or precise sequence substitutions are or have been correlated to the leukocyte-associated disease, e.g., an immune disorder or cancer; (b) testing treatment(s) for the leukocyte-associated disease, e.g., an immune disorder on the leukocytes to which the vector has been delivered that have the specific mutations or precise sequence substitutions correlated to the leukocyte-associated disease, e.g., an immune disorder or cancer; and (c) treating the subject based on results from the testing of treatment(s) of step (b). The method can comprise delivering to leukocytes of the transgenic non-human animal, e.g., mammal the vector, and the transgenic non-human animal, mammal can be a transgenic mouse having cells that express Cas9.

The invention comprehends a method of inducing one or more mutations in vitro or ex vivo in a eukaryotic cell as herein discussed comprising delivering to leukocyte(s) a vector as herein discussed. The invention further comprehends a method of inducing one or more mutations in vivo in the non-human transgenic eukaryote, e.g., animal or mammal, as herein discussed comprising delivering to said non-human transgenic eukaryote a vector as herein discussed. The delivery can be to leukocytes. The mutation(s) can include the introduction, deletion, or substitution of one or more nucleotides at each target sequence of cell(s) via the guide(s) or RNA(s) or sgRNA(s) resulting in loss-of-function and/or gain of function of the target(s). The mutations can include the introduction, deletion, or substitution of 1-75 nucleotides at each target sequence of said cell(s) via the guide(s) or RNA(s) sgRNA(s) resulting in loss-of-function or gain of function of the target(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 40, 45, 50, 75, 100, 200, 300, 400 or 500 nucleotides at each target sequence of said cell(s) via the guide(s) or RNA(s) or sgRNA(s) resulting in loss-of-function or gain of function of the target. The method or mutation(s) thereof can induce a leukocyte-associated disease, e.g., an immune disorder or cancer.

The invention comprehends a method for identifying genes, mutations in genes or combinations thereof which are associated with or correlated to leukocyte-associated disease, e.g., an immune disorder or cancer, comprising a method of inducing one or more mutations in vitro or ex vivo in leukocyte(s) as herein discussed or inducing one or more mutations in vivo in a non-human transgenic eukaryote, e.g., animal or mammal, as herein discussed, and identifying leukocyte-associated disease, e.g., an immune disorder or cancer, resulting from such mutations(s). The method can include control cell(s) or eukaryote(s) that do not receive introduction of said mutation(s).

The invention also comprehends a method for modeling leukocyte-associated disease, e.g., an immune disorder comprising inducing one or more mutations in vivo in a non-human transgenic eukaryote as herein discussed, e.g., delivering to a non-human transgenic eukaryote one or more vectors or RNA(s) guide(s) or sgRNA(s) as herein discussed.

The invention additionally comprehends a method for generating non-human transgenic eukaryotes having leukocyte-associated disease, e.g., an immune disorder or cancer, by introducing, as herein discussed, the one or more mutations as herein discussed. The invention additionally comprehends a non-human transgenic eukaryote having leukocyte-associated disease, e.g., an immune disorder or cancer; for instance, such a eukaryote produced by a method herein discussed. Such a non-human eukaryote contains or expresses or conditionally expresses Cas9 and has a leukocyte-associated disease, e.g., an immune disorder.

The invention also comprehends a method for the identification of a treatment, e.g., chemical or gene therapy treatment, for leukocyte-associated disease, e.g., an immune disorder or cancer, comprising applying, administering or delivering one or more treatments to the leukocyte-associated disease, e.g., an immune disorder or cancer, to non-human transgenic eukaryote as herein discussed and identifying whether the leukocyte-associated disease, e.g., an immune disorder or cancer, has improved. The method can comprise applying, administering or delivering different doses of the treatment and/or employing different routes of administration and/or different carriers or excipients and/or applying, administering or delivering at different time intervals, e.g., applying, administering or delivering different does at different time intervals.

The invention also comprehends a method of treatment of a leukocyte-associated disease, e.g., an immune disorder or cancer, e.g., such a leukocyte-associated disease, e.g., an immune disorder or cancer, identified in a herein method of identification or modeling, or another leukocyte-associated disease, e.g., an immune disorder or cancer, in a subject in need thereof, comprising treating the subject based on the results from the herein identification or modeling method.

The invention also comprehends kits; e.g., comprising vector(s) as herein discussed and one or more leukocyte(s) or non-human transgenic eukaryotes as herein discussed; and advantageously the kit includes instructions for performing a method as herein discussed.

The invention comprehends a method for modulating leukocyte activity, comprising delivering to a leukocyte a vector containing nucleic acid molecule(s), whereby the leukocyte contains or expresses or is able to be induced to express or conditionally expresses Cas9 and the vector expresses one or more RNAs to guide the Cas9 and optionally delivers donor template(s) to introduce mutations in one or more target genetic loci in the leukocyte, thereby modulating expression of one or more genes expressed in the leukocyte. The RNAs to guide Cas9 can comprise chimeric single guide RNA (sgRNA). Each sgRNA can be driven by a U6 promoter. The vector can be a lentiviral vector. The vector can be a U6-sgRNA lentiviral vector. The sgRNAs can target one or more genes expressed in the leukocyte so as to introduce loss-of-function mutations. The leukocyte can be a mammalian leukocyte, e.g., a leukocyte derived from a non-human transgenic animal having cells that contain or express or are able to be induced to express or conditionally express Cas9, and the vector is delivered to the leukocyte ex vivo. The non-human transgenic animal having cells that contain or express or are able to be induced to express or conditionally express Cas9 can be a mammal or a primate, or a rodent, or a mouse, or a rat or a rabbit, or a canine or dog, or a cow or bovine, or a sheep or ovine or a goat or a pig, or fowl or poultry, or a chicken, or a fish, e.g., a mouse leukocyte, such as a mouse leukocyte from a transgenic mouse having cells that contain or express or are able to be induced to express or conditionally express Cas9.

The transgenic mouse having cells that contain or express or are able to be induced to express or conditionally express Cas9 can comprises a mouse that has had a Cas9 transgene knocked into the Rosa26 locus. The leukocyte can be a dendritic cell. The leukocyte can be a T cell. The modulation can be an aberrant leukocyte response or activation or inhibition or differentiation or exhaustion or adhesion or proliferation; or induction of mutation(s) such as loss of function and/or gain of function mutations.

The invention includes genetic manipulation of cell line or primary cells or primary cells that were activated or differentiated to another cell type or cell subset.

The invention also envisions a method of identifying a gene associated with a leukocyte response, comprising: (a) delivering to a plurality of leukocytes a plurality of different vectors containing nucleic acid molecule(s), whereby the leukocytes contain or express or are able to be induced to express or conditionally express Cas9 and each vector expresses one or more RNAs (i) to guide the Cas9 and optionally delivers donor template(s) to introduce mutations in different target genetic loci in the leukocytes or (ii) to guide the Cas9 to activate or inhibit expression of a target gene, thereby modulating expression of different genes expressed in the leukocytes; (b) measuring a response in the leukocytes; and (c) isolating leukocyte(s) in which the response is modulated following delivery of the vector, thereby identifying gene(s) associated with the leukocyte response. In one embodiment, the genes associated with the leukocyte response are identified by sequencing one or more nucleic acid molecules (e.g. guide RNAs) present in the isolated leukocytes. The leukocyte response can be activation, inhibition, differentiation migration, exhaustion, adhesion, or proliferation. The leukocytes can comprise dendritic cells. The response can comprise activation. The dendritic cells can be stimulated with a cytokine, another cell (e.g. activated T cell), agonist or antagonist antibodies targeting surface proteins, chemical agents, e.g. a toxin, such as diphtheria toxin or bacterial lipopolysaccharide (LPS), or with any pathogen (virus, bacteria, fungus) or with other pathogen components (e.g., beta-glucan from fungi) or their synthetic mimics (e.g., poly I:C to mimic viral double stranded RNA). The stimulation can be in the presence of an interleukin such as interleukin-10 (IL-10) or can be any combination of factors. Activation can be measured by monitoring transcription factors, cytokines, cell surface markers or any molecule that is induced in the leukocyte cell, e.g. TNF-α or CD86 expression in the dendritic cells upon LPS stimulation. Monitoring of the leukocyte response can be done using ELISA for secreted factors, viability assays or fluorescent staining for surface or intracellular markers. The RNAs to guide Cas9 can comprise chimeric single guide RNA (sgRNA). Each sgRNA can be driven by a U6 promoter. The vector can be a lentiviral vector, e.g., a U6-sgRNA lentiviral vector. The sgRNAs can target one or more genes expressed in the leukocytes so as to introduce loss-of-function mutations. Gain of function mutations can also be introduced. A decreased response in a leukocyte can be indicative that a gene mutated in the leukocyte by delivery of the vector is a positive regulator of the response. An increased response in a leukocyte can indicative that a gene mutated in the leukocyte by delivery of the vector is a negative regulator of the response. The leukocytes can be mammalian leukocytes, e.g., mouse leukocytes. The mouse leukocytes can be from a transgenic mouse having cells that contain or express or are able to be induced to express or conditionally express Cas9. The transgenic mouse having cells that contain or express or are able to be induced to express or conditionally express Cas9 can comprises a mouse that has had a Cas9 transgene knocked into the Rosa26 locus. The leukocytes can comprise T cells. The response can comprise differentiation. The T cells can be stimulated with an interleukin, e.g., interleukin-12. The response can comprise differentiation to a Th1 phenotype. The T cells can be stimulated with interleukin-4. The response can comprise differentiation to a Th2 phenotype. The T cells can be stimulated with TGF-β. The response can comprise differentiation to a Treg phenotype. The T cells can be stimulated with TGF-β and an interleukin, e.g., interleukin-6. The response can comprise differentiation to a Th17 phenotype. The T cells can be from a transgenic mouse having cells that express Cas9 and an ovalbumin-specific αβ-T cell receptor. A library of vectors can be delivered to the leukocytes, each vector in the library expressing one or more RNAs targeted to a gene in a genome of the leukocytes, and wherein the library comprises at least one vector expressing an RNA targeted to each gene in the genome of the leukocytes. The library comprises vectors expressing two, three, four, five or six or more RNAs targeted to each gene in the genome of the leukocytes. In an embodiment wherein one or more RNAs guide the Cas9 to activate or inhibit expression of a target gene, the Cas9 is preferably a non-cutting enzyme, e.g. the Cas9 may be a mutant Cas9 lacking nuclease activity fused to a functional domain that activates or inhibits gene expression.

The invention further comprehends a method for modeling an aberrant leukocyte response or a disease associated with leukocytes, comprising delivering to leukocytes a vector containing nucleic acid molecule(s), whereby the leukocytes contain or express or are able to be induced to express or conditionally express Cas9 and the vector expresses one or more RNAs (i) to guide the Cas9 to introduce mutations in one or more target genetic loci in the leukocytes or (ii) to guide the Cas9 to activate or inhibit expression of a target gene, thereby modulating expression of one or more genes expressed in the leukocytes, and wherein expression of the one or more genes is associated with the response or disease. The leukocytes can be derived from a non-human transgenic animal having cells that contain or express or are able to be induced to express or conditionally express Cas9, and the vector is delivered to the leukocyte ex vivo. The transgenic non-human animal can be a transgenic mouse having cells that contain or express or are able to be induced to express or conditionally express Cas9. The transgenic mouse having cells that contain or express or are able to be induced to express or conditionally express Cas9 can comprise a mouse that has had a Cas9 transgene knocked into the Rosa26 locus. The aberrant leukocyte response can be deficient or excess activation, differentiation, inhibition, migration, exhaustion, adhesion, or proliferation. The disease is an immune system disorder or cancer. In an embodiment wherein the one or more RNAs guide the Cas9 to activate or inhibit expression of a target gene, the Cas9 is preferably a non-cutting enzyme, e.g. the Cas9 may be a mutant Cas9 lacking nuclease activity fused to a functional domain that activates or inhibits gene expression.

The invention further envisions individualized or personalized treatment of a leukocyte-associated disease in a subject in need of such treatment comprising: (a) delivering to leukocytes ex vivo a vector containing nucleic acid molecule(s), whereby the leukocytes contain or express or are able to be induced to express or conditionally express Cas9 and the vector expresses one or more RNAs (i) to guide the Cas9 and optionally delivers one or more donor template(s) to introduce mutations in one or more target genetic loci or (ii) to guide the Cas9 to activate or inhibit expression of a target gene in the leukocytes, thereby modulating expression of one or more genes expressed in the leukocytes; (b) testing treatment(s) for the disease on the leukocytes to which the vector has been delivered; and (c) treating the subject based on results from the testing of treatment(s) of step (b). In one embodiment expression of one or more genes is correlated to the disease. The leukocytes can be derived from a non-human transgenic animal having cells that contain or express or are able to be induced to express or conditionally express Cas9, and the vector is delivered to the leukocyte ex vivo. The disease can be an immune system disorder or cancer.

The invention envisions an isolated leukocyte comprising a vector containing a nucleic acid molecule(s), wherein the leukocyte contains or expresses or is able to be induced to express or conditionally express Cas9 and the vector encodes one or more RNAs capable of (i) guiding the Cas9 and optionally delivering one or more donor template(s) to introduce mutations in one or more target genetic loci or (ii) guiding the Cas9 to activate or inhibit expression of a target gene in the leukocyte, and thereby modulating expression of one or more genes expressed in the leukocyte.

The invention also envisions an isolated leukocyte comprising a vector containing a nucleic acid molecule(s), wherein the leukocyte contains or expresses or is able to be induced to express or conditionally express Cas9, (i) one or more target genetic loci in the leukocyte comprise mutations derived from Cas9 activity guided by one or more RNAs encoded by the vector or (ii) expression of one or more target genes in the leukocytes is activated by Cas9 guided by one or more RNAs encoded by the vector, and wherein expression of one or more genes expressed in the leukocyte is modulated. The RNAs to guide Cas9 can comprise chimeric single guide RNA (sgRNA). Each sgRNA can be driven by a U6 promoter. The vector can be a lentiviral vector, e.g., a U6-sgRNA lentiviral vector. The sgRNAs can target one or more genes expressed in the leukocyte so as to introduce loss-of-function mutations. Gain of function mutations can also be introduced. The leukocyte can be a mammalian leukocyte. The leukocyte can be derived from a non-human transgenic animal having cells that contain or express or are able to be induced to express or conditionally express Cas9. The non-human transgenic animal having cells that contain or express or are able to be induced to express or conditionally express Cas9 can be a mammal or a primate, or a rodent, or a mouse, or a rat or a rabbit, or a canine or dog, or a cow or bovine, or a sheep or ovine or a goat or a pig, or fowl or poultry, or a chicken, or a fish, e.g., a mouse leukocyte. The mouse leukocyte can be from a transgenic mouse having cells that contain or express or are able to be induced to express or conditionally express Cas9. The transgenic mouse having cells that contain or express or are able to be induced to express or conditionally express Cas9 can comprise a mouse that has had a Cas9 transgene knocked into the Rosa26 locus. The leukocyte can be a dendritic cell. The leukocyte can be a T cell. The one or more genes can be associated with a leukocyte response or a leukocyte-associated disease.

The invention also envisions a non-human transgenic eukaryote or mammal having leukocytes that express or that are able to be induced to express or that conditionally express Cas9, and one or more mutation(s) in one or more gene(s) associated with a leukocyte response or a leukocyte-associated disease.

In some methods, it will be appreciated that the invention also provides a method of monitoring an immune response in a subject comprising detecting a level of expression, activity and/or function of Olfr994, Olfr806, Olfr470, or Olfr394. or any one of the foregoing or any combination thereof. In another aspect, the invention provides a method of detecting Olfr994, Olfr806, Olfr470, or Olfr394 in any combination of thereof at a first time point, or detecting a level of expression, activity and/or function of one or more signature genes or one or more products of Olfr994, Olfr806, Olfr470, or Olfr394 or any one of the foregoing or any combination thereof and detecting Olfr994, Olfr806, Olfr470, or Olfr394 or any one of the foregoing or any combination thereof at a second time point, and comparing the first detected level of expression, activity and/or function with the second detected level of expression, activity and/or function, wherein a change in the first and second detected levels indicates a change in the immune response in the subject.

In another aspect, the invention provides for modulating an immune response by treatment with ligands for olfactory receptors. In preferred embodiments, the olfactory receptors may be Olfr994, Olfr806, Olfr470, or Olfr394. An immune response may be activated or repressed by using ligands specific for positive or negative receptors. In one embodiment, the immune response is modulated by smell. Not being bound by a theory, different smells will activate different olfactory receptors and will result in different immune responses.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U. S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12 shows flow cytometry and bin selection in three CRISPR screens done in mouse primary dendritic cells. After 9 days of differentiation and expansion, the cells were 1) Stimulated with LPS for 8 hours and stained for TNF-α. 2) Stimulated with LPS for 24 hours and stained for CD86. 3) Stimulated with LPS and IL-10 for 24 hours and stained for CD-86.

FIG. 18A-E A Genome wide pooled CRISPR screen in mouse primary DC. (A) Single gene CRISPR knockout of known regulators of the LPS response in primary DCs affects Tnf expression. Shown are flow cytometry measurements of intracellular Tnf following 8 h of LPS stimulation in BMDCs with sgRNAs targeting the positive regulators Tlr4 (black) and Myd88 (blue), the negative regulator Zfp36 (red) and a non-targeting control sgRNA (grey). (B) Experimental design for a genome wide CRISPR screen to identify regulators of the LPS response in primary mouse BMDCs. From left: Primary cells from Cas9 transgenic mice were grown for 2 days and then infected with a genome-wide library of lentiviruses containing 6 sgRNAs per mouse gene. Following another 7 days, mature infected BMDCs were stimulated with LPS for 8 hours, stained for intra-cellular Tnf, and sorted by Fluorescence Activated Cell Sorting (FACS) into cells that failed to express Tnf ($Tnf^{lo}$) or that express Tnf most strongly ($Tnf^{hi}$). sgRNAs expressed in the Input library (Input), the cells at day 9 just prior to LPS stimulation (Pre-LPS), and in the $Tnf^{lo}$ and $Tnf^{hi}$ cells were all detected by deep sequencing (thick grey arrows). (C) sgRNAs targeting essential genes are significantly underrepresented in the 'Pre-LPS' versus "Input' sample. Applicants averaged the sgRNA Z-scores of the ratio Input/Pre-LPS for the top four sgRNAs that target the same gene (Experimental Procedures). Shown are cumulative distribution function (CDF) plots of the gene level Z-score distribution of 'all genes' detected (grey), 'all essential' (purple) and 'core essential' (black) genes as defined in (Hart et al., 2014), and all genes associated with the Gene Ontology annotation 'Translation' (blue). (D) sgRNAs targeting known positive and negative regulators are significantly over- and underrepresented, respectively, in '$Tnf^{lo}$' versus '$Tnf^{hi}$' bins. Left: Shown are the binned Z-scores of the '$Tnf^{lo}$'/'$Tnf^{hi}$' ratios (y-axis) versus sgRNA mean abundances (x-axis, mean abundance of sgRNA in '$Tnf^{lo}$' and '$Tnf^{hi}$'). Right: Gene score distribution for positive and negative regulators. For positive (negative) regulators, the Z-scores of the top (bottom) 4 sgRNAs per gene were averaged. (E) Known regulators of the TLR4 pathway rank highly in the screen. Shown are cumulative distribution functions (CDFs) for the rank (in $Tnf^{lo}$ vs. $Tnf^{hi}$, X axis) of the genes in the genome wide CRISPR screen. Shown are CDFs for the 35 genes in the TLR pathway (as defined by KEGG) that directly link LPS and Tnf (blue curve), all non-targeting controls (black curve) and all other genes got ranked in the screen (grey curve).

FIG. 19A-E Individual sgRNA verify dozens of top hits from the pooled screen. (A) Experimental design. From left: Primary cells isolated from Cas9 transgenic mice were grown in GM-CSF for two days and then infected with lentiviruses containing a single sgRNA at high MOI (454 individual sgRNAs tested). At day 6, puromycin was added to select against non-infected cells and at day 9 the derived DCs were stimulated with LPS for 8 h, and Tnf levels were assayed by staining and flow cytometry (blue) and compared to those in DCs infected with control sgRNAs (non-targeting, black). The numbers of tested and verified positive and negative candidate regulators are presented. Negative regulators were tested with saturating (100%) and—in some cases (numbers in parenthesis) with low (20%)—LPS concentrations. (B) Most components of the core TLR pathway are identified by the screen and validated by the individual assay. Left: Shown are all components of the TLR pathway as defined by KEGG that directly link LPS and Tnf, and their rank in the genome wide CRISPR screen (blue scale). Right: Flow cytometry staining of intracellular Tnf for each targeted gene (blue) compared to sgRNA controls (black). (C, D) Many of the top hits for positive regulators are validated individually. (C) The intracellular Tnf signal (sgRNA Z-score relative to the non-targeting sgRNA; Y axis) of the top potential positive regulators (right) and non-targeting controls (left). Validated hits are in blue. (D) Good agreement between scores in the pooled screen and individual validations. Mean Tnf Z score for all sgRNAs targeting the same gene is shown as a function of the ranking (x-axis, based on positive regulators Z score). (E) Theoretical and empirical false discovery rates (FDR) are in good agreement. Shown are the theoretical calculated FDR (Y axis), based on shuffling the guides before collapsing to genes (background), at different ranks in the screen (X axis). Blue curve: empirically true positives determined experimentally in the top 100 ranked positive regulators.

FIG. 20A-F The validated positive regulators partition into key modules based on their effect on four protein markers and RNA expression profiles. (A) Positive regulators are grouped by distinct effects on protein expression. For each positive regulator (rows) shown are its effects (blue: significantly reduces; red: significantly increases; Experimental Procedures) on the expression of each of five proteins (columns) measured by staining with antibodies (Experimental Procedures). Based on this matrix, three broad categories of responses can be defined, each preferentially associated with distinct proteins (color bar on left: turquoise: known LPS response genes; purple: members of the OSTc; petrol blue: members of the PAFc). (B) Effects of key regulator groups on protein markers. For each marker (X axis), shown are two Violin plots of the distribution of Z scores of true positive regulators of Tnf (left) or of non-targeting control sgRNAs (right). Key functional groups are colored as in (A). (C) Example effects of members of the three categories on protein expression. Each distribution shows the expression level of a protein marker (noted on the bottom) in cells with sgRNAs targeting a given positive regulators (colored distribution; top: Myd88; middle: Dad1; bottom: Ctr9) or each of two non-targeting sgRNAs (black). (D-F) Positive regulators partition to modules based on their effect on mRNA profiles over time. Shown are clustered correlation matrix of verified positive regulators (rows, columns) based on global RNA expression profiles in cells where the regulator is targeted relative to non-targeting control (Experimental Procedures). Data from each time point is analyzed and clustered separately ((D) t=0; (E) t=2 h and (F) t=4 h). Genes in 3 key categories are color coded as in (A). Color bar is the Pearson correlation coefficient.

FIG. 22A-J The Paf complex strongly affects the LPS response. (A,B) PAFc component knockout reduced Tnf expression. Shown are flow cytometry stainings of intracellular Tnf from cells with sgRNAs targeting Paf1 (A) or Rtf1 (B) (blue), compared to sgRNA controls (black). (C-F) Knockout of PAFc members affects mainly the antiviral response, while knockout of OSTc members mainly affects the inflammatory response. Shown are violin plots of the distribution of response scores per sgRNA (Y axis, calculated as a linear combination of all RNA changes relative to non-targeting controls) in cells treated with sgRNAs targeting (from left to right) known regulators (brown), non-targeting controls (yellow), OSTc members (light grey: Rpn1, Rpn2, Dad1, Ddost), and PAFc members (dark grey: Paf1, Ctr9, Leo1, Wdr61) for each of 3 response modules: anti-viral (C, 4 h post LPS), sustained inflammatory (D, 4 h post LPS), and peaked inflammatory (E, 2 h post LPS), as well as the Tnf transcript (F, 2 h post LPS). A score of 0 reflects a similar response as in non-targeting controls. Positive and negative values indicate an increased and reduced response, respectively. (G, H) Immunopurification (IP) followed by LC-MS/MS to identify Paf1 or $Rtf_1$ interactors. Scatter plot of two independent IPs for Paf1 (G) or $Rtf_1$ (H). Shown are the log 2 ratios of the Paf1 or $Rtf_1$ IP relative to a control IP. Blue dots indicate interactors that have been tested by individual sgRNA experiments for an effect on Tnf expression, with the IP target (Paf1 or $Rtf_1$) marked in bold. Blue dots with black borders in G indicate previously known PAFc members. (I, J) Knockout of new interactors shows effect on Tnf expression. Shown are flow cytometry stainings of intracellular Tnf from cells with sgRNAs targeting Auh (I, new Paf1 interactor) or Irf4 (J, new $Rtf_1$ interactor) (blue), compared to sgRNA controls (black).

FIG. 27A-E The PAFc module. (A-D) Each panel shows flow cytometry staining of either intracellular Tnf levels (A, B, D; X axis) or Cd11c levels (C, X axis) for each targeted gene (colored histogram; gene name in top left corner) compared to sgRNA controls (black curves). (E) Validation of Paf1 and Auh interaction by Western blot. Shown are the immunopurifications (IPs) in BMDCs performed with either Paf1 antibody (PAF) or IgG antibody (Control). Input or IP samples were incubated with either Paf1 antibody (top) or Auh antibody (bottom). IPs were performed in unstimulated BMDCs (LPS "−") or in BMDCs stimulated with LPS for 2 h (LPS "+").

FIG. 28A-E Assessing false negatives and true positives in individual validation experiments. Each panel shows flow cytometry staining of intracellular Tnf levels (X axis) for each targeted gene (colored histogram; gene name in top left corner) compared to sgRNA controls (black curves). (A, B) Determining the false negative rate. Known regulators of the LPS response that did not rank within the top-100 in the screen were tested individually by single sgRNAs followed by Tnf staining and flow cytometry (see FIG. 2A). (A) 8 tested genes did influence Tnf expression and are considered false negatives. (B) 6 tested genes did not influence Tnf expression and are considered true negatives. (C-E) Sensitive validation of novel negative regulators requires screening at unsaturated levels of Tnf. BMDCs transduced with single sgRNAs targeting candidate negative regulators from the screen, and stained with anti-Tnf antibody after stimulation with either (C) 100 ng/mL LPS (two different sgRNAs shown for each gene) or (D) 20 ng/mL LPS (single sgRNA shown for each gene). (E) BMDC transduced with an sgRNA targeting Stat5b were stained with Cd11c antibody.

FIG. 30A-C Mutation analysis of sequencing sorted mutants. BMDCs were transduced with sgRNA targeting the indicated gene ((A) Paf1, (B) Dad1 and (C) Cd14; marked on top), stimulated with LPS, and flow-sorted based on high or low Tnf antibody staining. Genomic DNA was isolated from sorted cells ("low Tnf" and "high Tnf"), unsorted cells ("Pre-sort"), and cells without relevant sgRNA (control;

only in A and C). The region surrounding the sgRNA target site was amplified and sequenced to analyze mutational composition of the targeted locus.

Figure 31:
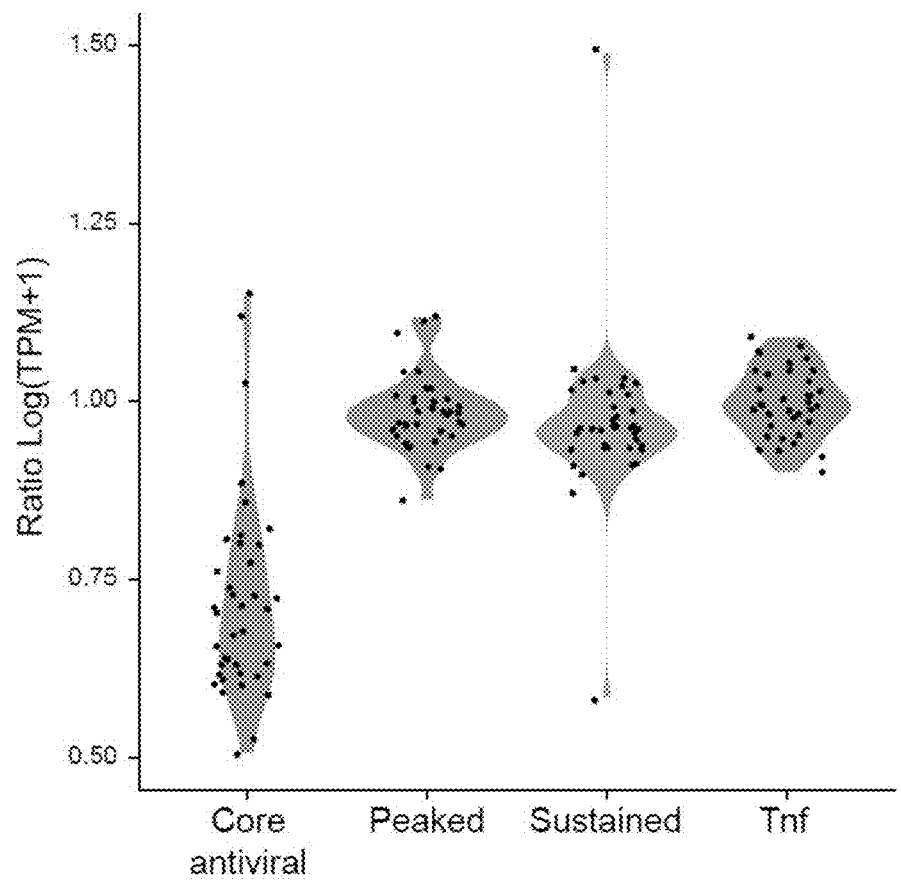

FIG. 31 Effect of Brefeldin on the expression of the different modules. Violin plots show for each validated regulator (dot) the ratio of expression values (log(TPM+)) when comparing between Brefeldin vs. no Brefeldin conditions, in each of 3 modules and TNF (X axis).

The figures herein are for illustrative purposes only and are not necessarily drawn to scale.

DETAILED DESCRIPTION OF THE INVENTION

There are currently two major strategies for associating targets with their putative regulators on a genomic scale (reviewed in (Kim et al., 2009)): (1) observational (correlative) approaches that relate them based on statistical dependencies in their quantities or physical associations; and (2) perturbational (causal) approaches, that relate them by the effect that a perturbation in a putative regulator has on its target.

In an aspect of the invention, Applicants adapt the CRISPR-Cas9 technology to develop a marker based genome-wide knockout screen in primary mammalian cells derived from Cas9-expressing transgenic mice, and applied it to dissect gene regulatory circuits in the response of DCs to LPS. In an aspect of the invention, Applicants infect DCs with a pooled, genome-wide library of lentiviruses, stimulate them with LPS, and monitor their responses by intracellular staining for the inflammatory cytokine TNF, a major marker of the early response to LPS.

In a further aspect, Applicants use Fluorescence Activated Cell Sorting (FACS) to isolate cells that failed to respond to LPS (i.e., caused by a loss-of-function mutation in a positive regulator) or that responded more strongly (i.e., caused by a loss-of-function mutation in a negative regulator), and determine their resident sgRNAs by deep sequencing. Many of the key known regulators of TLR signaling are recovered as the highest regulators in the screen. In a further aspect, Applicants analyze each of 57 validated positive regulators by their effect on four additional protein markers reflecting different aspects of DC biology, and on genome wide expression profiles at four time points post LPS, identify 3 key functional modules, each with a distinct regulatory effect. These modules allow one to relate new regulators to their functions by a guilt-by-functional-association approach, as well as highlight novel distinctive functions in the response. These include roles for the members of the PAF complex, involved in RNA transcription and processing, and of the OST complex important for protein glycosylation. Applicants identify new facets in the complex response of immune cells to pathogens, and provide a general strategy for systematically dissecting circuits in other primary mammalian cells.

In an aspect of the invention, Applicants provide a new method to investigate modules and factors in immune pathways applicable across diverse biological systems. In a further aspect of the invention, the methods provided are coupled with advances in single cell profiling that bridge the gap between genome-wide pooled screens and deep molecular readouts.

With respect to single cell genomic readouts, methods such as Drop-Seq may be employed. Drop-seq is a method which enables highly parallel analysis of individual cells by RNA-seq. Specifically, the RNA content of tens and hundreds of thousands of individual human cells are profiled quickly and inexpensively. In an embodiment of Drop-Seq, special microfluidic devices are used to encapsulate each cell in an individual drop, associate the RNA of each cell with a 'cell barcode' unique to that cell/drop, measure the expression level of each RNA with sequencing, and then use the cell barcodes to determine which cell each RNA molecule came from. (Macosko et al., 2015, Cell 161, 1202-1214)

Currently, techniques or instruments for single molecule or single cell analysis exist (e.g., digital polymerase chain reactions (PCR) or Fluidigm C1, respectively), however none currently allow a scalable method for dynamically delivering reagents and/or appending molecular "information" to individual reactions such that a large population of reactions/assays can be processed and analyzed en masse while still maintaining the ability to partition results by individual reactions/assays. It is an aspect of the present invention to provide a method to screen pathways and modules of interest in systems such as immune diseases coupled to current advances in Drop-Seq methodology.

In a further aspect, Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. (Klein et al., 2015, Cell 161, 1187-1201).

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213, 991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

- Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15;339(6121): 819-23 (2013);
- RNA-guided editing of bacterial genomes using CRISPR-Cas systems. Jiang W., Bikard D., Cox D., Zhang F, Marraffini L A. Nat Biotechnol March;31(3):233-9 (2013);
- One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9;153(4):910-8 (2013);
- Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22;500(7463):472-6. doi: 10.1038/Nature12466. Epub 2013 Aug. 23 (2013);
- Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);
- DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);
- Genome engineering using the CRISPR-Cas9 system. Ran, F A., Hsu, P D., Wright, J., Agarwala, V., Scott, D A., Zhang, F. Nature Protocols November;8(11):2281-308 (2013-B);
- Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];
- Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);
- Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);
- CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);
- Development and Applications of CRISPR-Cas9 for Genome Engineering, Hsu P D, Lander E S, Zhang F., Cell. June 5;157(6):1262-78 (2014).
- Genetic screens in human cells using the CRISPR/Cas9 system, Wang T, Wei J J, Sabatini D M, Lander E S., Science. January 3; 343(6166): 80-84. doi:10.1126/science.1246981 (2014);
- Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December;32(12):1262-7 (2014);
- In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January;33(1):102-6 (2015);
- Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29;517(7536):583-8 (2015).
- A split-Cas9 architecture for inducible genome editing and transcription modulation, Zetsche B, Volz S E, Zhang F., (published online 2 Feb. 2015) Nat Biotechnol. February;33(2):139-42 (2015);
- Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and
- In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9;520 (7546):186-91 (2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)—associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. In some embodiments, the target sequence is comprised in a gene expressed in leukocytes, particularly a gene associated with leukocyte responses or a leukocyte-associated disease. In some embodiments, a guide sequence is selected to reduce the degree of secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechnology* 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataa ggcttcatgccgaaat-caacaccctgtcattttatggcagggtgttttcgttatttaaTTTTTT (SEQ ID NO: 1); (2) NNNNNNNNNNNNNNNNNNNNgttttgtactctcaGAAAtg cagaagctacaaagataaggcttcatgccg aaatcaacaccctgtcattt-tatggcagggtgttttcgttatttaaTTTTTT (SEQ ID NO: 2); (3) NNNNNNNNNNNNNNNNNNNNgttttgtactctcaGAAAtg cagaagctacaaagataaggcttcatgccg aaatcaacaccctgtcattt-tatggcagggtgtTTTTTT (SEQ ID NO: 3); (4) NNNNNNNNNNNNNNNNNNNNgttt-tagagctaGAAAtagcaagttaaaataaggctagtccgttatcaactt gaaaaagtggcaccgagtcggtgcTTTTTT (SEQ ID NO: 4); (5) NNNNNNNNNNNNNNNNNNNNgttt-tagagctaGAAATAGcaagttaaaataaggctagtccgttatcaac ttgaaaaagtgTTTTTTT (SEQ ID NO: 5); and (6) NNNNNNNNNNNNNNNNNNNNgttt-tagagctagAAATAGcaagttaaaataaggctagtccgttatcaTT TTTTTT (SEQ ID NO: 6). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 7) in the EMX1 gene of the human genome, deep sequencing can be used to assess the level of modification at the following two off-target loci, 1: 5'-GAGTCCTAGCAGGAGAAGAA-3' (SEQ ID NO: 8) and 2: 5'-GAGTCTAAGCAGAAGAAGAA-3' (SEQ ID NO: 9). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S. pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 10); the NLS from nucleoplasmin (e.g. the nucleoplasmin bipartite NLS with the sequence KRPAATKKAGQAKKKK (SEQ ID NO: 11)); the c-myc NLS having the amino acid sequence PAAKRVKLD (SEQ ID NO: 12) or RQRRNELKRSP (SEQ ID NO: 13); the hRNPA1 M9 NLS having the sequence NQSSNFGPMKGGNFG-GRSSGPYGGGGQYFAKPRNQGGY (SEQ ID NO: 14); the sequence RMRIZFKNKGKDTAELRRRRVEVS-VELRKAKKDEQILKRRNV (SEQ ID NO: 15) of the IBB domain from importin-alpha; the sequences VSRKRPRP (SEQ ID NO: 16) and PPKKARED (SEQ ID NO: 17) of the myoma T protein; the sequence PQPKKKPL (SEQ ID NO: 18) of human p53; the sequence SALIKKKKKMAP (SEQ ID NO: 19) of mouse c-abl IV; the sequences DRLRR (SEQ ID NO: 20) and PKQKKRK (SEQ ID NO: 21) of the influenza virus NS1; the sequence RKLKKKIKKL (SEQ ID NO: 22) of the Hepatitis virus delta antigen; the sequence REKKKFLKRR (SEQ ID NO: 23) of the mouse Mx1 protein; the sequence KRKGDEVDGVDEVAKKKSKK (SEQ ID NO: 24) of the human poly(ADP-ribose) polymerase; and the sequence RKCLQAGMNLEARKTKK (SEQ ID NO: 25) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+ guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, gene screening, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used to modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control or regulatory sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination of an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a leukocyte, which may be in vivo, ex vivo or in vitro. In some embodiments, the method comprises sampling a leukocyte or population of leukocytes from a human or non-human animal, and modifying the leukocytes. Culturing may occur at any stage ex vivo. The leukocytes may even be re-introduced into the non-human animal or mammal.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

Transgenic non-human eukaryotic organisms, e.g., animals are also provided in an aspect of practice of the instant invention. Preferred examples include animals comprising Cas9, in terms of polynucleotides encoding Cas9 or the protein itself. In certain aspects, the invention involves a constitutive or conditional or inducible Cas9 non-human eukaryotic organism, such as an animal, e.g., a primate, rodent, e.g., mouse, rat and rabbit, are preferred; and can include a canine or dog, livestock (cow/bovine, sheep/ovine, goat or pig), fish, fowl or poultry, e.g., chicken with it mentioned that it is advantageous if the animal is a model as to a human or animal genetic disease or condition, such as a disease associated with leukocytes, as use of the non-human eukaryotic organisms in genetic disease or condition modeling, e.g., via inducing a plurality, e.g., 1 or more, e.g., a plurality or multiple, such as 3 or more, e.g., 3 to 50 mutations correlated or associated with a genetic disease or condition, such as a disease associated with leukocytes, are preferred. To generate transgenic mice with the constructs, as exemplified herein one may inject pure, linear DNA into the pronucleus of a zygote from a pseudo pregnant female, e.g. a CB56 female. Founders may then be identified, genotyped, and backcrossed to CB57 mice. The constructs may then be cloned and optionally verified, for instance by Sanger sequencing. Knock ins are envisaged (alone or in combination). Example 1 provides a knockin Cas9 mouse and to generate a Cas9 knock in mice one may target the same constitutive and conditional constructs to the Rosa26 locus, reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. In a particular embodiment Applicants disclose herein a novel in vivo CRISPR approach with a combination of novel Cas9 reagents, as well as demonstrate application in modeling the dynamics of leukocyte responses such as activation and differentiation; and, that this system can be used to model three and even more than three genetic mutations, such as any number between three (3) and thirty (30) or more. And, this can include modeling in post-mitotic cells. In 293 cells the Cas9 conditional expression construct can be activated by co-expression with Cre. Correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. The conditional Cas9 mouse can be crossed with a mouse that ubiquitously expresses Cre (ACTB-Cre line) and may arrive at a mouse that expresses Cas9 in every cell. The delivery of RNA(s) to guide Cas9, e.g. CRISPR RNA and transactivating (tracr) RNA or a single guide RNA (sgRNA) (chimeric RNA) can induce genome editing in embryonic or adult mice. Interestingly, when the conditional Cas9 mouse is crossed with a mouse expressing Cre under a tissue specific promoter, there should only be Cas9 in the tissues that also express Cre. This approach may be used to edit the genome in only precise tissues (e.g. in leukocytes) by delivering chimeric RNA to the same tissue. Further, the conditional Cas9 mouse is broadly applicable for many areas of biology and its uses as described herein provides many utilities. More generally, while Cas9 provides an effective way to model multiple genetic changes, Cas9 delivery has challenges, including limitations due to the significant size of Cas9, and possible extra biosafety practices. The Cas9 transgenic eukaryote, e.g., mouse provides a most effective method for modeling of aberrant leukocyte responses, leukocyte-associated diseases and other areas of tissue-specific biological studies. Applicants' approach provides a substantial packaging capacity for both sgRNAs as well as reporters and other modulators, etc. These features include efficient editing of cellular subtypes (e.g. leukocyte subtypes) using Cre driver lines, hard to transfect/transduce primary cells (especially primary leukocytes), and delivery of sgRNA using viral or non-viral, nanotechnology-based methods. Applicants used a U6-sgRNA lentiviral vector in their study disclosed herein in Example 2.

Accordingly, the invention involves a non-human eukaryote, animal, mammal, primate, rodent, etc or leukocyte thereof that may be used as a disease model or a model of aberrant leukocyte responses. As used herein, "disease" refers to a disease, disorder, or indication in a subject. For example, a method of the invention may be used to create a non-human eukaryote, e.g., an animal, mammal, primate, rodent or leukocyte that comprises a modification, e.g., 3-50 or more modifications, in one or more nucleic acid sequences associated or correlated with a leukocyte response or disease, e.g., a leukocyte associated disease. Such a mutated nucleic acid sequence may be associated or correlated with a disease or expressed in leukocytes and may encode a disease associated protein sequence or may be a disease associated or correlated control sequence. The leukocyte may be in vivo or ex vivo. In the instance where the leukocyte is in culture, a cell line may be established if appropriate culturing conditions are met and preferably if the cell is suitably adapted for this purpose (for instance a stem cell). Hence, cell lines are also envisaged. In some methods, the model can be used to study the effects of mutations on the animal or leukocyte and the leukocyte response, as well as development and/or progression of the disease using measures commonly used in the study of the disease. Alternatively, such a model is useful for studying the effect of a putatively pharmaceutically active compound or gene therapy on the disease or leukocyte response. A response- or disease-associated gene or polynucleotide can be modified to give rise to the aberrant response or disease in the model, and then putatively pharmaceutically active compound and/or gene therapy can be administered so as to observe whether the response or disease development and/or progression is inhibited or reduced. In particular, the method comprises modifying so as to produce, one or more, advantageously 3-50 or more response- or disease-associated or correlated gene(s) or polynucleotide(s). Accordingly, in some methods, a genetically modified animal or leukocyte may be compared with an animal predisposed to development of the disease, such that administering putative gene therapy, or pharmaceutically acceptable compound(s), or any combination thereof can be performed to assess how such putative therapy(ies) or treatment(s) may perform in a human. The invention can involve contacting a test compound with a leukocyte or administering to a eukaryote a test compound, wherein the eukaryote or leukocyte comprises one or more, e.g., 3-50 or more mutations from the CRISPR-Cas system, e.g., in an animal that expresses Cas9 and to which RNA(s) generating the mutations has/have been administered; and detecting a reduction or an augmentation of a cell signaling event associated with the mutation(s) or lack thereof. Screening of such putative pharmaceutically active compound(s) and/or gene therapy(ies) can be by cellular function change and/or intracellular signaling or extracellular signaling or change in intracellular expression or change in expression of protein on the cell surface. Such screening can involve evaluating for dosages or dose curves, as well as combinations of potential drugs and/or therapies. An altered expression of one or more genome sequences associated with a signaling biochemical pathway can be determined by assaying for a difference in the mRNA levels of the corresponding genes between the disease model eukaryote or animal or leukocyte thereof and a normal eukaryote, animal, or leukocyte, and to ascertain whether when the disease model is administered or contacted with a candidate chemical agent or gene therapy it reverts to or towards normal. An assay can be for mutation(s)-induced alteration in the level of mRNA transcripts or corresponding polynucleotides or polypeptides in comparison with such level(s) in a normal eukaryote or animal and whether such level(s) are placed towards or to normal when a therapy or treatment or agent is employed. Accordingly, the invention comprehends delivery of multiple RNA(s), e.g., sgRNA(s), e.g., 3-50 or more, e.g., 3, 16, 32, 48, 50 or more to the transgenic Cas9 eukaryote and thereafter screening cells, tissue, tumors or the eukaryote for fibers or formation of fibers (with it understood that "eukaryote" is as herein discussed to include animal, mammal, etc). Inducing multiple mutations also enables the skilled person to divine new combinations of mutations that give rise to aberrant leukocyte responses or diseases associated with leukocytes such as immune system disorders or cancer. The ability to induce multiple mutations that accelerate or change the rate of a leukocyte-associated disease, e.g., an immune system disorder or cancer accordingly provides many advantages heretofore unknown in research and development of pharmaceuticals, therapies and treatments for such disorders.

In an aspect the invention can involve leukocytes, e.g., non-human, e.g., animal, such as mammal, e.g., primate, rodent, mouse, rat, rabbit, etc., or even human leukocytes, transformed to contain Cas9, e.g., by a vector that contains nucleic acid molecule(s) encoding a Cas9, e.g., with nucleic acid(s) encoding a promoter and at least one NLS, advantageously two or more NLSs, or leukocytes that have had their genome altered, e.g., through the vector being an integrating virus or through such leukocytes being stem cells or cells that give rise to a cell line or a living organism (but wherein such an organism is advantageously non-human), that contains and expresses nucleic acid molecule(s) encoding Cas9. Such leukocytes are then transplanted into or onto an animal suitable for being a leukocyte-associated disease, e.g., immune system or cancer, model, e.g., fish, a rodent such as a mouse, chickens or chicken embryo or chicken embryo membrane. The leukocytes proliferate on or in the non-human eukaryote, e.g., animal model. The non-human eukaryote, e.g., animal model, having the proliferated heterologous transplanted Cas9-containing cells, is then administered RNA(s) or vector(s), e.g., AAV, adenovirus, lentivirus containing or providing RNA(s), e.g., under the control of a promoter such as a U6 promoter and/or particle(s) and/or nanoparticle(s) containing the RNA(s) and/or vector(s), whereby the RNA(s) direct the Cas9 in the cells to provide mutation, e.g., a plurality of mutation(s) such as from 3 to 30 mutations, advantageously mutation(s) associated or correlated with a leukocyte-associated disease, whereby the non-human eukaryote, e.g., animal model is transformed into being a non-human eukaryote, e.g., animal model for the leukocyte-associated disease. The non-human eukaryote, e.g., animal model can then be used for testing, e.g., as to potential therapy and/or putative treatment via a possibly pharmaceutically active compound. The administering can be at or to or for body delivery to the proliferated heterologous transplanted Cas9-containing leukocytes, e.g., direct injection at or near such proliferated heterologous transplanted Cas9-containing leukocytes, or injection or other administration in such a way that the RNA(s) are delivered into the proliferated heterologous transplanted Cas9-containing leukocytes, e.g., injection into the bloodstream whereby bodily functions transport to the proliferated heterologous transplanted Cas9-containing leukocytes. In an aspect of the invention, barcoding techniques of WO/2013/138585 A1 can be adapted or integrated into the practice of the invention. WO/2013/138585 A1 provides methods for simultaneously determining the effect of a test condition on viability or proliferation of each of a plurality of genetically heterogeneous cell types. The methods include: providing a unitary sample comprising a plurality of, e.g., five, ten, twenty, twenty-five, or more, genetically heterogeneous cell types (each individual cell type is genetically homogeneous within itself, but differs from the others in the plurality), wherein each cell type further comprises: (i) an exogenous nucleic acid tag stably integrated into the genome of the cells, e.g., a tag comprising a core sequence that is unique to each cell type, and flanking amplification primer binding sequences that are the same in all of the cells of the plurality, and (ii) optionally, a marker, e.g., a selectable or detectable marker; and a known number of cells of each cell type is present in the sample; exposing the sample to a test condition for a selected time; and detecting a level of the exogenous nucleic acid tag in each cell type, wherein the level of the exogenous nucleic acid tag is proportional to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type. WO/2013/138585 A1 also provides methods for simultaneously determining the effect of a test condition on viability or proliferation of each of a plurality of genetically heterogeneous cell types, wherein the methods include providing a unitary sample comprising a plurality of, e.g., five, ten, twenty, twenty-five, or more, genetically heterogeneous cell types, wherein each cell type further comprises: (i) an exogenous nucleic acid tag stably integrated into the genome of the cells, e.g., comprising a core sequence that is unique to each cell type, and flanking amplification primer binding sequences that are the same in all of the cells of the plurality, and (ii) optionally, a selectable or detectable marker; and a known number of cells of each cell type is present in the sample; implanting the sample into a living animal; exposing the sample to a test condition for a selected time; harvesting the sample from the animal; and detecting a level of the exogenous nucleic acid tag in each cell type of the sample, wherein the level of the exogenous nucleic acid tag correlates to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type. The tag can be Cas9 or another TAG or marker that is integrated into the genome of cells to be transplanted into or onto a non-human eukaryote, e.g., animal model, or that is integrated into the genome of the non-human transgenic eukaryote, e.g., animal, mammal, primate, rodent, mouse, rat, rabbit, etc (along with coding for Cas9). The test condition can be the administration or delivery of the RNA(s) to guide the Cas9 to induce one or more or a plurality, e.g., 3-50 or more, mutations. The test condition can be the administration, delivery or contacting with a putative chemical agent treatment and/or gene therapy treatment. The tag can also be the one or more or a plurality, e.g., 3-50 or more mutations, and the test condition can be the administration, delivery or contacting with a putative chemical agent treatment and/or gene therapy treatment.

The invention comprehends delivering the CRISPR-Cas system and/or component(s) thereof to the transgenic non-human eukaryote, e.g., mammal; for instance, to leukocytes of a mammal, e.g., a non-human mammal. In general, delivery of the CRISPR-Cas system and/or component(s) thereof and/or coding for component(s) thereof can be as in WO 2014/093622 (PCT/US2013/074667), with AAV, lentivirus, and adenovirus vectors or particles or nanoparticles (including particle bombardment techniques that can include gold or other elemental, e.g., tungsten particles) preferred, and use thereof in the practice of the invention is within the ambit of the skilled artisan from this disclosure and the knowledge in the art, e.g., WO 2014/093622 (PCT/US2013/074667), incorporated herein by reference. The invention involves at least one component of the CRISPR complex, e.g., RNA, delivered via at least one vector or particle or nanoparticle complex. In some aspects, the invention provides methods comprising delivering one or more polynucleotides, such as or one or more vectors as described herein, one or more transcripts thereof, and/or one or proteins transcribed therefrom, to a host leukocyte. In some aspects, the invention further provides leukocytes produced by such methods, and animals comprising such leukocytes. In some embodiments, a CRISPR enzyme in combination with (and optionally complexed with) a guide sequence is delivered to a leukocyte. Conventional viral and non-viral based gene transfer methods can be used to introduce nucleic acids in mammalian leukocytes. Such methods can be used to administer nucleic acids encoding components of a CRISPR system to leukocytes in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994). Methods of non-viral delivery of nucleic acids include lipofection, microinjection, biolistics, virosomes, liposomes, immunoliposomes, polycation or lipid: nucleic acid conjugates, naked DNA, artificial virions, cell-penetrating peptides and agent-enhanced uptake of DNA. Cell-penetrating peptides are described in, for example, Stalmans et al. PLoS One. 2013; 8(8): e71752 and Milletti et al. (2012), Drug Discov Today 17: 850-860. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to leukocytes in culture (e.g. in vitro or ex vivo administration) or leukocytes in an animal (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat leukocytes in vitro, and the modified leukocytes may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Packaging cells are typically used to form virus particles that are capable of infecting a host cell. Such cells include 293 cells, which package adenovirus, and w2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA. There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep. The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV. In addition to 293 cells, other cells that can be used in the practice of the invention and the relative infectivity of certain AAV serotypes in vitro as to these cells; see Grimm, D. et al, J. Virol. 82: 5887-5911 (2008). The invention provides rAAV that contains or consists essentially of an exogenous nucleic acid molecule encoding a CRISPR (Clustered Regularly Interspaced Short Palindromic Repeats) system or component(s) or coding therefor, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

In some embodiments, a leukocyte transiently transfected with the components of a CRISPR system as described herein (such as by transient transfection of one or more vectors, or transfection with RNA), and modified through the activity of a CRISPR complex, is used to establish a new leukocyte cell line comprising leukocytes containing the modification but lacking any other exogenous sequence. In some embodiments, leukocytes transiently or non-transiently transfected with one or more vectors described herein, or cell lines derived from such cells are used in assessing one or more test compounds.

If a Cas9-expressing model provided for herein is used, then only delivery of guide(s) is necessary. In some embodiments, one or more vectors described herein are used to produce a non-human transgenic Cas9 eukaryote, e.g., animal, mammal, primate, rodent, mouse, rat, rabbit. In some embodiments, the transgenic animal is a mammal, such as a mouse, rat, or rabbit. Guides or RNA(s) can be delivered via the same vector types as Cas9. When both guides or RNA(s) and Cas9 are being delivered a dual-vector system where the Cas9 is delivered via in vivo expression from an AAV vector and the guide(s) are delivered by a separate AAV vector. This can be done substantially contemporaneously (i.e. co-delivery), but it could also be done at separate points in time, separated even by weeks or months. Of course, the ultimate separation is where the transgenic Cas9 eukaryote is generated and thereafter the guide(s) or RNA(s) are delivered. Alternatively a first round of CRISPR-Cas9 systems can be delivered, and subsequently further guides or RNA(s) are delivered as the original Cas9 is still functional in the target cells may be re-used. If the Cas9 is under the control of an inducible promoter, then induction of transcription of new CAs9 in the target cells is preferred.

Aerosolized delivery is preferred for AAV or adenovirus delivery in general. An adenovirus or an AAV particle may be used for delivery. Suitable gene constructs, each operably linked to one or more regulatory sequences, may be cloned into the delivery vector. In this instance, Cbh or EF1a promoter for Cas9, U6 or H1 promoter for chimeric guide RNA may be advantageous. Cas9 and/or RNA(s) can be delivered using particles, adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The vectors can be injected into the tissue of interest. For cell-type specific genome modification, the expression of Cas9 can be driven by a cell-type specific promoter.

Among vectors that may be used in the practice of the invention, integration in the host genome is possible with the retrovirus, lentivirus, and adeno-associated virus gene transfer methods, often resulting in long term expression of the inserted transgene. Additionally, high transduction efficiencies have been observed in many different cell types and target tissues. The tropism of a retrovirus can be altered by incorporating foreign envelope proteins, expanding the potential target population of target cells. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Zou et al. administered about 10 µl of a recombinant lentivirus having a titer of $1\times10^9$ transducing units (TU)/ml by an intrathecal catheter. These sort of dosages can be adapted or extrapolated to use of a retroviral or lentiviral vector in the present invention.

Also useful in the practice of the invention is a minimal non-primate lentiviral vector, such as a lentiviral vector based on the equine infectious anemia virus (EIAV) (see, e.g., Balagaan, J Gene Med 2006; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Intracameral, subretinal, intraocular and intravitreal injections are all within the ambit of the instant invention (see, e.g., Balagaan, J Gene Med 2006; 8: 275-285, Published online 21 Nov. 2005 in Wiley InterScience (www.interscience.wiley.com). DOI: 10.1002/jgm.845). In this regard, mention is made of RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for practice of the present invention. Dosing of RetinoStat® (e.g., $1.1 \times 10^5$ transducing units per eye (TU/eye) in a total volume of 100 µl) can be applied or extrapolated from in practicing the present invention with a lentivirus.

The invention also can be practiced with an adenovirus vector, e.g., an E1-, partial E3-, E4-deleted adenoviral vector may be used in the practice of the invention. Such vectors are safe as twenty-eight patients with advanced neovascular age-related macular degeneration (AMD) were given a single intravitreous injection of an E1-, partial E3-, E4-deleted adenoviral vector expressing human pigment epithelium-derived factor (AdPEDF.11) (see, e.g., Campochiaro et al., Human Gene Therapy 17:167-176 (February 2006)); and previous adenovirus doses ranging from $10^6$ to $10^{9.5}$ particle units (PU) can be adapted to or employed in the practice of the instant invention (see, e.g., Campochiaro et al., Human Gene Therapy 17:167-176 (February 2006)). Adenoviral vector-mediated RNA transfer appears to be a viable approach for delivery of RNA(S). For adenoviral vector injections into a rat, $2 \times 10^9$ infectious particles were injected in 3 ml of normal saline solution (NSS). This can be adapted to or extrapolated from in the practice of the present invention. For siRNA, a rat was injected into the great saphenous vein with 12.5 µg of a siRNA and a primate was injected into the great saphenous vein with 750 µg of a siRNA. This can be adapted to or extrapolated from in the practice of the present invention.

Accordingly, the invention contemplates amongst vector(s) useful in the practice of the invention: viral vectors, including retroviral vectors, lentiviral vectors, adenovirus vectors, or AAV vectors.

Several types of particle and nanoparticle delivery systems and/or formulations are known to be useful in a diverse spectrum of biomedical applications; and particle and nanoparticle delivery systems in the practice of the instant invention can be as in WO 2014/093622 (PCT/US13/74667). In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm. As used herein, a particle delivery system/formulation is defined as any biological delivery system/formulation which includes a particle in accordance with the present invention. A particle in accordance with the present invention is any entity having a greatest dimension (e.g. diameter) of less than 100 microns (µm). In some embodiments, inventive particles have a greatest dimension of less than 10 µm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm. Particle characterization (including e.g., characterizing morphology, dimension, etc.) is done using a variety of different techniques.

Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry(MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants. Doses of about 5 mg/kg are contemplated, with single or multiple doses, depending on the target tissue. It is mentioned herein experiments involving mice involve 20 g mammals and that dosing can be scaled up to a 70 kg human. With regard to nanoparticles that can deliver RNA, see, e.g., Alabi et al., Proc Natl Acad Sci USA. 2013 Aug. 6;110(32): 12881-6; Zhang et al., Adv Mater. 2013 Sep. 6;25(33):4641-5; Jiang et al., Nano Lett. 2013 Mar. 13;13(3):1059-64; Karagiannis et al., ACS Nano. 2012 Oct. 23;6(10):8484-7; Whitehead et al., ACS Nano. 2012 Aug. 28;6(8):6922-9 and Lee et al., Nat Nanotechnol. 2012 Jun. 3;7(6):389-93. Lipid Nanoparticles, Spherical Nucleic Acid (SNA™) constructs, nanoplexes and other nanoparticles (particularly gold nanoparticles) are also contemplate as a means for delivery of CRISPR/Cas system or component(s) thereof or vector(s) to intended targets. Particles, nanoparticles, and the like and vectors are advantageous for delivering the RNA(s) of the CRISPR-Cas9 system and particles and nanoparticles and the like may be advantageous for delivery of vector containing nucleic acid(s) encoding or comprising RNA(s) of the invention. In certain instances, e.g., where Cas9 is constitutively or inducibly or conditionally expressed by an organism or cells thereof, it is useful to deliver the RNA(s) (also herein sometimes termed "guides") of the CRISPR-Cas9 system separately from the Cas9. It is considered as advantageous that the Cas9 may be delivered via a viral vector or be constitutively or inducibly or conditionally expressed and that guides specific to genomic targets are delivered separately. A recent publication, entitled "In vivo endothelial siRNA delivery using polymeric nanoparticles with low molecular weight" by James E. Dahlman and Carmen Barnes et al. Nature Nanotechnology (2014) published online 11 May 2014, doi:10.1038/nnano.2014.84, incorporated herein in its entirety, showed that polymeric nanoparticles made of low-molecular-weight polyamines and lipids can deliver siRNA to endothelial cells with high efficiency, thereby facilitating the simultaneous silencing of multiple endothelial genes in vivo. The authors reported that unlike lipid or lipid-like nanoparticles, the nanoparticle formulation they used (termed 7C1), differed from traditional lipid-based nanoparticle formulations because it can deliver siRNA to lung endothelial cells at low doses without substantially reducing gene expression in pulmonary immune cells, hepatocytes or peritoneal immune cells. Successful in vivo use of a nanoparticle formulation in the context of CRISPR-Cas to achieve functional gene silencing is possible with the 7C1 nanoparticle. The 7C1 nanoparticle can be formulated to mediate delivery of sgRNA to constitutively active Cas9 mouse. Synthesis of the 7C1 nanoparticle is described in Dahlman et al., 2014, Nature Nanotechnology.

Kits: In an aspect, the invention provides kits containing any one or more of the elements discussed herein. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow the provision of all elements of the systems of the invention. Kits can involve vector(s) and/or particle(s) and/or nanoparticle(s) containing or encoding RNA(s) for 3-50 or more mutations to be administered to a non-human transgenic Cas9 eukaryote, e.g., animal, mammal, primate, rodent, etc., with such a kit including instructions for administering to such a eukaryote; and such a kit can optionally include a transgenic Cas9 eukaryote, or when such a transgenic Cas9 eukaryote has Cas9 expression that is inducible or conditional, e.g., Cre-dependent, the kit may also include a mate that expresses the compound that induces or is the trigger or condition for Cas9 expression, e,g, Cre, either throughout all cells or in only certain cells or tissue, whereby offspring of the eukaryotes express of Cas9, e.g., in specific tissues or throughout most or all or nearly all cells, whereby the kit can include instructions for mating and then administering.

Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid -Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed. -Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C.D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| Set | Sub-set | | |
|---|---|---|---|
| Hydrophobic | FWYHKMILVAGC | Aromatic | FWYH |
| | | Aliphatic | ILV |
| Polar | WYHKREDCSTNQ | Charged | HKRED |
| | | Positively charged | HKR |
| | | Negatively charged | ED |
| Small | VCAGSPTND | Tiny | AGS |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as 0), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 26). This may be followed by the loop sequence GAAA as shown. Both of these are preferred examples. Applicants have demonstrated Cas9-mediated indels at the human EMaX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as Escherichia coli, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in Escherichia coli with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion E. coli expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast Saccharomyces cerevisiae include pYepSecl (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in E. coli (Ishino et al., J. Bacteriol., 169:5429-5433 [1987]; and Nakata et al., J. Bacteriol., 171:3553-3556 [1989]), and associated genes. Similar interspersed SSRs have been identified in Haloferax mediterranei, Streptococcus pyogenes, Anabaena, and Mycobacterium tuberculosis (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema, and Thermotoga.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from Arabidopsis thaliana), and a transcriptional activation/repression domain. Further examples of inducible DNA binding proteins and methods for their use are provided in U.S. 61/736, 465 and U.S. 61/721,283, which is hereby incorporated by reference in its entirety.

Embodiments of the present invention involve modulating leukocyte activity, as well as identifying genes associated with leukocyte responses and modeling of aberrant leukocyte activation and diseases associated with leukocytes. In general, the leukocyte(s) may be any subtype or population of leukocytes, e.g. dendritic cells, monocytes, macrophages, lymphocytes (e.g. T cells or B cells or Natural Killer cells), neutrophils, eosinophils, or basophils, or any combination or subgroup of the above. Precursors of mature leukocytes are also encompassed by the term leukocytes, e.g. hematopoietic stem and progenitor cells. Leukocyte subtypes may be identified by characteristic morphology and/or cell surface markers, as is well known in the art.

In some embodiments the leukocyte(s) may comprise a subtype of dendritic cells, monocytes, macrophages, lymphocytes (e.g. T cells or B cells or Natural Killer cells), neutrophils, eosinophils, or basophils, e.g. defined by one or more cell surface markers. In one embodiment, the leukocytes comprise bone marrow-derived dendritic cells (BMDCs). In other embodiments, the leukocytes may comprise helper, cytotoxic, memory and/or regulatory T cells, e.g. CD4+, CD8+, CD45RO+ and/or Foxp3+ T cells.

In embodiments of the present invention, various types of leukocyte response may be modeled or investigated, e.g. depending on the type of leukocyte or subtype thereof. For instance, in some embodiments the leukocyte response may comprise activation, inhibition, migration, exhaustion, adhesion, differentiation and/or proliferation.

In one preferred embodiment, the leukocytes are dendritic cells and the response comprises activation. For instance, dendritic cells may be activated by stimulation with bacterial lipopolysaccharide (LPS). In some embodiments dendritic cell activation may be measured by determining expression of one or more products or cell surface markers associated with dendritic cell activation, e.g. tumor necrosis factor alpha (TNF-α) or CD86. Activation of dendritic cells may be suppressed by anti-inflammatory cytokines such as interleukin-10. Thus stimulation of dendritic cells with LPS in the presence of IL-10 allows the identification of mutations that overcome the suppression of dendritic cell activation by IL-10.

In another preferred embodiment, the leukocytes are T cells and the response comprises differentiation, for instance towards a Th1, Th2, Treg or Th17 phenotype, or maintenance of each phenotype. Differentiation of T cells towards particular phenotypes may be stimulated by specific cytokines. For instance, interleukin-12 (IL-12) may stimulate a Th1 response, whereas interleukin-4 (IL-4) may be used to stimulate a Th2 response. Stimulation with transforming growth factor beta (TGFβ) may induce differentiation towards a Treg response, whereas TGFβ in combination with interleukin-6 (IL-6) may induce a Th17 response. Differentiation towards particular responses may be measured by determining expression of particular markers characteristic of each response type. For instance, interferon-γ (IFN γ) may be measured to indicate a Th1 response, IL-4 may be measured to indicate a Th2 response, TGFβ may be measured to indicate a T reg response and IL-17 may be measured to indicate a Th17 response.

In some embodiments, the T cells are from a transgenic mouse having cells that express Cas9 and an ovalbumin-specific αβ-T cell receptor. Such transgenic mice may be obtained, for example, by crossing Cas9 transgenic mice as described above (e.g. having a Cas9 transgene knocked into the Rosa26 locus) with e.g. OT-II transgenic mice. OT-II transgenic mice express the mouse alpha-chain and beta-chain T cell receptor that pairs with the CD4 coreceptor and is specific for chicken ovalbumin 323-339 in the context of I-A b. In OT-II mice there is a four-fold increase in the CD4 to CD8 peripheral T cell ratio, and lymph node T cells demonstrate a dose-dependent proliferative response to the specific ovalbumin ligand. OT-II mice are described, for example, in Barnden et al. (1998) Defective TCR expression in transgenic mice constructed using cDNA-based alpha- and beta-chain genes under the control of heterologous regulatory elements, Immunol Cell Biol 76(1):34-40, incorporated by reference.

In embodiments of the present invention, a decreased response in a leukocyte is typically indicative that a gene mutated in the leukocyte by delivery of the vector is a positive regulator of the response. For instance, where delivery of the vector introduces one or more loss-of-function mutations into a gene that normally promotes the response, the response is expected to be decreased. Conversely an increased response in a leukocyte is typically indicative that a gene mutated in the leukocyte by delivery of the vector is a negative regulator of the response, i.e. delivery of the vector introduces one or more loss-of-function mutations into a gene expression that normally suppresses the response.

Embodiments of the present invention may involve modeling of any of the above responses, and in particular aberrant leukocyte responses. By aberrant leukocyte responses it is typically meant a leukocyte response that is deficient or excessive, for instance deficient or excess activation, differentiation or proliferation. In particular, where a gene has been identified as being associated with a leukocyte response by the method described above, leukocytes in which that gene is inactivated may be used to model such aberrant responses. For instance, where a gene expressed in dendritic cells is identified as a positive regulator of dendritic cell activation, dendritic cells in which the gene contains one or more loss-of-function mutations may be used as a model of deficient dendritic cell activation. Such a model may be used to identify agents which promote dendritic cell activation, e.g. for use in immunotherapy for cancer.

Further embodiments of the invention may involve modeling diseases associated with leukocytes. By diseases associated with leukocytes it is typically meant any disorder or condition in which leukocytes or a subtype thereof influence the disease pathology, especially conditions where deficient or excessive leukocyte responses are associated with the disease. Leukocyte-associated diseases include, e.g. immune system disorders and cancer. For instance, the disease may be an autoimmune disease, a chronic persistent infection, leukemia, leukopenia or transplant rejection.

Autoimmune diseases involve the generation of an immunogenic response against one or more self tissues or cells. Examples of autoimmune diseases include rheumatoid arthritis, multiple sclerosis, lupus erythematosis, myasthenia gravis, scleroderma, Crohn's disease, ulcerative colitis, Hashimoto's disease, Graves' disease, Sjogren's syndrome, Addison's disease, insulin-dependent diabetes mellitus (IDDM), inflammatory bowel disease and thyroiditis.

Infections may be considered to be chronic and persistent if, for example, the infection persists for at least 3 months, more preferably at least 6 months. Examples of chronic persistent infections include tuberculosis, the hepatitis B, hepatitis C or HIV.

Transplant rejection may be either chronic or acute, including rejection of allogeneic or xenogeneic transplants. The disease may also be graft-versus-host disease, i.e. in which leukocytes from a donor attack cells of a transplant recipient.

Cancer may be defined as a condition involving uncontrolled cell growth. Examples of cancers breast cancer, prostate cancer, colon cancer, lung cancer, ovarian cancer, cervical cancer, gastrointestinal cancer, pancreatic cancer, glioblastoma, liver cancer, bladder cancer, hepatoma, kidney cancer, thyroid cancer, skin cancer, melanoma, brain cancer, neuroblastoma, myeloma, include carcinoma, lymphoma and leukemia.

The models of the present invention may be used to model the aberrant leukocyte responses occurring in such diseases. For instance, excessive leukocyte responses may underlie the pathology in conditions such as autoimmune diseases and transplant rejection. Targeting a negative regulator of leukocyte responses (e.g. the mouse A20 locus in dendritic cells, see Example 2) may serve as a model for such excessive leukocyte responses. In contrast, the suppression of immune responses against tumor antigens is important in the pathogenesis of many types of cancer. Targeting a positive regulator of leukocyte responses (e.g. the mouse MyD88 locus in dendritic cells, see Example 2) may be used to model deficient leukocyte responses in conditions such as cancer.

In some embodiments, the method of the present invention involves delivering a plurality of different vectors, each expressing different guide RNAs, to a plurality of leukocytes. In this way, a plurality of different genes expressed in the leukocytes may be targeted, in order to screen for genes involved in leukocyte responses. Preferably the method may involve delivering at least 100, at least 1000 or at least 10,000 vectors, wherein each vector expresses one or more guide RNAs. For instance, at least 100, at least 1000, at least 10,000 or at least 100,000 guide RNAs may be expressed in the method.

In one embodiment the method involves a genome-wide screen, e.g. in which all genes in the genome of the leukocytes are targeted. For instance, in one embodiment a library of vectors is delivered to the leukocytes, each vector in the library expressing one or more RNAs targeted to a gene in a genome of the leukocytes, and wherein the library comprises at least one vector expressing an RNA targeted to each gene in the genome of the leukocytes. Preferably the library comprises more than one RNA targeted to each gene in the genome, e.g. the library comprises two, three, four, five or six or more RNAs targeted to each gene in the genome. In these embodiments, the library may comprise, for example, at least 10,000, at least 50,000 or at least 100,000 guide RNAs. In one embodiment the library comprises a genome-wide lentiviral sgRNA library as described in Sanjana et al. (2014), Improved vectors and genome-wide libraries for CRISPR screening, Nature Methods 11, 783-784, incorporated herein by reference.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Cas9 transgenic and knock in mice

Reference is made to WO 2014/093622 (PCT/US13/74667), incorporated herein by reference. To generate a mouse that expresses the Cas9 nuclease Applicants submit two general strategies, transgenic and knock in. These strategies may be applied to generate any other model organism of interest, for e.g. Rat. For each of the general strategies Applicants made a constitutively active Cas9 and a Cas9 that is conditionally expressed (Cre recombinase dependent). The constitutively active Cas9 nuclease is expressed in the following context: pCAG-NLS-Cas9-NLS-P2A-EGFP-WPRE-bGHpolyA. pCAG is the promoter, NLS is a nuclear localization signal, P2A is the peptide cleavage sequence, EGFP is enhanced green fluorescent protein, WPRE is the woodchuck hepatitis virus posttranscriptional regulatory element, and bGHpolyA is the bovine growth hormone poly-A signal sequence. The conditional version has one additional stop cassette element, 1oxP-SV40 polyA x3-1oxP, after the promoter and before NLS-Cas9-NLS (i.e. pCAG-1oxP-SV4OpolyAx3-1oxP-NLS-Cas9-NLS-P2A-EGFP-WPRE-bGHpolyA). The constitutive construct should be expressed in all cell types throughout development, whereas, the conditional construct will only allow Cas9 expression when the same cell is expressing the Cre recombinase. This latter version will allow for tissue specific expression of Cas9 when Cre is under the expression of a tissue specific promoter. Moreover, Cas9 expression could be induced in adult mice by putting Cre under the expression of an inducible promoter such as the TET on or off system.

Validation of Cas9 constructs: Each plasmid was functionally validated in three ways: 1) transient transfection in 293 cells followed by confirmation of GFP expression; 2) transient transfection in 293 cells followed by immunofluorescence using an antibody recognizing the P2A sequence; and 3) transient transfection followed by Surveyor nuclease assay. The 293 cells may be 293FT or 293 T cells depending on the cells that are of interest. In a preferred embodiment the cells are 293FT cells. The results of the Surveyor were run out on the top and bottom row of the gel for the conditional and constitutive constructs, respectively. Each was tested in the presence and absence of chimeric RNA targeted to the hEMX1 locus (chimeric RNA hEMX1.1). The results indicate that the construct can successfully target the hEMX1 locus only in the presence of chimeric RNA (and Cre in the conditional case). The gel was quantified and the results are presented as average cutting efficiency and standard deviation for three samples.

Transgenic Cas9 mouse: To generate transgenic mice with constructs, Applicants inject pure, linear DNA into the pronucleus of a zygote from a pseudo pregnant CB56 female. Founders are identified, genotyped, and backcrossed to CB57 mice. The constructs were successfully cloned and verified by Sanger sequencing.

Knock in Cas9 mouse: To generate Cas9 knock in mice Applicants target the same constitutive and conditional constructs to the Rosa26 locus. Applicants did this by cloning each into a Rosa26 targeting vector with the following elements: Rosa26 short homology arm—constitutive/conditional Cas9 expression cassette—pPGK-Neo-Rosa26 long homology arm—pPGK-DTA. pPGK is the promoter for the positive selection marker Neo, which confers resistance to neomycin, a 1 kb short arm, a 4.3 kb long arm, and a negative selection diphtheria toxin (DTA) driven by PGK.

The two constructs were electroporated into R1 mESCs and allowed to grow for 2 days before neomycin selection was applied. Individual colonies that had survived by days 5-7 were picked and grown in individual wells. 5-7 days later the colonies were harvested, half were frozen and the other half were used for genotyping. Genotyping was done by genomic PCR, where one primer annealed within the donor plasmid (AttpF) and the other outside of the short homology arm (Rosa26-R) Of the 22 colonies harvested for the conditional case, 7 were positive (Left). Of the 27 colonies harvested for the constitutive case, zero were positive (Right). It is likely that Cas9 causes some level of toxicity in the mESC and for this reason there were no positive clones. To test this Applicants introduced a Cre expression plasmid into correctly targeted conditional Cas9 cells and found very low toxicity after many days in culture. The reduced copy number of Cas9 in correctly targeted conditional Cas9 cells (1-2 copies per cell) is enough to allow stable expression and relatively no cytotoxicity. Moreover, this data indicates that the Cas9 copy number determines toxicity. After electroporation each cell should get several copies of Cas9 and this is likely why no positive colonies were found in the case of the constitutive Cas9 construct. This provides strong evidence that utilizing a conditional, Cre-dependent strategy should show reduced toxicity. Applicants inject correctly targeted cells into a blastocyst and implant into a female mouse. Chimerics are identified and backcrossed. Founders are identified and genotyped.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

Example 2

Ex vivo genome editing in primary dendritic cells by lentiviral-mediated sgRNA expression To determine whether the Rosa26 knock-in construct provided functional levels of Cas9 expression, Applicants set out to test whether a previously described U6-sgRNA lentiviral vector (Sanjana et al., 2014) could mediate indel formation ex vivo in primary immune cells. Several types of immune cells, such as innate immune dendritic cells (DCs), are often not accessible for genetic manipulation due to delivery challenges, short viability terms in culture, or both. Moreover, since existing cell lines do not mimic DC biology well, many studies are performed with primary cells derived ex vivo from precursors isolated from the bone marrow (BMDCs) (FIG. 1), which retain many critical characteristics of DCs in vivo (Amit et al., 2009; Chevrier et al., 2011; Garber et al., 2012; Shalek et al., 2013). Applicants thus reasoned that Cas9-expressing cells derived from the constitutive Cas9-expressing mice may facilitate such applications, since genome editing would only require introduction of sgRNAs, which can be efficiently delivered using lentiviral vectors.

Methods

Mouse dendritic cells 6-8 week old constitutive Cas9-expressing female mice were used for all DC experiments. Bone marrow cells were collected from femora and tibiae and plated at concentration of $2\times10^5$/ml on non-treated tissue culture dishes in RPMI medium (Gibco, Carlsbad, Calif., Invitrogen, Carlsbad, Calif.), supplemented with 10% FBS (Invitrogen), L-glutamine (Cellgro), penicillin/streptomycin (Cellgro), MEM non-essential amino acids (Cellgro), HEPES (Cellgro), sodium pyruvate (Cellgro), β-mercaptoethanol (Gibco), and GM-CSF (20 ng/mL; Peprotech). SgRNAs targeting Myd88 and A20 were cloned into a guide-only lentiviral vector (Sanjana et al., 2014). At day 2, cells were infected with lentiviruses encoding guide RNAs. Cells were expanded in the presence of GM-CSF. At day 7, infected cells were selected by adding puromycin (Invitrogen) at 5 μg/mL. At day 9, 100 ng/ml LPS (Invivogen) was added 30 min prior to protein analysis or 3 hours prior to mRNA expression profiling. Flow cytometry for GFP detection was performed with BD Accuri C6. Western blot was done using anti-Myd88 (R&D Systems AF3109) and anti-actin (Abcam, ab6276) antibodies.

Nanostring nCounter expression measurement

DCs were processed and analyzed as previously described (Amit et al., 2009). Briefly, $5\times10^4$ cells were lysed in TCL buffer (Qiagen) supplemented with β-mercaptoethanol. 5% of the lysate was hybridized for 16 hours with a previously described Nanostring Gene Expression CodeSet (Geiss et al., 2008) and loaded into the nCounter Prep Station followed by quantification using the nCounter Digital Analyzer. Counts were normalized using control genes as previously described (Amit et al., 2009) and fold changes were calculated relative to cells transduced with sgRNA targeting GFP and non-targeted controls. Heat maps were created using GENE-E (http://www.broadinstitute.org/cancer/software/GENE-E/).

Results

Figure 1:
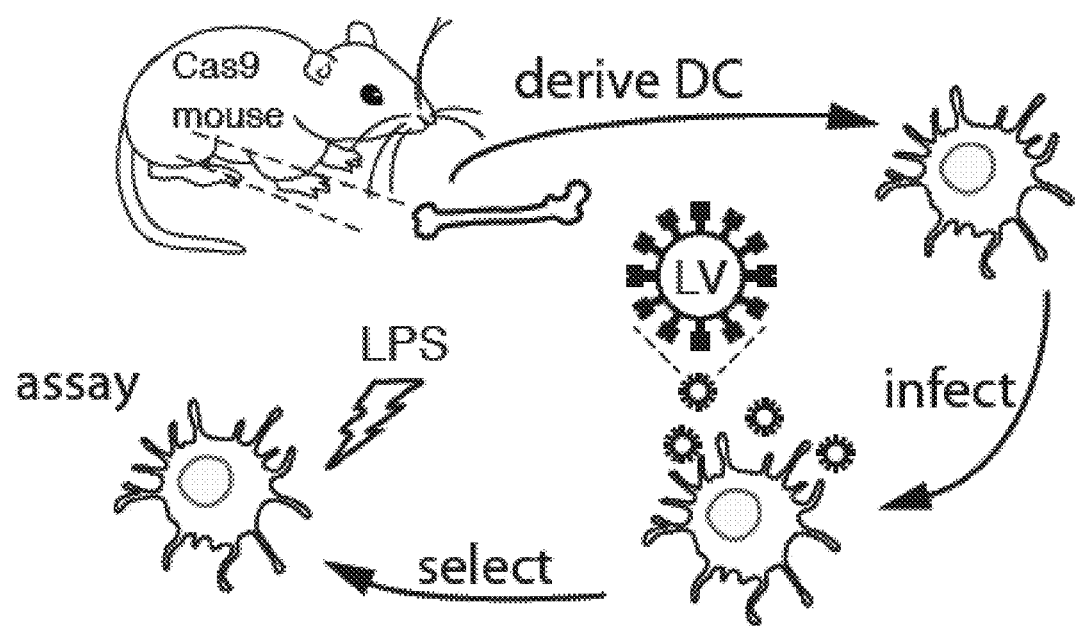
FIG. 1 shows a schematic of experimental flow in ex vivo genome editing of primary immune cells derived from constitutive Cas9-expressing mice.
Figure 2:
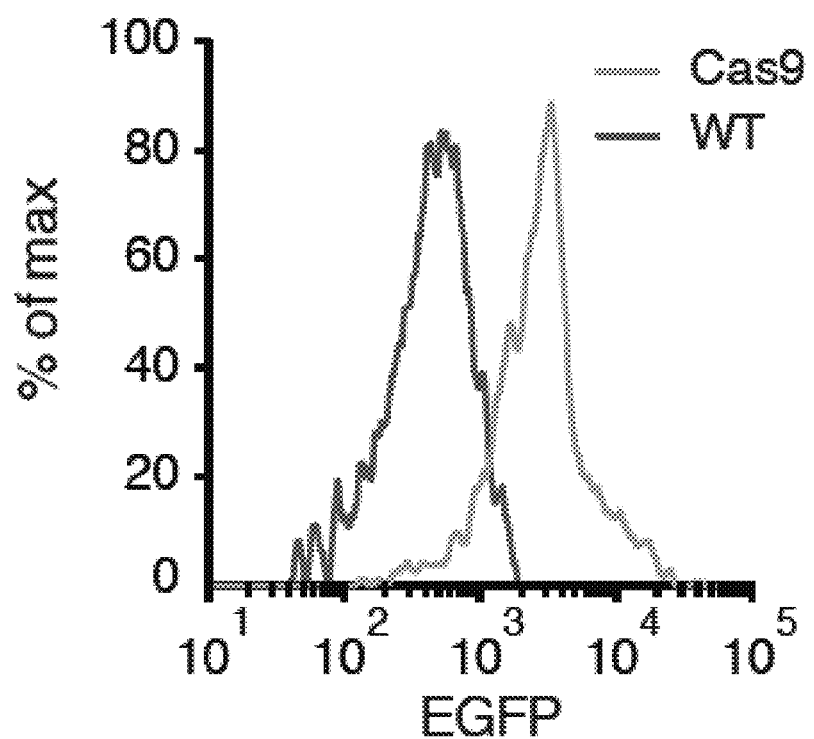
FIG. 2 shows a flow cytometry histogram of bone marrow cells from constitutive Cas9-expressing (green) and wild-type (blue) mice, showing Cas9-P2A-EGFP expression only in Cas9 mice. Data are plotted as a percentage of the total number of cells.
Figure 3:
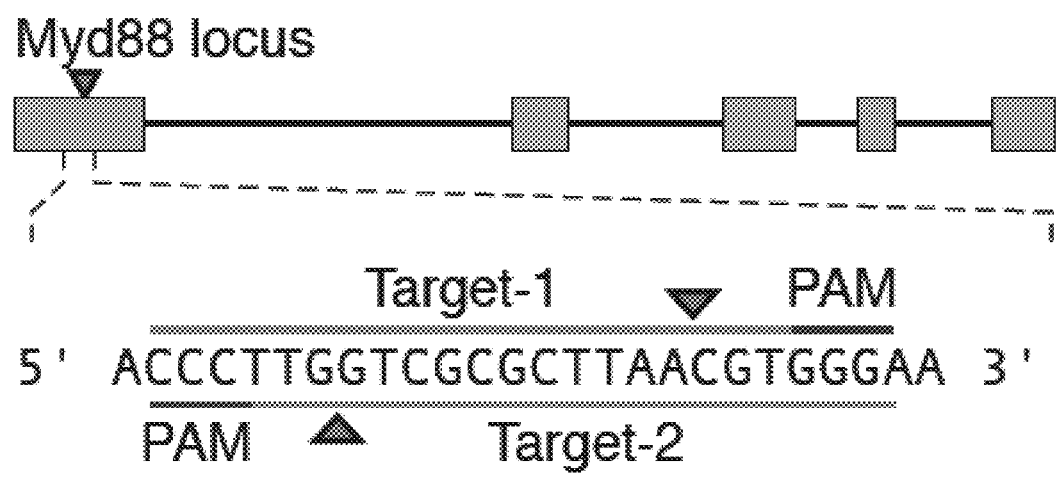
FIG. 3 shows sgRNA design for targeting the mouse Myd88 locus (SEQ ID NO: 27).
Figure 4:
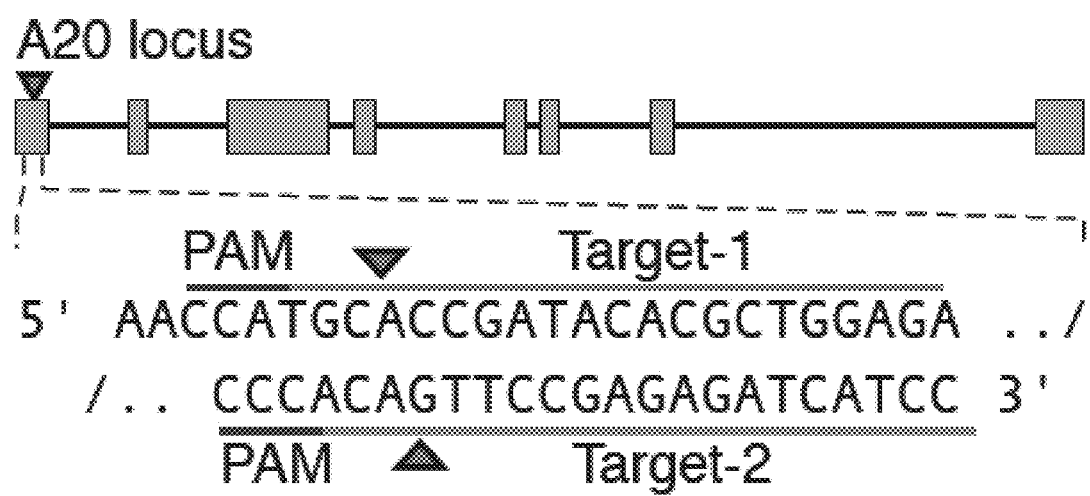
FIG. 4 shows sgRNA design for targeting the mouse A20 locus (SEQ ID NOS: 28 and 29, respectively, in order of appearance).
Figure 5:
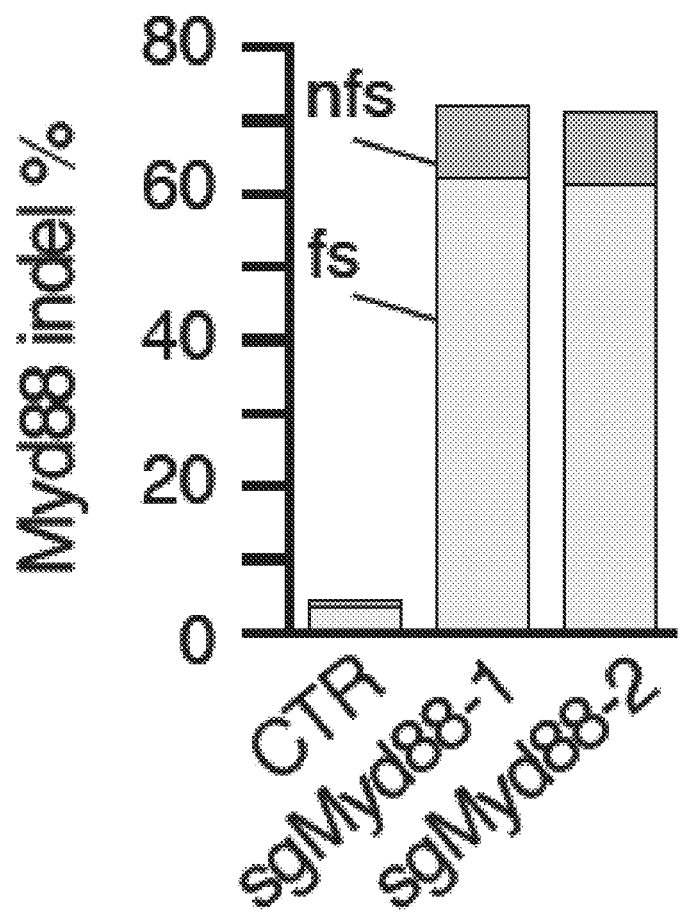
FIG. 5 shows Myd88 indel analysis of constitutive Cas9-expressing DCs transduced with either a Myd88-targeting sgRNA (sgMyd88-1 and sgMyd88-2) or controls (CTR, average of four control sgRNAs), showing indel formation only in Myd88-targeted cells. Data are plotted as the percent of Illumina sequencing reads containing indels at the target site. Mutations are categorized as frame-shift (fs, yellow bar) or non-frame-shift (nfs, orange bar).
Figure 6:
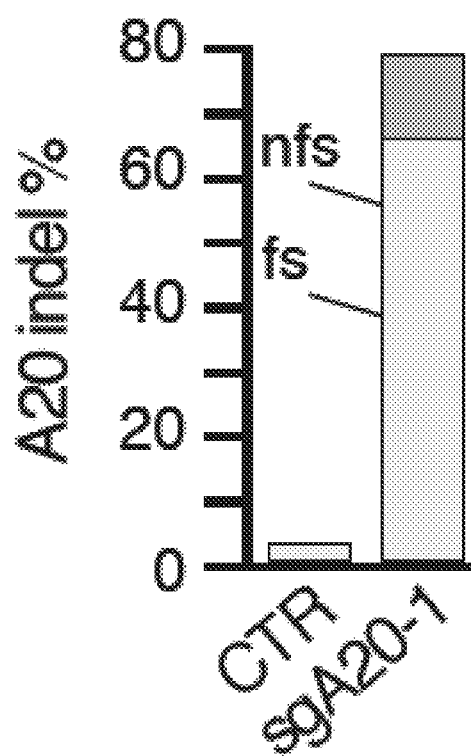
FIG. 6 shows A20 indel analysis of constitutive Cas9-expressing DCs transduced with either an A20-targeting sgRNA (sgA20-1) or controls (CTR, average of four control sgRNAs), showing indel formation only in A20-targeted cells. Data are plotted as the percent of Illumina sequencing reads containing indels at the target site. Mutations are categorized as frame-shift (fs, yellow bar) or non-frame-shift (nfs, orange bar).
Figure 7:
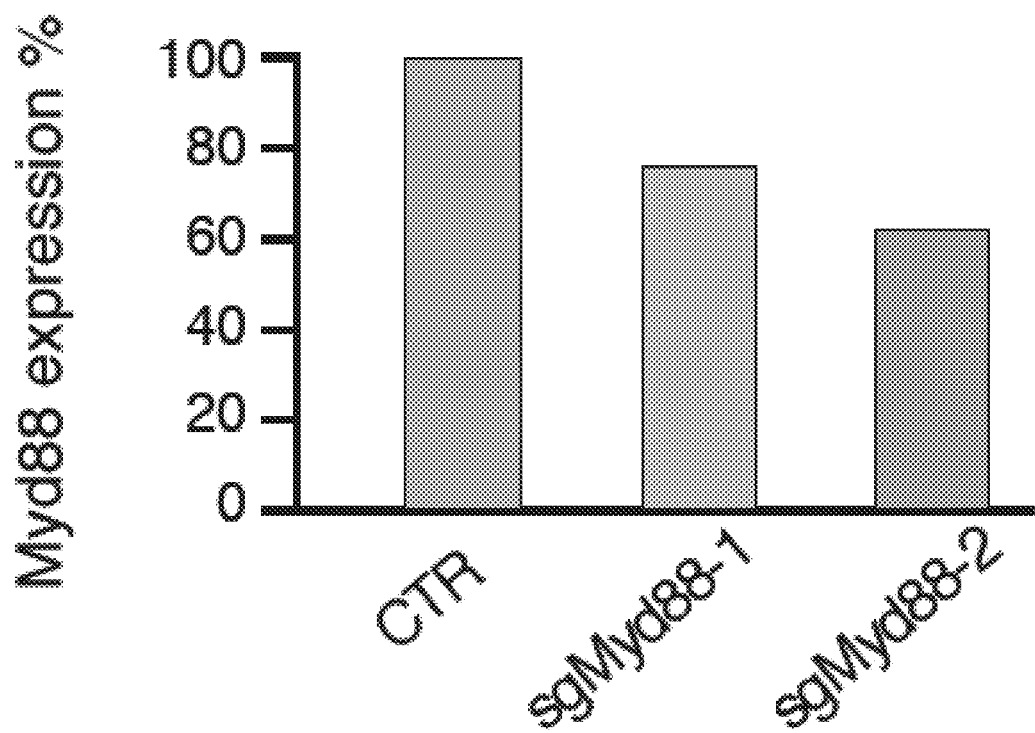
FIG. 7 shows Myd88 mRNA quantification of constitutive Cas9-expressing DCs transduced with either Myd88-targeting sgRNA (sgMyd88-1 or sgMyd88-2) or controls (CTR, average of six control sgRNAs), showing reduced expression only in Myd88-targeted cells. Data are plotted as Myd88 mRNA levels from Nanostring nCounter analysis.
Figure 8:
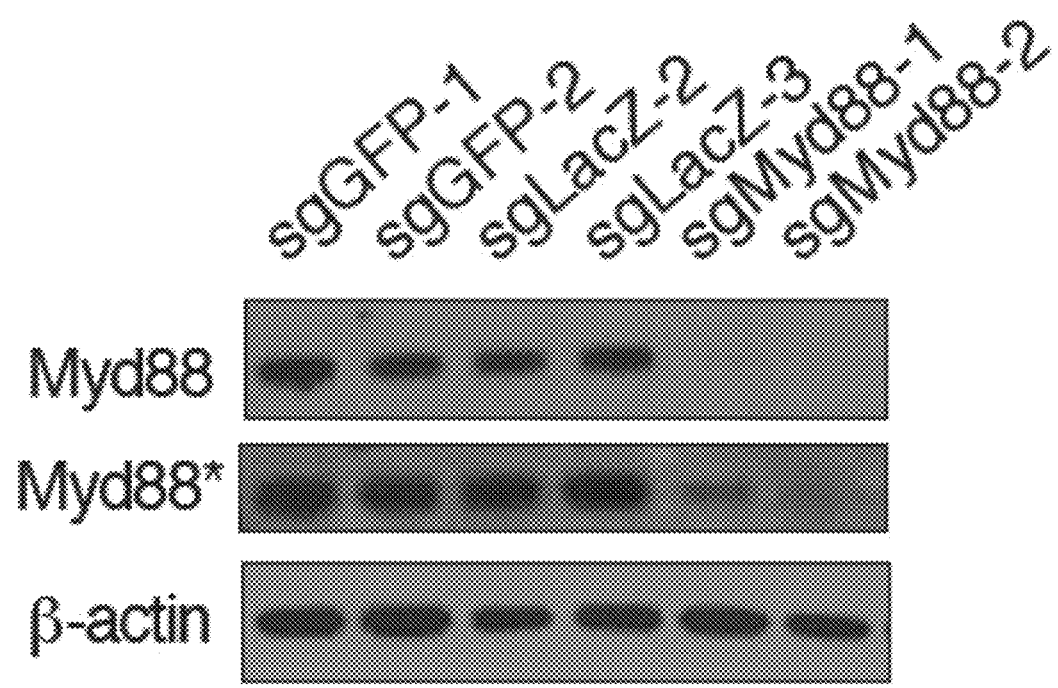
FIG. 8 shows an immunoblot of constitutive Cas9-expressing DCs transduced with either Myd88-targeting sgRNA (sgMyd88-1 or sgMyd88-2) or controls (four control sgRNAs), showing depletion of Myd88 protein only in Myd88-targeted cells. Beta-actin was used as a loading control. * overexposed, repeated measurement.

Applicants first verified the expression of Cas9 in bone marrow from constitutive Cas9-expressing mice (FIG. 2). Similarly, Applicants validated Cas9 expression in many other immune cell types (FIG. 3). Two days after culturing bone marrow cells from the constitutive Cas9-expressing mice Applicants infected BMDCs with lentivirus encoding two different sgRNAs targeting early exons of either MyD88 (FIG. 3) or A20 (FIG. 4), two well-characterized positive and negative regulators of Toll-like receptor 4 (TLR4) signaling, respectively. At seven days post transduction Applicants activated cells with lipopolysaccharide (LPS) and performed functional analysis (FIG. 1). Applicants found indels in 67-78% of sequencing reads (FIG. 5-6), leading to reduction in mRNA (FIG. 7) and protein (FIG. 8).

Figure 9:
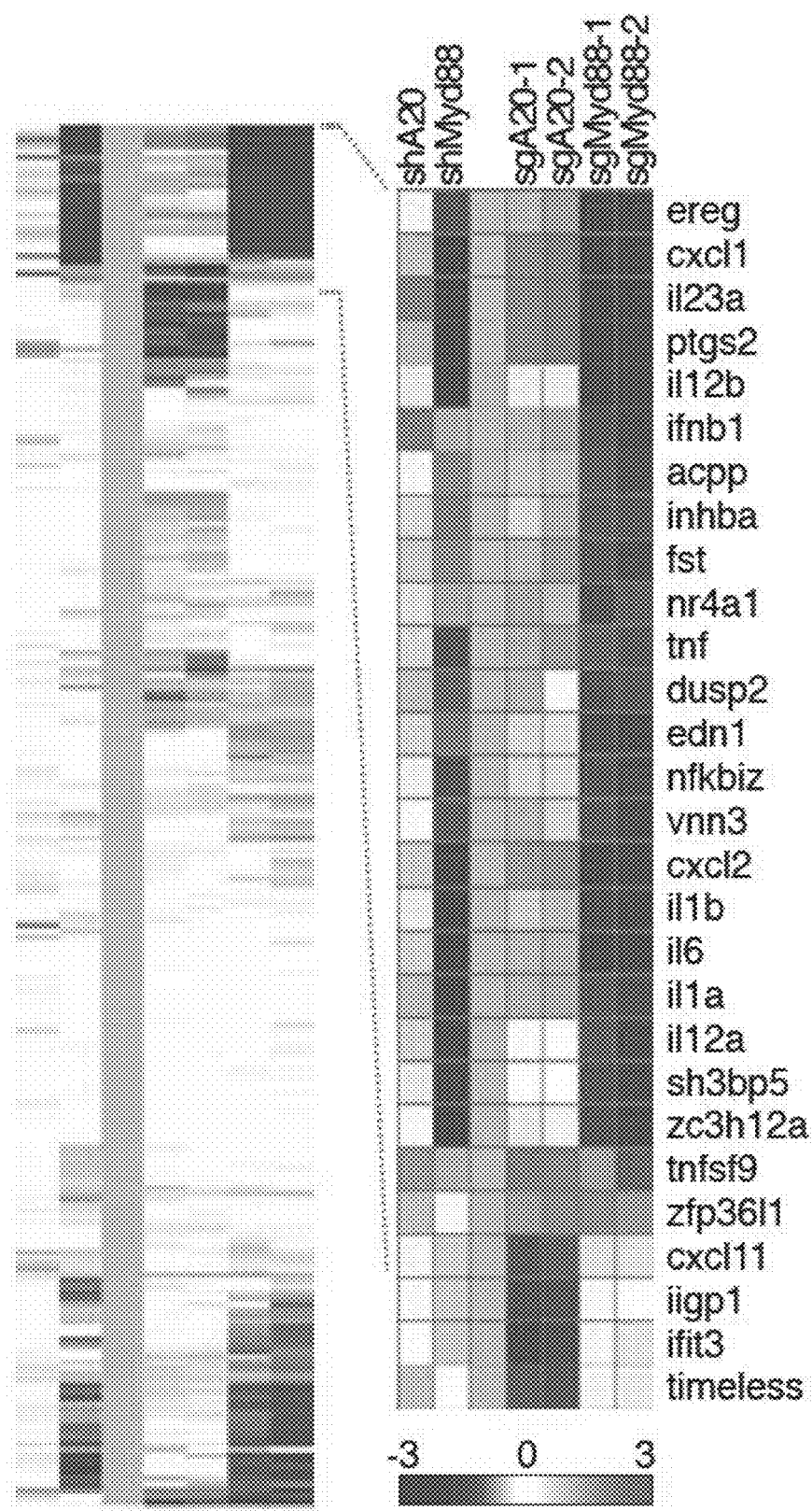
FIG. 9 shows nanostring nCounter analysis of constitutive Cas9-expressing DCs transduced with either Myd88-targeting sgRNA (sgMyd88-1 or sgMyd88-2) or shRNA (sh-Myd88), or A20-targeting sgRNA (sgA20-1 or sgA20-2) or shRNA (shA20), showing an altered LPS response. Inset: the cluster showing the highest difference between Myd88- and A20-targeting sgRNAs, including key inflammatory genes (IL1a, IL1b, Cxcl1, Tnf, etc.). Red: high; blue: low; white: unchanged; based on fold change relative to measurements with six control sgRNAs.
Figure 10:
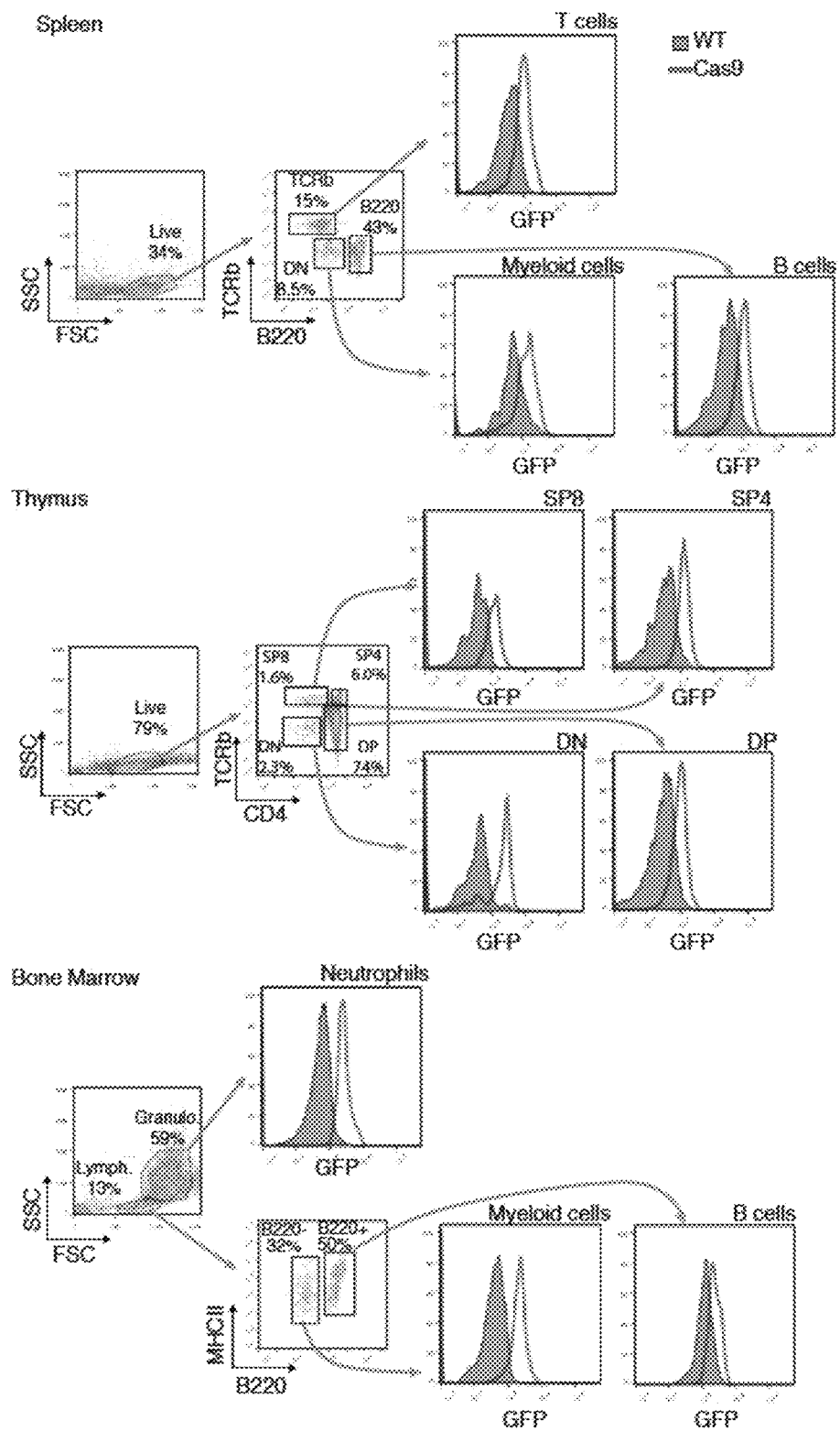
FIG. 10 shows flow cytometry scatter plots and histograms showing Cas9-P2A-EGFP positive immune cells of various immune cell types from constitutive Cas9-expressing but not wild-type (WT) mice.

DCs specialize in pathogen detection and initiation of appropriate immune responses (Mellman and Steinman, 2001). Therefore, Applicants measured the expression of 276 representative genes of the LPS response, using the Nanostring nCounter, in cells targeted for Myd88 or A20 as compared to controls (FIG. 9). As predicted, depletion of MyD88 resulted in a reduction of inflammatory response genes, whereas depletion of A20 resulted in an increase of inflammatory response genes. These effects were comparable to those observed with shRNA-mediated knockdown in independent experiments (FIG. 9). Taken together, Applicants results demonstrate the potential of constitutive Cas9-expressing mice for efficient perturbation in primary cells.

Example 3

Genome-wide CRISPR screens in primary mouse dendritic cells

Figure 11:
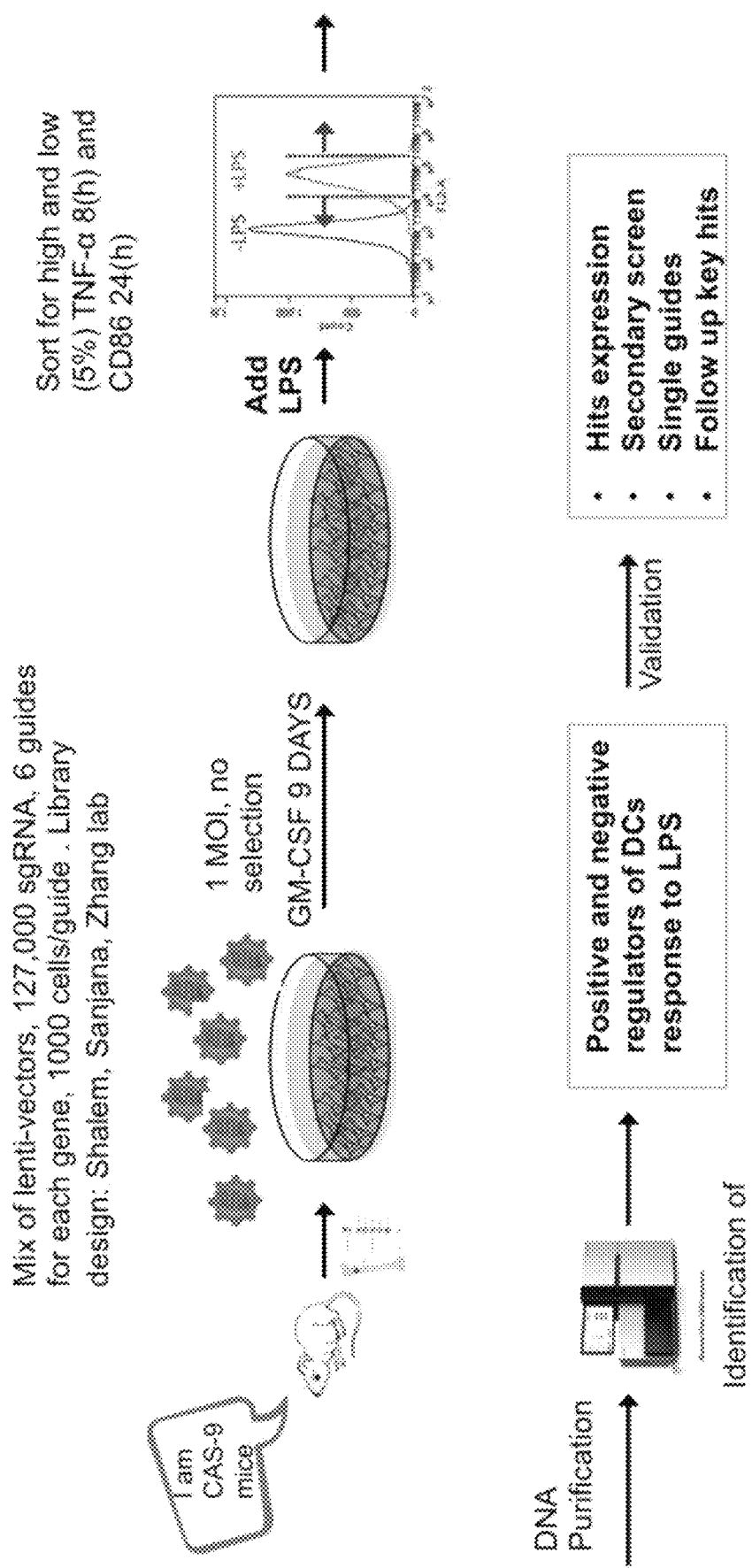
FIG. 11 shows a schematic representation of a genome-wide CRISPR screen in primary mouse dendritic cells.

In this example, Applicants establish a genome wide screen for positive and negative regulators of the LPS response in primary mouse dendritic cells (DCs). Bone marrow cells from Cas-9 expressing transgenic mice are infected with a library of *lenti*-virus that contains six guide RNAs for each mouse gene (including miRNAs), plus negative control guides that do not target any sequence in the mouse genome. A mixture of mouse primary cells is created and grown in condition that promote differentiation towards DCs. In this cell mixture each cell contains on average one mutation in one of the targeted genes. The next stage is to stimulate DCs with LPS (a bacterial component) and then isolate cells that fail to respond (indication of a mutation in a positive regulator of the LPS response) or that have a stronger than normal response (indication of a mutation in a negative regulator of the response). The stimulation step is performed in the presence or absence of IL-10. The readout for DC activation upon LPS is based on staining for the anti-inflammatory cytokine TNF-α or the cell surface receptor CD-86. The last stage is to identify the guide RNAs present at higher levels in cells that show the desired phenotype (especially high or especially low expression of the readout marker CD-86 or TNF-α), and verify the results. The method is shown schematically in FIG. 11.

Figure 13:
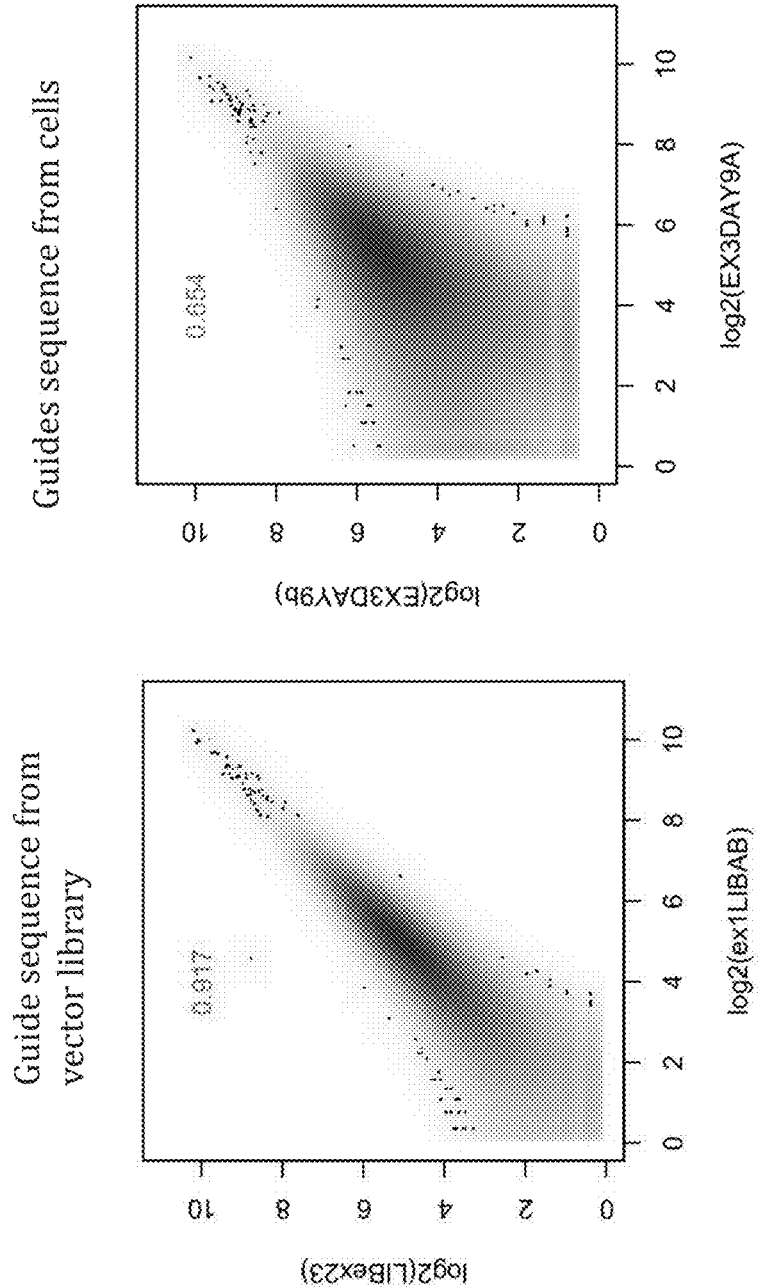
FIG. 13 shows the levels of guides in the input library of vectors or of guides that were sequenced from cells after 9 days of expression.
Figure 14:
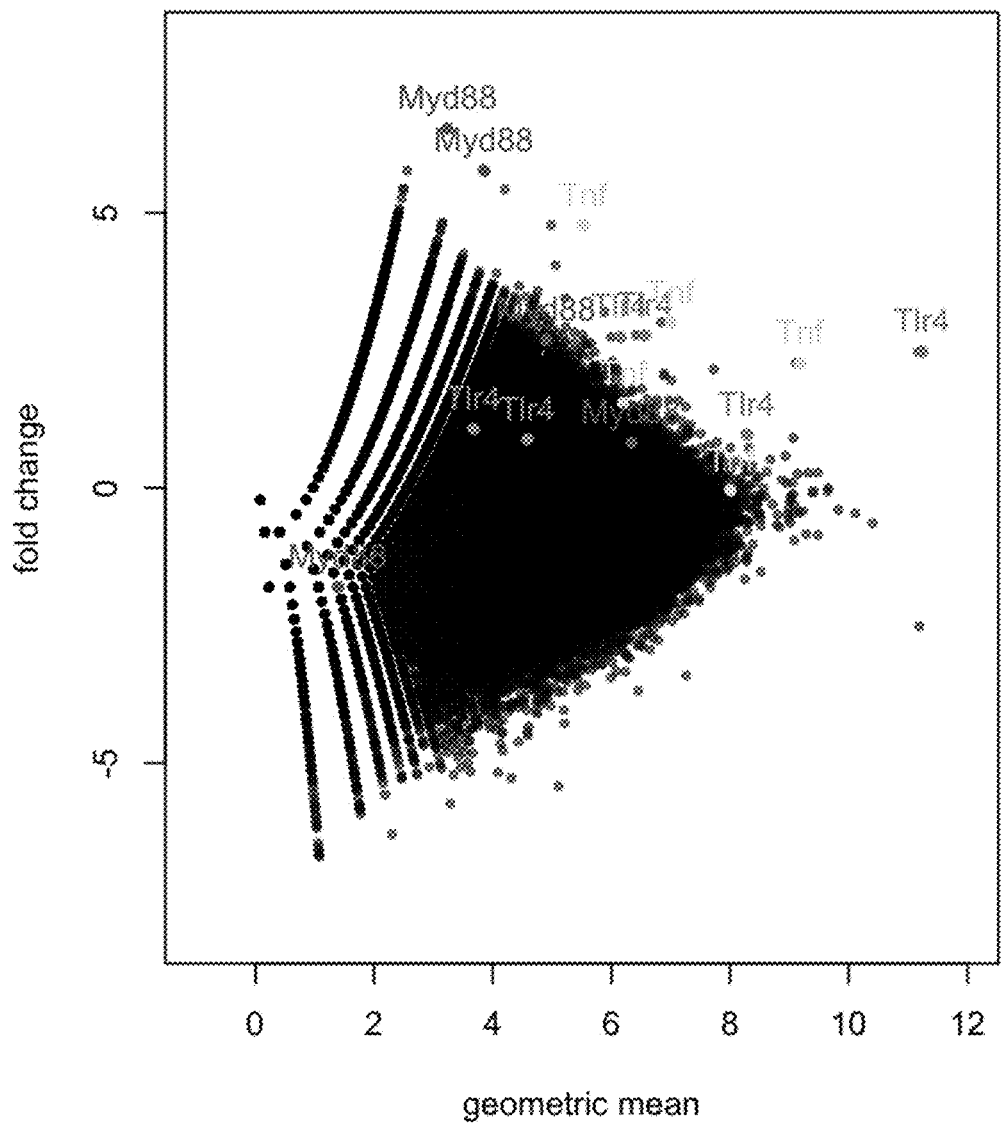
FIG. 14 shows the fold changes of guide levels in experiment 1 (y axis) as per FIG. 12 as a function of the mean (x axis). The fold change in guide level is between the high and the low bins of TNF α expression. Known regulators of the LPS response are highlighted.
Figure 15:
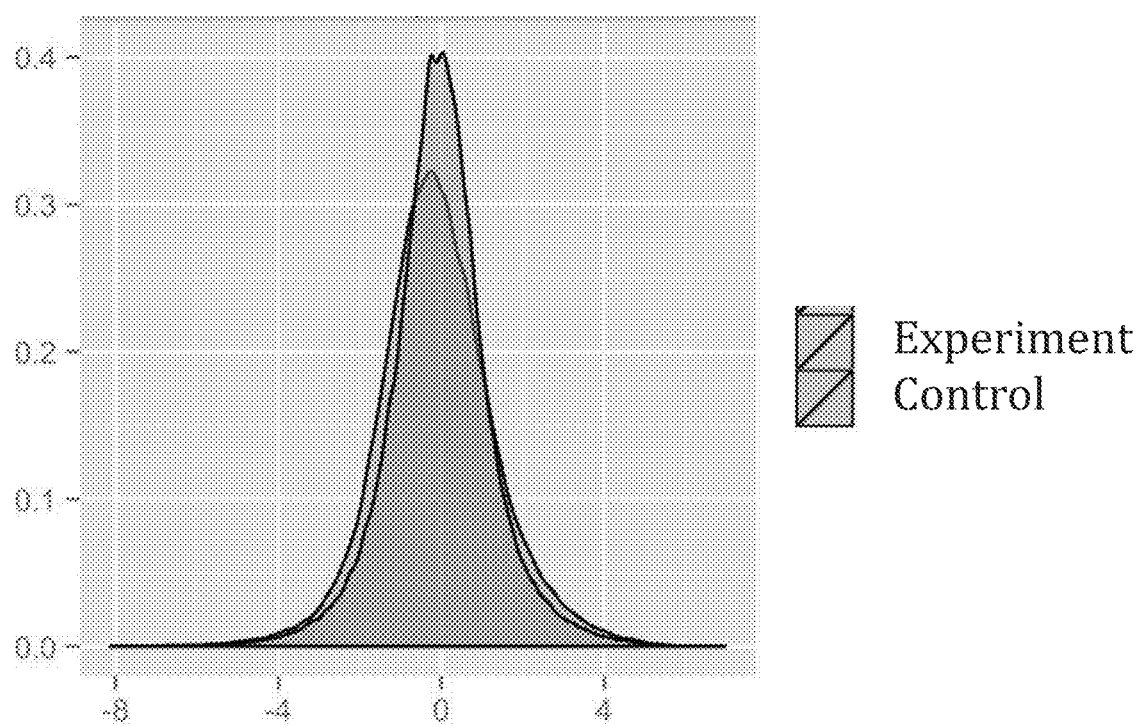
FIG. 15 shows the density plot of the fold changes in guide levels. Blue: fold changes between high and low TNF-α bins; pink: fold changes in two repeats of the control experiment.
Figure 16:
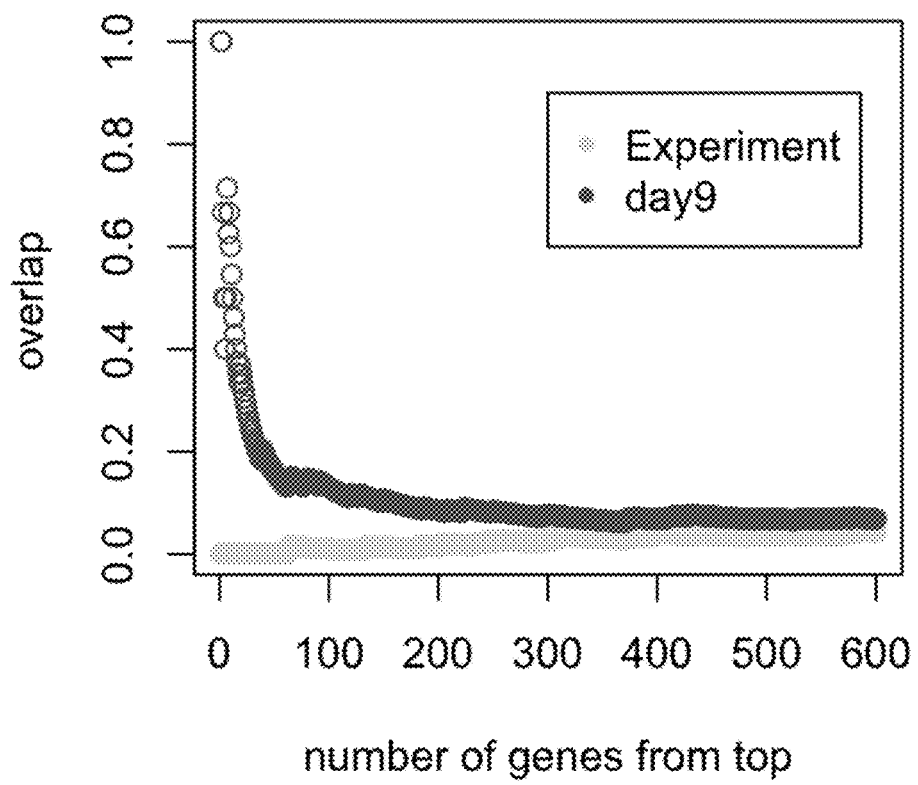
FIG. 16 depicts the overlap between the top hits of two biological repeats of experiment 1), day 9 is presented as a control.

Three screens were done as presented in FIG. 12. In each of the screens, cells were expanded for 9 days and after LPS stimulation cells were sorted and the guides from the sorted population were amplified and sequenced. The guide expression is presented in FIG. 13. These expression profiles show the noise level of the screen. FIG. 14 shows the fold change of the guides that were sequenced from the "low" TNF bin versus the "high" TNF bin (experiment 1). Guides that target genes that are known to affect TNF expression are highlighted. Guides targeting these genes are highly enriched in the "low" TNF bin. The expected signal in comparison to the background can be deduced from FIG. 15. In order to increase the statistical significance, three biological replicates of experiment 1 were performed. The overlap between the top hits of two of the replicates is presented in FIG. 16 in comparison to controls (no sorted samples).

In three repeats on the screen (using 200 million cells in each repeat) Applicants reproducibly found many of the known regulators of the LPS response including Tlr4, Myd88, CD14, Ticam1, Ticam2 and many new potential regulators to be verified individually. The large scale screen has high potential to find new regulators of the LPS response in BMDCs and therefore new targets for drug therapy.

Example 4

Genome-wide CRISPR screens in T cells

Figure 17:
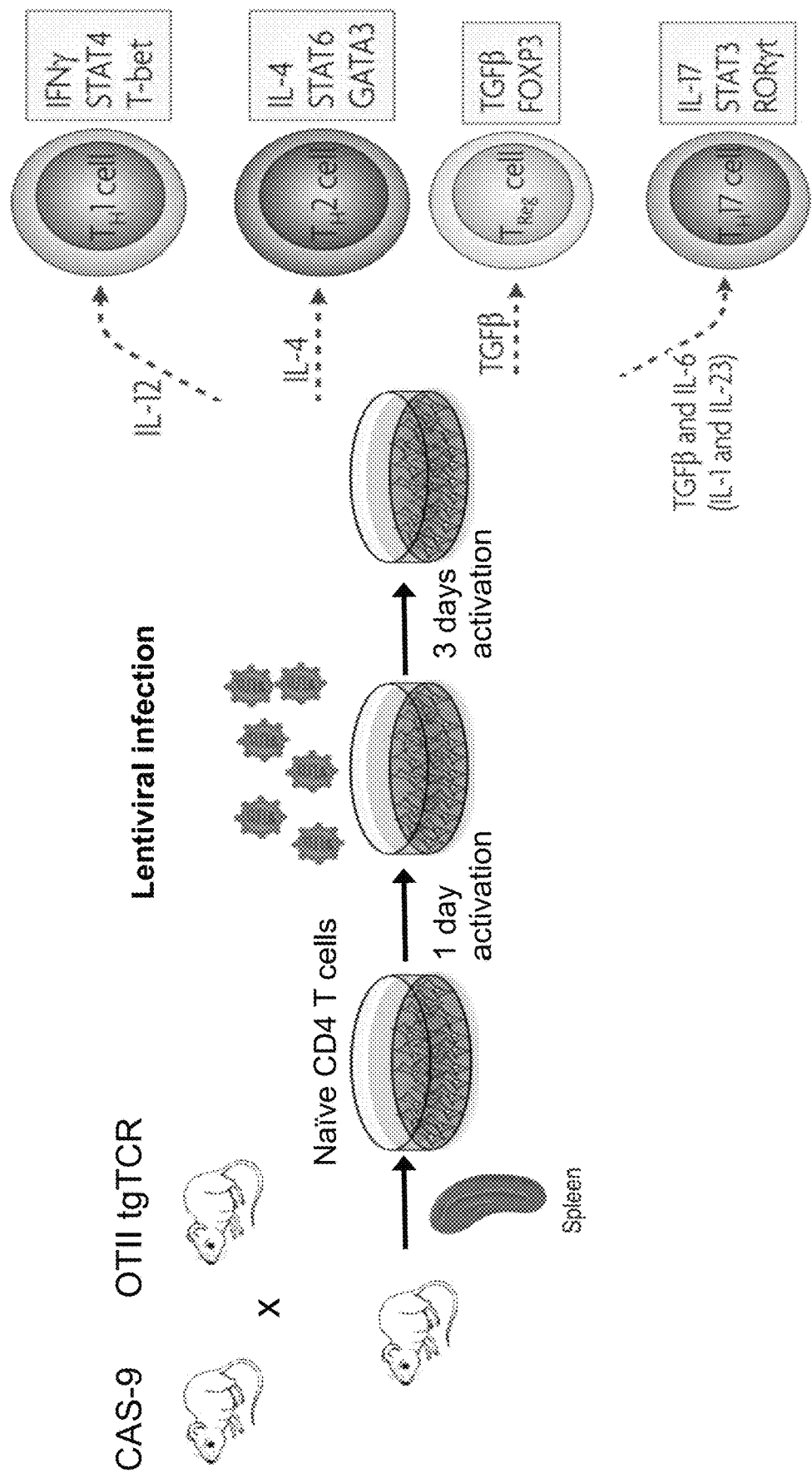
FIG. 17 shows a schematic representation of a genome-wide CRISPR screen in T cells.

In this example, Applicants establish a genome wide screen for positive and negative regulators of CD4+ T cell differentiation. OT-II mice (which express the mouse alpha-chain and beta-chain T cell receptor that pairs with the CD4 coreceptor and is specific for chicken ovalbumin 323-339 in the context of I-A b, see Barnden et al. (1998), Immunol Cell Biol 76(1):34-40) are crossed with Cas9 transgenic mice to generate a transgenic mouse having cells that express Cas9 and an ovalbumin-specific αβ-T cell receptor. T cells from the progeny of such mice are infected with a library of *lenti*-virus that contains six guide RNAs for each mouse gene (including miRNAs), plus negative control guides. Guide libraries are used to knock out genes involved in T cell differentiation to 4 subsets: Th1, Th2, Th17 and Treg. For each subset, T cells are sorted for high or low differentiation signal and the guides in those cells are sequenced to find positive and negative regulators of differentiation. The method is shown schematically in FIG. 17.

Example 5

A system for cell-autonomous, pooled genetic screens in BMDCs derived from Cas9-expressing mice Applicants describe efficient knockout of genes when using the CRISPR system in primary bone marrow derived dendritic cells (BMDCs) isolated from Cas9-expressing mice (Platt et al., 2014). Given the efficacy of this approach compared to RNAi, Applicants reasoned that it should be possible to conduct improved genome-wide genetic screens in primary cells, with significant increases in on-target efficacy and reduction in off-target effects compared to RNAi screens (Shalem et al., 2014).

To enable genome-wide pooled genetic screens, Applicants developed a cell autonomous readout of innate immune activation by intracellular staining of a central inflammatory cytokine, Tnf. To test the assay, Applicants individually transduced BMDCs with lentiviruses expressing short guide RNAs (sgRNAs) that target each of three genes: (1) Tlr4, the cell membrane receptor that senses bacterial LPS; (2) Myd88, a key component required for Tlr4 signaling to induce Tnf; and (3) Zfp36 (TTP), an RNA binding protein that destabilizes Tnf mRNA (Carballo et al., 1998; Rabani et al., 2014). Applicants isolated bone marrow cells from transgenic mice that constitutively express spCAS-9, transduced cells with lentiviruses targeting these 3 control genes, and differentiated DCs for an additional seven days using GM-CSF (Experimental Procedures) (Platt et al., 2014). Applicants then activated BMDCs with LPS, in the presence of Brefeldin to block Tnf secretion, and at 8 hours post-activation detected Tnf with a fluorescent antibody using flow cytometry. Compared to a non-targeting sgRNA control, sgRNAs targeting Myd88 or Tlr4 strongly reduced Tnf, whereas sgRNAs targeting Zfp36 increased Tnf (FIG. 18A). These results—which are consistent with previous findings (Platt et al., 2014) that endogenous expression of CAS-9 is sufficient for efficient introduction of frameshift mutations in primary cells—provide an experimental system for an autonomous genome-wide pooled screen based on cell sorting. Notably, the addition of Brefeldin blocks the secretion of all cytokines, thus preventing secondary signaling and focusing the screen on the proximal sensing pathway.

Example 6

A genome-wide pooled sgRNA library screen in primary BMDCs

Figure 18B:
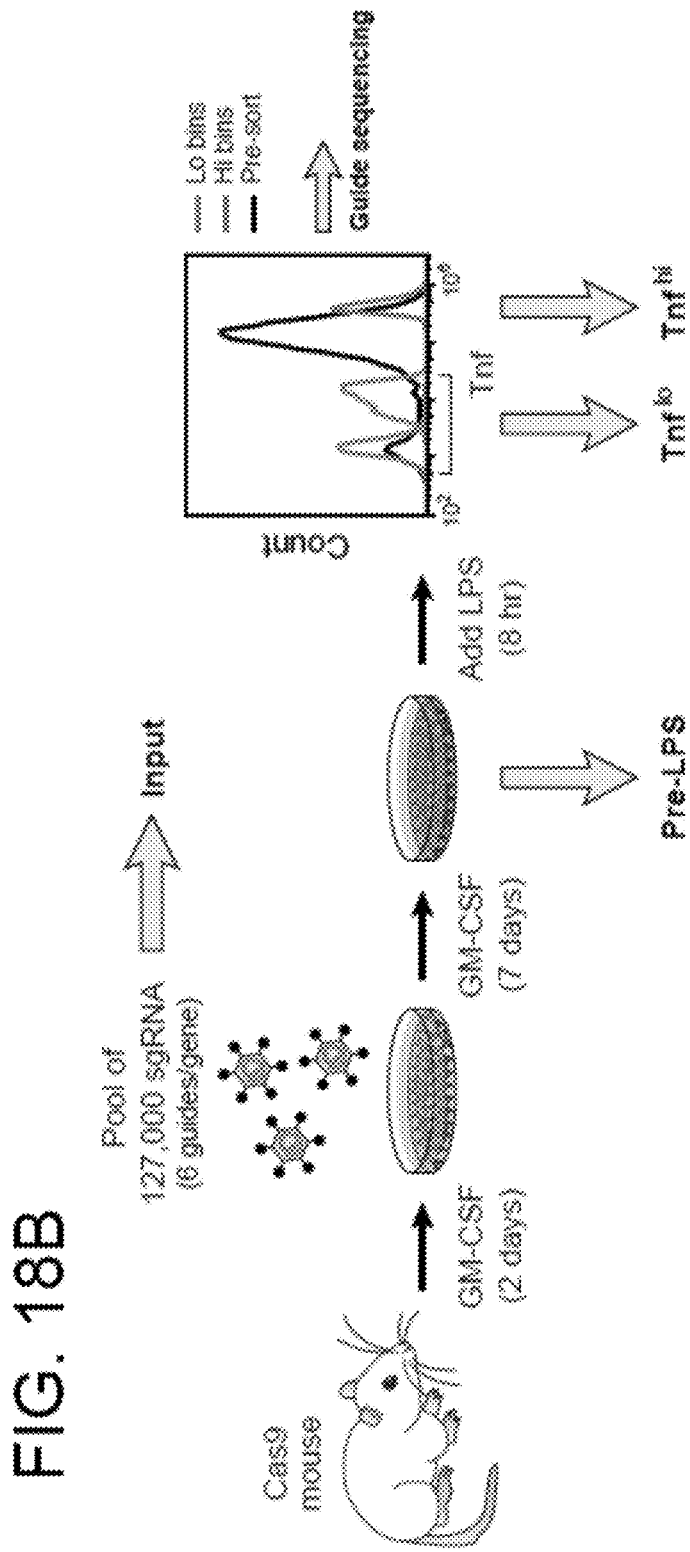

Applicants performed three independent, pooled genome-wide screens using a library of lentiviruses harboring 125,793 sgRNAs targeting 21,501 protein-coding and miRNA genes annotated in the mouse genome (Sanjana et al., 2014), as well as 1,000 non-targeting sgRNA as negative controls (FIG. 18B). In each of the three replicate screens, Applicants infected 60-200 million BMDCs with the library at a multiplicity of infection (MOI) of 1, stimulated cells with LPS and sorted Cd11c+ cells based on high or low Tnf expression levels (FIG. 18B, Experimental Procedures). Applicants then amplified and sequenced sgRNAs from 4 sources (FIG. 18B thick grey arrows): post-LPS cells with (1) high Tnf ("$Tnf^{hi}$") or with (2) low Tnf ("$Tnf^{lo}$"), (3) cells from the last day of differentiation prior to LPS stimulation (day 9, "pre-LPS"), and (4) plasmid DNA of the input lentiviral library ("Input"). Applicants reasoned that sgRNAs against positive regulators of Tnf expression would be enriched in $Tnf^{lo}$ relative to $Tnf^{hi}$, that sgRNAs targeting negative regulators will be enriched in $Tnf^{hi}$ relative to $Tnf^{lo}$; and that sgRNAs targeting genes essential for DC viability or differentiation would be depleted in pre-LPS compared to Input. Thus, an aspect of the invention provides a more sensitive assay and/or screen for negative regulators by using lower levels of LPS.

A computational strategy to identify enriched or depleted sgRNAs

Figure 23A:
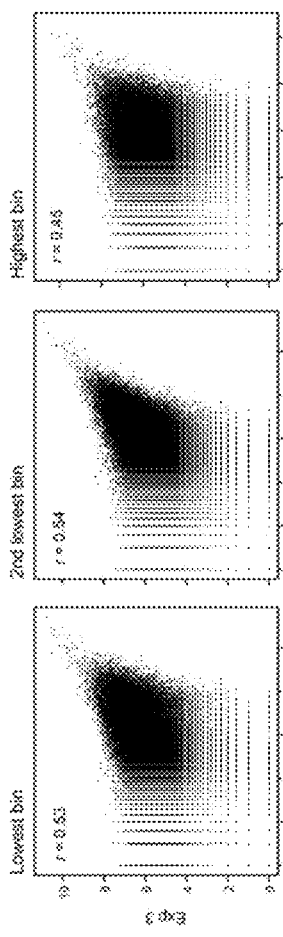
FIG. 23A-H Quality measures of a Genome wide pooled CRISPR screen in mouse primary DC. (A) Reproducibility. Shown are scatterplots comparing the $\log_2$(quantile normalized read counts) of sgRNAs between two replicate screens for the lowest bin (left), 2nd lowest bin (middle), and top bin (right). Pearson correlation coefficient (r) is shown in top left corner. (B-E) Top ranked screen hits compare well between the DESeq and Z-score approaches. (B,C) Scatter plots compare the ranks based on the DE-Seq approach (X axis) and Z score approach (Y axis) for either positive regulators (B) or negative regulators (C) among the top-100 ranked genes. The Spearman rank correlation coefficient (p) is noted. (D, E) Shown is the Jaccard index between the Z-score and DE-Seq based approaches (Y-axis, intersection over union) for sliding windows of 50 genes from top of the ranked lists (X axis) for the true ranking (black) and with random shuffling (grey) of the Z-score ranks, for either the positive (D) or negative (E) regulators. The signal is diminished at rank ~150 and ~50 for positive and negative regulators, respectively. (F) sgRNAs that target translation genes are enriched in the "Input" library versus "Pre-LPS". Left: Scatterplot compares the normalized fold change in sgRNAs (Input/Pre-LPS) to the mean abundance in the two libraries. Middle and Right: Distribution of the normalized fold change (Input/Pre-LPS; Y axis) in either sgRNAs (middle) or genes (right; mean of the top 4 ranked sgRNAs). Orange: translation genes; black: all genes; grey: non-targeting controls. (G) sgRNAs targeting known regulators of LPS response are highly significant in DE-Seq analysis. MA-plots compare for either sgRNAs (left) or genes (right), the DE-Seq calculated fold-change between $TNF^{hi}$ and $TNF^{low}$ (Y axis) to the mean abundance of the sgRNA or gene. (H) Screen hits are more likely to be expressed post-LPS and at higher level than all other genes. Violin plots show the distribution of mean expression (Y axis) along LPS stimulation (0 h, 2 h, 4 h, 6 h) in control cells, for top-169 hits (right) and for all other genes (left).

To perform such comparisons, Applicants determined the relative enrichment of sgRNAs across the 4 sources ($Tnf^{hi}$, $Tnf^{lo}$, pre-LPS and Input). First, Applicants considered technical sources of noise. Given that each Tnf bin consists of ~5 million cells, it is likely that some of the ~120,000 sgRNAs are undersampled by chance. Indeed, while matched bins are fairly well correlated between replicates (Pearson r=0.45-0.54, FIG. 23A), there is greater variance for the least abundant sgRNAs (FIG. 23A). Next, in order to score and rank the genes with respect to their effects on Tnf in response to LPS, Applicants devised two strategies to compare the abundance of sgRNAs between the $Tnf^{lo}$ (average of two low bins) and the $Tnf^{hi}$ bins. In the first approach, Applicants calculated for each sgRNA a Z score, based on fold change of the abundance of each sgRNA between samples, after the abundance of each sgRNA was quantile normalized and averaged across replicates. Applicants then derived a score per gene by averaging the Z scores for the 4 sgRNAs with the highest Z scores per gene. In the second approach, similar to methods for differential expression (DE) analysis (Love et al., 2014), Applicants scored differential sgRNA abundance with a model that first averages on all normalized sgRNA abundance values for each gene, then takes the fold change between samples in each replicate, and finally fits it with a model to compare the observed fold change to a null expectation with a likelihood ratio test (Experimental Procedures).

Figure 23B:
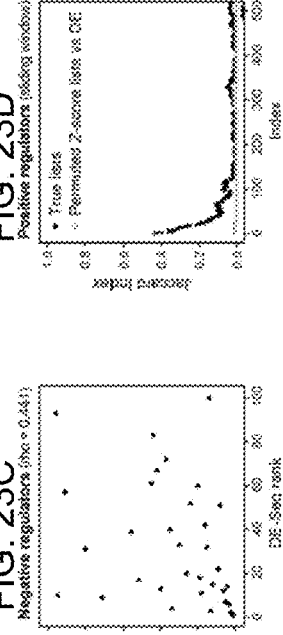
Figure 23C:
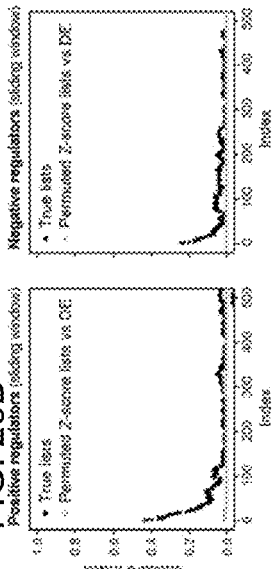
Figures 23D, 23E:
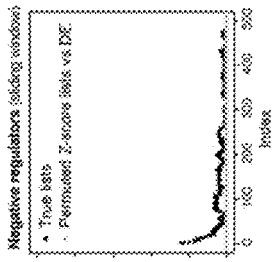

The top ranked genes substantially overlap between the two approaches (50/100 for positive regulators, 30/100 for negative regulators, $P<10^{-10}$, Hypergeometric test), and their rankings are well correlated (Spearman ρ=0.67 for positive regulators, 0.44 for negative regulators; FIG. 23B, C). The rankings subsequently diverge at ranks 150 and 50 for the positive and negative regulators, respectively (FIGS. 23D and 23E). Note that the overlap is highly significant, but far from perfect. This is entirely expected given the extent of noise in the screen (and the corresponding estimate of 50% FDR at the 100 top ranked genes mark), and highlights the susceptibility of single ranking approaches to this noise.

The screen correctly identifies known regulators of cell viability, differentiation, Tnf expression and Tlr4 signaling.

Figure 18C:
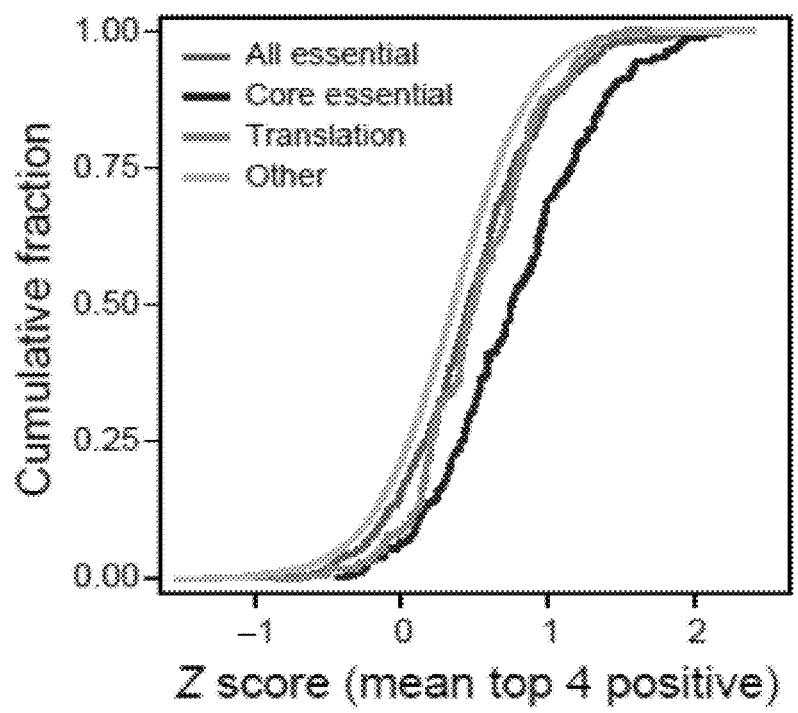
Figure 23H:
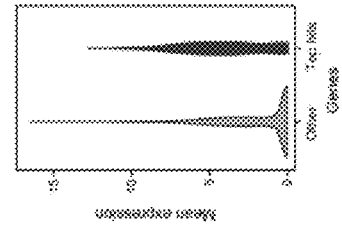

To assess the initial quality of the screen and scoring scheme, Applicants first determined that, as expected, sgRNAs against genes required for essential cell processes were depleted in pre-LPS samples compared to Input (FIG. 18C and FIG. 23F), including those targeting genes previously annotated as essential (Hart et al., 2014) ($p<10^{-16}$, KS test) or as involved in translation (FDR q value=$1.26\times10^{-13}$, GOrilla (Eden et al., 2007)) (FIG. 18C and Table S1).

TABLE S1

| Ranked genes based on the enrichment in day 9 compare to the plasmid library |
|---|
| Vmn1r95 |
| Hist1h2br |
| Tbc1d10b |
| Mup9 |
| Gm14501 |
| mmu-mir-3473c |
| Rps13 |
| Pcdhac2 |
| Gm10377 |
| Basp1 |
| Rps2 |
| Slc44a3 |
| BC018507 |
| Mdm2 |
| Cflar |
| Nxf1 |
| Rps7 |
| Zscan4f |
| Gm21119 |
| Hist1h4n |
| Gab2 |
| Lce3f |
| Psmc5 |
| Mblac1 |
| Rpl7 |
| Arcn1 |
| Rbm25 |
| Uba1 |
| Rps17 |
| Psma4 |
| Npy |
| Hmgb1 |
| Rps8 |
| Pnrc1 |
| Gm8764 |
| Hist3h2a |
| Supt6 |
| Thoc2 |
| Usp5 |
| H2-L |
| Zfp781 |
| Vmn2r49 |
| Fxyd6 |
| Hist1h3i |

Figure 18D:
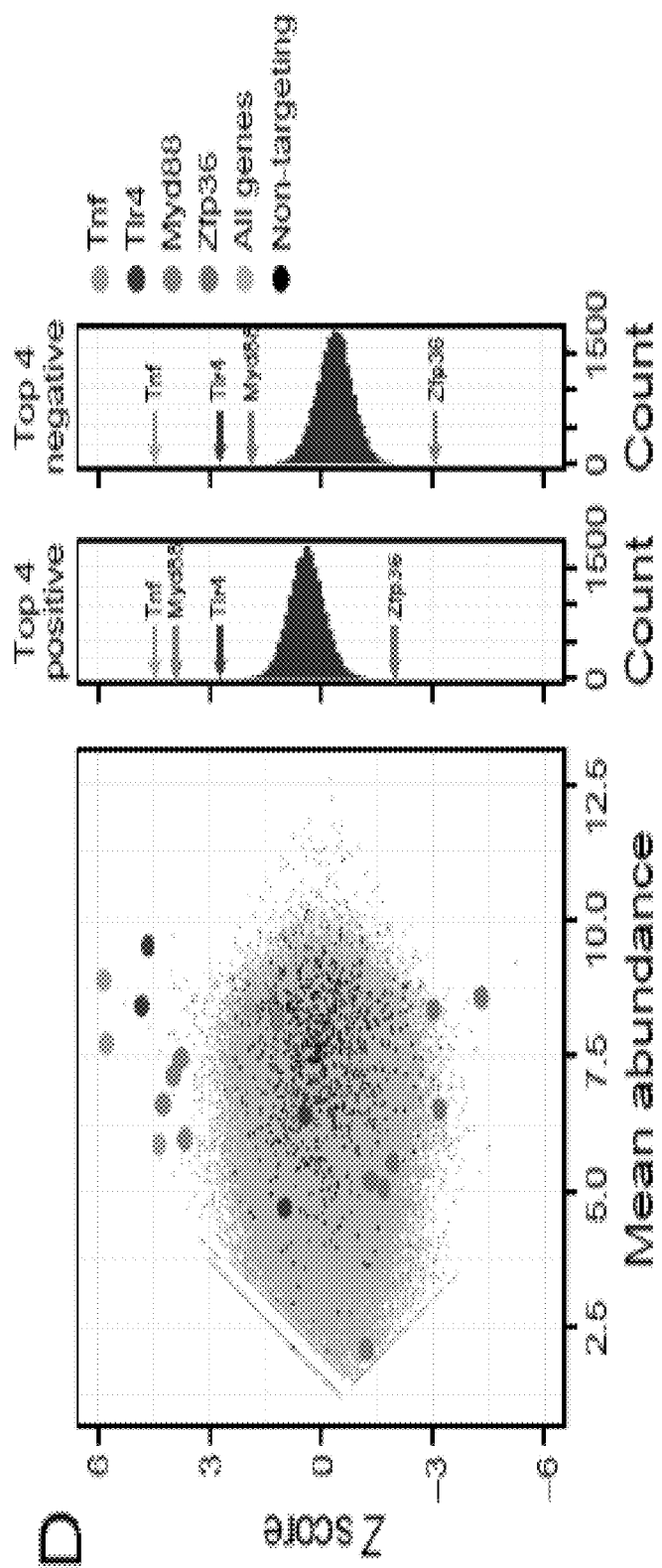
Figure 18E:
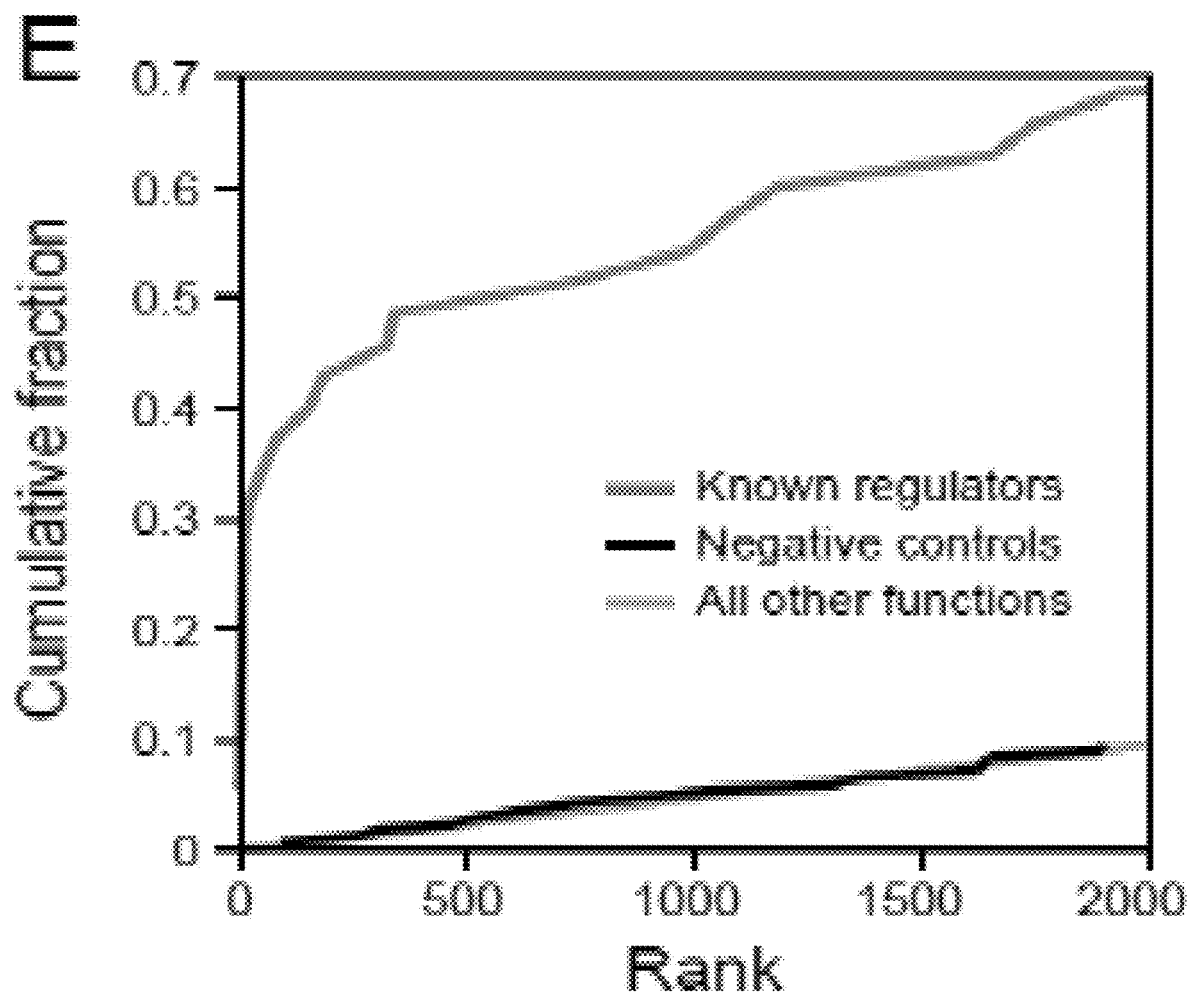
Figure 23G:
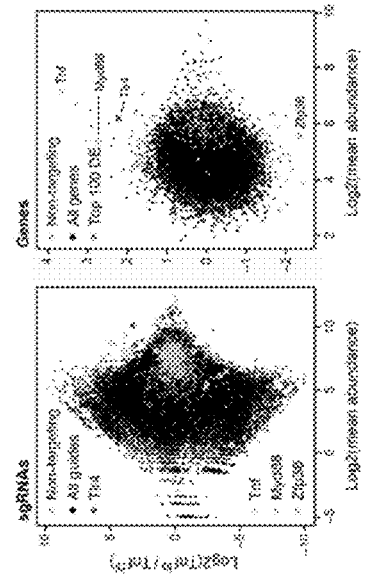
Figure 23F:
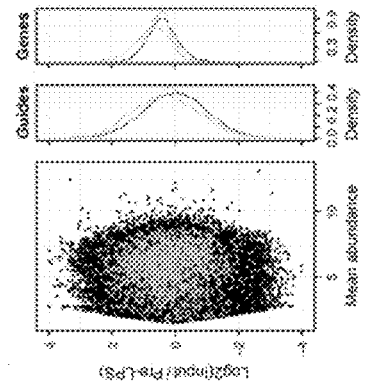

Next, a comparison of sgRNAs between Tnfhi and Tnflo was also consistent with the predictions, with sgRNAs targeting known positive regulators of the response (e.g., Tlr4 and Myd88) enriched in Tnflo compared to Tnfhi, and those targeting negative regulators (e.g., Zfp36) depleted in Tnflo (ZS analysis: FIG. 18D and Table S2; DE analysis: FIG. 23G). The top-ranked genes were highly enriched for those annotated as responsive to LPS (the highest scoring category; GOrilla, FDR q-val=$10^{-12}$) or assigned to the TLR4 to TNF pathway (in KEGG, FIG. 18E); they were also far more likely to be expressed (FIG. 23H, e.g., 78% of the top 169 genes, compared to 44% of all genes; P-value=10⁻¹⁶, Hypergeometric test), at higher levels (p=10' Kolmogorov-Smirnov (KS) test), and more likely to be differentially expressed following LPS stimulation based on RNA-Seq at 0, 2, 4 and 6 hours (Experimental Procedures; e.g., 35 of top-169 scoring genes (i.e., those with detectable mRNA among the 177 tested) had at least 2 fold differential expression; p=0.009, Tables S4 and S5). Candidate positive and negative regulators were equally likely to be induced and/or repressed (p=0.23, Hypergeometric test).

TABLE S2

| Positive regulator | Negative regulators |
|---|---|
| Tnf | Zfp36 |
| Ly96 | Atxn7l3 |
| Cd14 | Rc3h1 |
| Myd88 | Yy1 |
| Ticam2 | Dnttip1 |
| Dad1 | Rara |
| Ddost | Dusp1 |
| Ticam1 | Eif5 |
| Tirap | Stat5b |
| Tlr4 | Atp10b |
| Rela | Olfr1497 |
| Ctcf | Rfwd2 |
| Traf6 | Polq |
| Rpn1 | Nlrp4e |

TABLE S2-continued

| Positive regulator | Negative regulators |
|---|---|
| Rbx1 | Cypt3 |
| Pabpc1 | Ppp2r1a |
| Srp54c | B4galt5 |
| Xab2 | Pla2g7 |
| Rbck1 | Comtd1 |
| Tmem258 | Cxcl1 |
| Cebpb | Gja8 |
| Ikzf1 | Crygs |
| Ikbkb | Olfr1253 |
| Ddx39b | Becn1 |
| Ctr9 | Strap |
| Olfr187 | Klhdc7a |
| Pafl | Lcp2 |
| Gtf2b | Hspa5 |
| Polr2g | Ncor2 |
| Midn | Mycbp2 |
| Tipin | Mmp14 |
| Leo1 | Pdcd10 |
| Rpl10 | Pak6 |
| Actb | Caprin2 |
| Rpl35 | Eif2s1 |
| Mapkapk2 | Kidins220 |
| Sgms1 | Hmg20a |
| Gabpb1 | Gpt |
| Akirin2 | Nf1 |

TABLE S4

| geneID | mean expression | regulator | Rank according to positive z score | Rank according to negative z score | Rank according to DE | Z score secondary | DE score secondary |
|---|---|---|---|---|---|---|---|
| Crygs | 0 | neg | | 22 | 1172 | 993 | 1677 |
| Cypt3 | 0 | neg | | 15 | 71 | 1913 | 2409 |
| Klhdc7a | 0 | neg | | 26 | 44 | 2763 | 2558 |
| Lce3a | 0 | neg | | 939 | 82 | 797 | 1114 |
| Prol1 | 0 | pos | 421 | | 75 | 1577 | 1574 |
| Sox2 | 0 | neg | | 534 | 90 | 2600 | 1714 |
| Steap4 | 0.0114586 | pos | 60 | | 651 | 843 | 1472 |
| Fam155a | 0.0278761 | pos | 54 | | 1301 | 1744 | 1049 |
| Scube3 | 0.0289997 | pos | 674 | | 39 | 1418 | 1953 |
| Kcnc1 | 0.0455174 | neg | | 3846 | 97 | 1624 | 2168 |
| Cyp2c40 | 0.0555593 | neg | | 1345 | 25 | 1804 | 918 |
| Rimbp3 | 0.0566486 | neg | | 56 | 85 | 1221 | 445 |
| 4921511H03Rik | 0.0739165 | pos | 48 | | 156 | 811 | 1213 |
| Chrm1 | 0.0870416 | neg | | 565 | 65 | 1610 | 2304 |
| Dmrta1 | 0.1088845 | neg | | 981 | 66 | 1459 | 2108 |
| Olfr187 | 0.1175577 | pos | 26 | | 133 | 2789 | 1779 |
| 4932429P05Rik | 0.1307935 | pos | 45 | | 1130 | 2142 | 1420 |
| Gja8 | 0.1370485 | neg | | 21 | 982 | 2244 | 2435 |
| Vmn1r212 | 0.1538853 | pos | 80 | | 215 | 120 | 116 |
| Cd7 | 0.1566941 | neg | | 168 | 38 | 648 | 860 |
| Atp10b | 0.1753225 | neg | | 10 | 1877 | 1218 | 538 |
| Csta | 0.1948054 | pos | 279 | | 58 | | |
| Pak6 | 0.198052 | neg | | 33 | 3141 | | |
| Caprin2 | 0.2385725 | neg | | 34 | 17 | 2783 | 1887 |
| Vmn2r2 | 0.2662511 | pos | 91 | | 1489 | 2245 | 2593 |
| Vmn1r71 | 0.3612206 | pos | 79 | | 175 | 2180 | 1248 |
| Olfr1253 | 0.3729281 | neg | | 23 | 619 | 2313 | 2359 |
| Nlrp4e | 0.3933181 | neg | | 14 | 190 | 1798 | 1965 |
| Olfr1497 | 0.4414086 | neg | | 11 | 458 | 2518 | 1787 |
| Bex1 | 0.4946157 | pos | 97 | | 994 | 1343 | 473 |
| Polq | 0.5050873 | neg | | 13 | 15 | 2071 | 1218 |
| Kctd1 | 0.5727475 | neg | | 194 | 80 | 1660 | 1730 |
| Amotl1 | 0.6152932 | neg | | 40 | 35 | 1130 | 405 |
| Prrg4 | 0.6311149 | neg | | 103 | 91 | 1317 | 835 |
| D3Bwg0562e | 0.6727203 | pos | 81 | | 96 | 937 | 1070 |
| Lrrc17 | 0.7831777 | pos | 71 | | 520 | 2373 | 2505 |
| Hist1h2bh | 0.952299 | pos | 1205 | | 79 | 107 | 161 |
| Arap2 | 1.0569792 | pos | 72 | | 315 | 590 | 828 |
| Suz12 | 1.2113286 | neg | | 171 | 55 | 716 | 912 |
| Invs | 1.2868174 | neg | | 1732 | 88 | 2166 | 2686 |
| Gtf2ird1 | 1.2930437 | neg | | 159 | 53 | 1002 | 1024 |

TABLE S4-continued

| geneID | mean expression | regulator | Rank according to positive z score | Rank according to negative z score | Rank according to DE | Z score secondary | DE score secondary |
|---|---|---|---|---|---|---|---|
| Atxn7l3 | 1.599496 | neg | | 2 | 13 | 25 | 40 |
| Lims2 | 1.6820134 | neg | | 188 | 78 | 1980 | 2140 |
| Dnttip1 | 1.6829178 | neg | | 5 | 24 | 93 | 121 |
| Rfwd2 | 1.8615258 | neg | | 12 | 37 | 33 | 49 |
| Pcf11 | 1.9287589 | pos | 68 | | 511 | 1995 | 1959 |
| Enox2 | 2.0973271 | pos | 102 | | 40 | 2346 | 1776 |
| Fdxacb1 | 2.1791234 | pos | 921 | | 93 | 1812 | 2167 |
| Rtf1 | 2.2229473 | pos | 57 | | 63 | 1853 | 822 |
| N4bp2l2 | 2.293882 | pos | 61 | | 47 | 1387 | 1276 |
| Ctcf | 2.4944746 | pos | 12 | | 10 | 14 | 13 |
| Limk1 | 2.5045586 | pos | 64 | | 333 | 927 | 1231 |
| Rbm27 | 2.6238947 | pos | 65 | | 216 | 1135 | 744 |
| Yy1 | 2.624785 | neg | | 4 | 36 | 32 | 45 |
| Nipbl | 2.7207485 | pos | 163 | | 30 | 63 | 72 |
| Ndor1 | 2.7604428 | pos | 265 | | 57 | 2737 | 2459 |
| Ncor2 | 2.794435 | neg | | 29 | 265 | 1622 | 1081 |
| Akirin2 | 2.8015294 | pos | 39 | | 74 | 55 | 59 |
| Fgd6 | 2.846561 | pos | 44 | | 3528 | | |
| Traf3 | 2.8761111 | pos | 89 | | 2218 | 130 | 112 |
| Tti2 | 2.8802275 | pos | 47 | | 247 | 2614 | 1937 |
| 2610301B20Rik | 2.8823901 | pos | 77 | | 2999 | | |
| Hmgn5 | 2.9097861 | pos | 92 | | 690 | 1959 | 1525 |
| Mycbp2 | 3.0889873 | neg | | 30 | 72 | 95 | 107 |
| Prps1l3 | 3.0940418 | neg | | 101 | 50 | 636 | 924 |
| B4galt5 | 3.1184623 | neg | | 17 | 415 | 1026 | 2280 |
| Ddx10 | 3.2385877 | pos | 40 | | 536 | 2618 | 1449 |
| Cul3 | 3.2608225 | pos | 46 | | 22 | 108 | 82 |
| C230052I12Rik | 3.270432 | neg | | 123 | 18 | 783 | 1610 |
| Ankrd10 | 3.3380866 | pos | 342 | | 94 | 2114 | 2122 |
| Ctr9 | 3.3595824 | pos | 25 | | 917 | 47 | 35 |
| Rara | 3.428654 | neg | | 6 | 32 | 129 | 111 |
| Mamld1 | 3.4559478 | neg | | 136 | 59 | 302 | 272 |
| Orc6 | 3.472132 | pos | 49 | | 405 | 176 | 233 |
| Eny2 | 3.4925085 | neg | | 52 | 41 | 975 | 1074 |
| Midn | 3.5320036 | pos | 30 | | 525 | 19 | 21 |
| Tirap | 3.6314516 | pos | 9 | | 16 | 6 | 6 |
| Ikbkg | 3.634915 | pos | 84 | | 168 | 314 | 185 |
| Tubgcp3 | 3.6735153 | neg | | 155 | 46 | 313 | 508 |
| Leo1 | 3.6903327 | pos | 32 | | 275 | 70 | 63 |
| Snip1 | 3.6937478 | pos | 99 | | 1501 | 1431 | 1007 |
| Rc3h1 | 3.7525108 | neg | | 3 | 23 | 24 | 38 |
| Alg2 | 3.8175829 | pos | 269 | | 87 | 91 | 67 |
| Stat5b | 3.8915391 | neg | | 9 | 48 | 41 | 60 |
| Ticam1 | 3.9907575 | pos | 8 | | 4 | 12 | 12 |
| Gabpb1 | 4.0809531 | pos | 38 | | 69 | 173 | 131 |
| Tipin | 4.1237736 | pos | 31 | | 590 | 1150 | 2059 |
| Ube3a | 4.1248275 | pos | 93 | | 563 | 719 | 1285 |
| Ash2l | 4.3523026 | pos | 41 | | 81 | 74 | 55 |
| Gpkow | 4.4343094 | pos | 53 | | 1440 | 236 | 157 |
| Rnf31 | 4.4432453 | pos | 42 | | 61 | 90 | 65 |
| Comtd1 | 4.4834476 | neg | | 19 | 42 | 428 | 502 |
| Traf6 | 4.5088665 | pos | 13 | | 64 | 31 | 41 |
| Ly96 | 4.5530913 | pos | 2 | | 2 | 1 | 3 |
| Wasf2 | 4.5534458 | pos | 85 | | 488 | 203 | 325 |
| Zfp36 | 4.5864576 | neg | | 1 | 6 | 9 | 10 |
| BC023829 | 4.5949364 | pos | 58 | | 98 | 676 | 883 |
| Ikzf1 | 4.6416247 | pos | 22 | | 51 | 97 | 78 |
| Ticam2 | 4.6788326 | pos | 5 | | 3 | 7 | 7 |
| Xab2 | 4.7360399 | pos | 18 | | 825 | 1923 | 886 |
| Traf2 | 4.8029788 | pos | 96 | | 1171 | 193 | 190 |
| Map3k8 | 4.8837956 | pos | 52 | | 492 | 20 | 22 |
| Traf5 | 4.8850542 | neg | | 192 | 49 | 738 | 1332 |
| Mapkapk2 | 4.944774 | pos | 36 | | 2075 | 36 | 27 |
| Sgms1 | 4.9819627 | pos | 37 | | 105 | 11 | 11 |
| Paf1 | 5.0227227 | pos | 27 | | 29 | 40 | 34 |
| Prpf40a | 5.0238077 | pos | 50 | | 1076 | 475 | 1088 |
| Fam50a | 5.0268849 | neg | | 71 | 27 | 77 | 98 |
| Ruvbl2 | 5.1008998 | pos | 83 | | 1255 | 384 | 725 |
| Dr1 | 5.1128304 | pos | 90 | | 1150 | 137 | 100 |
| Ikbkb | 5.189822 | pos | 23 | | 638 | 46 | 43 |
| Vps41 | 5.2563794 | pos | 78 | | 1527 | 163 | 99 |
| Gtf2h1 | 5.2863726 | pos | 75 | | 3245 | | |
| Dusp1 | 5.5754287 | neg | | 7 | 286 | 94 | 95 |
| Fam96b | 5.5833555 | pos | 69 | | 1151 | 1637 | 1724 |
| Pitpnb | 5.5942627 | neg | | 308 | 43 | 507 | 271 |

TABLE S4-continued

| geneID | mean expression | regulator | Rank according to positive z score | Rank according to negative z score | Rank according to DE | Z score secondary | DE score secondary |
|---|---|---|---|---|---|---|---|
| Irf9 | 5.7146257 | neg | | 95 | 28 | 1141 | 832 |
| Dhx15 | 5.7329351 | pos | 70 | | 163 | 56 | 53 |
| Wdr61 | 5.7932784 | pos | 51 | | 34 | 54 | 48 |
| Nans | 5.8843053 | neg | | 5678 | 56 | 1432 | 596 |
| Strap | 5.9195968 | neg | | 25 | 479 | 115 | 148 |
| Pdcd10 | 5.957733 | neg | | 32 | 2484 | 79 | 87 |
| Polr2j | 5.9933101 | pos | 192 | | 45 | 409 | 236 |
| 0610009D07Rik | 6.0487871 | pos | 87 | | 339 | | |
| Tlr4 | 6.0828205 | pos | 10 | | 8 | 3 | 2 |
| Srpr | 6.1576415 | pos | 55 | | 1283 | 18 | 17 |
| Rbck1 | 6.1623505 | pos | 19 | | 92 | 38 | 37 |
| Eif5 | 6.1717398 | neg | | 8 | 106 | 269 | 200 |
| Becn1 | 6.1995961 | neg | | 24 | 107 | 1774 | 2714 |
| Srp54c | 6.2094334 | pos | 17 | | 19 | 145 | 120 |
| Polr2g | 6.2287455 | pos | 29 | | 33 | 1331 | 2099 |
| Cebpb | 6.230226 | pos | 21 | | 183 | 37 | 29 |
| Eif2s1 | 6.2619052 | neg | | 35 | 86 | 178 | 332 |
| Cd69 | 6.2908584 | pos | 100 | | 140 | 921 | 1816 |
| Rela | 6.3060629 | pos | 11 | | 70 | 29 | 26 |
| Brd2 | 6.3398195 | pos | 67 | | 988 | 22 | 19 |
| Rpl26 | 6.3680742 | pos | 62 | | 678 | 870 | 2486 |
| Rbx1 | 6.3778141 | pos | 15 | | 130 | 35 | 50 |
| Gtf2b | 6.4532102 | pos | 28 | | 77 | 111 | 94 |
| Rbms1 | 6.7376793 | pos | 82 | | 248 | 188 | 141 |
| Fkbp8 | 6.8721672 | pos | 74 | | 60 | 1241 | 1701 |
| Napa | 6.9841007 | pos | 43 | | 259 | 243 | 321 |
| Lcp2 | 6.9993322 | neg | | 27 | 408 | 1225 | 2241 |
| Ddx39b | 7.1022769 | pos | 24 | | 84 | 102 | 91 |
| Mmp14 | 7.1973532 | neg | | 31 | 238 | 2337 | 1869 |
| Rpn1 | 7.244059 | pos | 14 | | 12 | 45 | 42 |
| Myd88 | 7.293524 | pos | 4 | | 7 | 5 | 5 |
| Sec13 | 7.3392971 | pos | 86 | | 241 | 1094 | 1837 |
| Rap1b | 7.3583281 | neg | | 80 | 67 | 2400 | 2764 |
| Copz1 | 7.4459878 | pos | 59 | | 52 | 312 | 575 |
| Pabpc1 | 7.5733642 | pos | 16 | | 11 | 26 | 25 |
| Tmem258 | 7.7332655 | pos | 20 | | 20 | 59 | 56 |
| Rpn2 | 7.7429485 | pos | 73 | | 21 | 16 | 15 |
| Ppp2r1a | 7.8447585 | neg | | 16 | 89 | 60 | 73 |
| Ddost | 7.8512283 | pos | 7 | | 9 | 27 | 20 |
| Pla2g7 | 7.851729 | neg | | 18 | 31 | 2744 | 2441 |
| Psma1 | 7.9129454 | pos | 98 | | 491 | 350 | 419 |
| Dad1 | 7.951084 | pos | 6 | | 14 | 21 | 23 |
| Cyc1 | 8.0641757 | pos | 76 | | 836 | 254 | 577 |
| Cxcl1 | 8.0704161 | neg | | 20 | 119 | 1366 | 1272 |
| Hsp90b1 | 8.3326208 | pos | 63 | | 371 | 8 | 8 |
| Hspa5 | 9.1655412 | neg | | 28 | 199 | 1894 | 1462 |
| Cd14 | 9.2997102 | pos | 3 | | 5 | 2 | 1 |
| Tnf | 9.5646516 | pos | 1 | | 1 | 4 | 4 |
| Rpl23a | 10.030421 | pos | 56 | | 116 | 401 | 709 |
| Rpl35 | 10.140576 | pos | 35 | | 984 | 656 | 1258 |
| Bcl2a1d | 10.233762 | pos | 66 | | 54 | 385 | 138 |
| Rpl10 | 10.551308 | pos | 33 | | 62 | 1217 | 2240 |
| Actb | 12.886427 | pos | 34 | | 26 | 157 | 124 |

TABLE S5

| Gene | T0 | T2 | T4 | T6 |
|---|---|---|---|---|
| 2610301B20Rik | 3.59876844 | 3.25468716 | 2.14134 | 2.84581507 |
| Akirin2 | 1.6192359 | 2.86345589 | 3.36476434 | 3.03855652 |
| Ankrd10 | 4.27960239 | 3.43453893 | 2.79383714 | 3.1409302 |
| Bcl2a1d | 9.20384008 | 10.2458505 | 10.4774568 | 10.7170906 |
| Cd14 | 7.08060949 | 9.31056935 | 9.6927011 | 10.4840348 |
| Cd69 | 2.69085118 | 5.55296277 | 7.71699892 | 7.96321992 |
| Cebpb | 2.33457117 | 5.28970561 | 7.34979222 | 8.56507076 |
| Comtd1 | 5.12234817 | 4.75737235 | 4.37097649 | 3.94390077 |
| Cxcl1 | 1.69661341 | 10.3080308 | 10.018053 | 9.07719912 |
| Dusp1 | 4.39095914 | 6.34739988 | 5.45492375 | 5.9905752 |
| Fam50a | 5.46711418 | 5.28607528 | 5.10204733 | 4.4521369 |
| Hist1h2bh | 2.20278126 | 0 | 0.6972268 | 0.99438314 |
| Hspa5 | 8.13358536 | 8.48434499 | 9.0473677 | 10.5073946 |

TABLE S5-continued

| Gene | T0 | T2 | T4 | T6 |
|---|---|---|---|---|
| Ikzf1 | 3.83148641 | 4.59111207 | 4.95848369 | 4.93951629 |
| Lcp2 | 6.20277561 | 7.02550143 | 7.31363177 | 7.23530939 |
| Mamld1 | 2.5721264 | 3.08617137 | 4.0226817 | 3.78464096 |
| Map3k8 | 3.87949528 | 5.30199185 | 5.28981525 | 4.89642164 |
| Mapkapk2 | 3.94479949 | 4.82187436 | 5.37761792 | 5.3139832 |
| Mmp14 | 5.11800801 | 6.85111462 | 7.86396703 | 8.26329919 |
| Orc6 | 4.13341473 | 3.88486879 | 3.41557055 | 2.76153649 |
| Polr2j | 6.56600865 | 6.09343076 | 5.95384903 | 5.55218587 |
| Rap1b | 6.01668665 | 6.8397286 | 7.86032221 | 8.18507744 |
| Rara | 4.59846846 | 3.4938824 | 3.26283613 | 2.71229852 |
| Rc3h1 | 2.87911131 | 3.89289845 | 4.3435479 | 3.68505367 |
| Rela | 5.48314301 | 6.42518513 | 6.56259762 | 6.55224096 |
| Rfwd2 | 1.3978399 | 1.51327281 | 1.80142272 | 2.50158524 |
| Rnf31 | 3.82081029 | 3.83809782 | 4.76436352 | 4.99897175 |
| Rpl26 | 6.0476079 | 5.74366969 | 7.26668418 | 6.14437196 |
| Ruvbl2 | 5.67150918 | 5.51888681 | 4.8716344 | 4.62402482 |
| Sgms1 | 4.66284182 | 5.72875332 | 4.90355104 | 4.75489607 |
| Tipin | 4.75098412 | 4.93786879 | 3.98640209 | 3.23164093 |
| Tnf | 5.48222936 | 11.1409658 | 10.9011026 | 10.0182778 |
| Traf3 | 1.81688289 | 3.29774043 | 3.02805346 | 3.17959655 |
| Traf5 | 3.74527722 | 4.92651491 | 5.32673695 | 5.22788295 |
| Yy1 | 1.99748107 | 2.0793673 | 2.82227287 | 3.2649555 |

Strikingly, the top-10 ranking positive regulator genes (ZS analysis,) are almost exclusively populated by the hallmark members of TLR signaling, with many others among the top-100, showing that an unbiased, genome-wide screen can decipher near-complete pathways (FIG. 19B). Tnf was the highest ranking, demonstrating the screen's quantitative nature. Key regulators of the LPS response with top ranks in the screen include (FIG. 19B): Tlr4 (rank 10) and its co-receptors Ly96 (MD2) (rank 2) and Cd14 (rank 3); well-known members of LPS/Tlr4 signaling, including Ticam2 (TRAM, rank 5), Ticam1 (TRIF, rank 8), Myd88 (rank 4), Tirap (rank 9), and Traf6 (rank 13); Rela (rank 11), a component of NFKB, which regulates Tnf transcription; and two regulators of NFKB: Ikbkb and Ikbkg (NEMO) (rank 23 and rank 84, respectively). Other notable known regulators of the immune response and DC function include the DC pioneer transcription factor Cebpb (rank 21), Akirin2 (rank 39) (Goto et al., 2008; Tartey et al., 2014), and Rnf3 1 (rank 42) and Rbck1 (rank 19), two subunits of the linear ubiquitin chain assembly complex (LUBAC) that tags Ikbkg and enables NFKB activation (Tokunaga et al., 2011). Overall, the top-100 ranked genes were highly enriched for central genes in the LPS to Tnf pathway as annotated by KEGG (13/35 annotated genes are in the top 100; $P=10^{-12}$, Hypergeometric test). Taken together, these results demonstrate that CRISPR-Cas9 genetic screens are effective at identifying key components of a pathway in primary immune cells, and are compatible with flow cytometry assays for protein levels.

Dozens of positive regulators identified by the screen validated using individually-cloned sgRNAs. While the top-ranking genes are highly enriched for known regulators, they also include genes that were not previously associated with either Tlr4 signaling, the LPS response, or regulation of Tnf. For example, within the top-10 ranking genes, eight are bone-fide members of the Tlr4 signaling pathway, whereas the other two genes are subunits of the oligosaccharyltransferase complex (OSTc), a complex responsible for protein glycosylation (discussed below). Some of these highly ranked genes could be novel regulators, but others may be false positives.

To distinguish these possibilities and empirically determine the true positive rate in the top hits, Applicants next individually tested the top-100 putative positive regulators and top 35 putative negative regulators based on the Z score ranking, and the 98 top putative regulators (52 positive and 46 negative) based on the differential abundance analysis (57 genes overlap between the two sets). In this strategy Applicants took all positive regulators within a relatively permissive FDR in the initial screen (112 top positive regulators, an estimated FDR of ~50%), but extensively test each of those genes, to find as many validated regulators as possible within the limits of scale for testing. In total, Applicants tested 176 hit genes (112 putative positive regulators; 64 putative negative regulators, the latter not considered in the FDR above) with individual, rather than pooled, targeting of each gene with each of 2-3 independent sgRNAs, to a total of 400 individual targeting sgRNA assays (245 and 155 sgRNAs for positive and negative regulators, respectively), and 53 non-targeting controls. Applicants tested the effect of each of the 453 sgRNA by measuring intracellular Tnf levels by flow cytometry (FIG. 19A). Applicants conservatively compared the effect of each sgRNA that targets a putative regulator to the two non-targeting sgRNA with the most extreme effects in the same experimental batch (Experimental Procedures). For analyzing Tnf levels Applicants gated on live cells, and excluded from the analysis sgRNAs that cause significant reduction in viability (Table S7, Experimental Procedures).

Approximately half of the sgRNAs that target putative positive regulator genes (111 sgRNAs, 45%, FIG. 19C, blue dots, Table S6 and S8), including those for key known regulators (FIG. 19B right), were confirmed as functional, suggesting a good true positive rate in the primary screen. Overall, Applicants verified 57 positive regulators out of 112 ones tested: 45 with at least two independent sgRNAs and another 12 genes with one sgRNA (Table S6). Indeed, the true positive rate at each rank throughout the top 100 genes agrees remarkably well with the predicted FDR (FIG. 19E), supporting the value and accuracy of the statistical framework. Furthermore, there is a strong positive (albeit non-linear) relation between the original gene ranking in the screen and the mean shift in Tnf expression in the validation experiment, such that better ranked genes were more likely to be successfully validated (FIG. 19D). Notably, 27/57 validated genes are not previously annotated for immune function or Tnf regulation in any of five major databases (Immport (Bhattacharya et al., 2014), IRIS (Kelley et al., 2005), Immunome (Ortutay and Vihinen, 2006), MAPK-NFkB network (Lynn et al., 2008), and KEGG's TLR pathway (Kanehisa and Goto, 2000); Table S9).

TABLE S6

| all "positive" guides tested | genes tested | true positive guides | true positive genes based on one guide | true positive genes based on more than one guide |
|---|---|---|---|---|
| 0610009D07Rik%%MGLibA_00009 | 0610009D07Rik | 0610009D07Rik%%MGLibA_00009 | Fdxacb1 | 0610009D07Rik |
| 0610009D07Rik%%MGLibB_00008 | 2610301B20Rik | 0610009D07Rik%%MGLibB_00008 | Lrrc17 | Akirin2 |
| 2610301B20Rik%%MGLibA_00936 | 4921511H03Rik | Akirin2%%MGLibA_03653 | Mapkapk2 | Alg2 |
| 2610301B20Rik%%MGLibB_00936 | 4932429P05Rik | Akirin2%%MGLibB_03652 | mmu-mir-106a | Ash2l |
| 4921511H03Rik%%MGLibB_01150 | Actb | Alg2%%MGLibA_03837 | mmu-mir-466c-2 | Cd14 |
| 4921511H03Rik%%MGLibB_01151 | Akirin2 | Alg2%%MGLibB_03837 | Ruvbl2 | Cebpb |
| 4932429P05Rik%%MGLibA_01501 | Alg2 | Ash2I%%MGLibA_05467 | Srp54c | Ctcf |
| 4932429P05Rik%%MGLibA_01502 | Ankrd10 | Ash2I%%MGLibB_05467 | Traf2 | Ctr9 |
| Actb%%MGLibB_02796 | Arap2 | Cd14%%MGLibA_08997 | Traf3 | Dad1 |
| Actb%%MGLibB_02797 | Ash2I | Cd14%%MGLibB_08997 | Tti2 | Ddost |
| Akirin2%%MGLibA_03653 | BC023829 | Cd14%%MGLibB_08998 | Ube3a | Ddx39b |
| Akirin2%%MGLibB_03652 | Bcl2a1d | Cebpb%%MGLibA_09728 | Vmn1r71 | Gpkow |

TABLE S7

| Guides that cause reduction in cell viability | Low cell number (virus production) | inconsistent phenotype |
|---|---|---|
| Actb%%MGLibB_02796 | Fgd6%%MGLibB_18286 | 4921511H03Rik%%MGLibB_01150 |
| Actb%%MGLibB_02797 | Limk1%%MGLibA_28954 | Copz1%%MGLibA_11492 |
| BC023829%%MGLibA_06281 | Napa%%MGLibA_33247 | Copz1%%MGLibB_11490 |
| Cul3%%MGLibA_12475 | Napa%%MGLibB_33238 | Dhx15%%MGLibA_14101 |
| Cul3%%MGLibA_12476 | Orc6%%MGLibA_38964 | Gabpb1%%MGLibB_19241 |
| Cul3%%MGLibA_12472 | Psma1%%MGLibA_43357 | Hist1h2bh%%MGLibA_24282 |
| Ddx10%%MGLibB_13564 | Rpl10%%MGLibB_46136 | Hist1h2bh%%MGLibB_24272 |
| Rbm27%%MGLibA_44791 | Rpl26%%MGLibB_46188 | Mapkapk2%%MGLibB_30381 |
| Rbx1%%MGLibB_44894 | Srp54c%%MGLibB_51302 | Pcf11%%MGLibB_39906 |
| Ruvbl2%%MGLibB_46746 | Traf3%%MGLibA_55551 | Prpf40a%%MGLibA_43020 |
| Snip1%%MGLibB_50292 |  | Rbx1%%MGLibB_44896 |
| Tipin%%MGLibA_53942 |  | Rpl23a%%MGLibA_46191 |
| Tipin%%MGLibB_53927 |  | Snip1%%MGLibA_50308 |
| Xab2%%MGLibB_59663 |  | Steap4%%MGLibB_51716 |
| Xab2%%MGLibB_59664 |  | Tti2%%MGLibA_56492 |
|  |  | Vmn2r2%%MGLibA_58692 |

Applicants also explored the basis for false negatives among the positive regulators by examining known regulators of LPS activation that were not among the top-100 ranked genes in the screen. False negatives may arise simply from the limited number of cells relative to number of sgRNAs screened, affecting their ranking, or from sgRNAs that are less efficient at targeting (Doench et al., 2014). To address the latter possibility, Applicants used a different algorithm (Doench et al., 2014) to design 28 additional sgRNAs to target 15 known regulators in the LPS activation pathway that did not rate in the top hits (as chosen above) in the screen. Of these, 12 sgRNA targeting 8/15 genes affected Tnf expression: Irak1 (ranked 992), Irak2 (not scored in the initial library given due to low guide abundance), Irak4 (ranked 187), Tab2 (ranked 1,077), Nfkb2 (ranked 490), Nfkbia (ranked 1,753), Nfkbib (ranked 4,451) and Chuk (ranked 1,948) (FIG. 28A). For 6/15 known regulators not recovered in the primary screen the two additional sgRNAs still had no observable effect (FIG. 28B, Nfkbie (ranked 8,669), Relb (ranked 13,909), Tab3 (ranked 5,234), Map2k4 (ranked 18,314), Map2k6 (ranked 2,871), and Map2k7 (ranked 14,578)), whereas both sgRNAs targeting Map3k7 (ranked 735) (Tak1) caused substantial cell death (not shown). Notably, the eight known regulators with an effect in this additional test were more highly ranked (187-4,4517) than the remaining seven genes (2,871-18,314), suggesting that lower-ranked genes may still have substantial functional impact in this complex response.

Overall, Applicants conclude that for the predicted 112 positive regulators of Tnf the false positive rate is 55% and the estimation for the false negatives in the screen based on the known genes that are not in the top 100 ranks is around 53%.

Optimized characterization of novel negative regulators by analysis at unsaturated levels of Tnf Only four of the 64 (FIG. 28C, Table S10) putative negative regulators were initially validated individually by two independent sgRNAs: Zfp36 (rank 1 among the ZS negative regulators, FIG. 18A), Stat5b (rank 9), Pdcd10 (CCM3, rank 32), and Ppp2r1a (rank 16). Each of these, including Zfp36, the known control, associates with human disease. First, Stat5b, a transcription factor activated in response to cytokine induction (Darnell, 1997), is important for DC differentiation (Sebastian et al., 2008) (consistent with a low-Cd11c phenotype in its targeted cells; FIG. 28E), but was not previously implicated in regulation of Tnf induction in differentiated DCs. Stat5b deficiency in humans is associated with autoimmune disease (Kanai et al., 2012), leukemia (Raj ala et al., 2014) and solid tumors (Joung et al., 2008; Lim et al., 2012). Pdcd10 (CCM3), was not previously reported to regulate TNF, and is associated with familial Cerebral Cavernous Malformations (CCM) (Faurobert and Albiges-Rizo, 2010), a vascular pathological condition that can damage the central nervous system and cause stroke or death. Pdcd10 (CCM3) was also found to physically interact with the fourth negative regulator Ppp2r1a (Goudreault et al., 2009). Interestingly, Calyculin A, a drug that inhibits the protein phosphatase1 and protein phosphatase 2A complexes, of which Ppp2r1a is a member, was previously shown to induce TNF secretion (Boehringer et al., 1999).

The small proportion of validated negative regulators and their relatively subtle phenotype (FIG. 28C) suggested that, as noted above, the screen, conducted with a high (100 ng/ml) LPS concentration that leads to near-saturated Tnf levels, may be less sensitive for further induction of Tnf when perturbing negative regulators. Applicants therefore reduced LPS to 20 ng/ml to find a stronger impact of negative regulators on Tnf, reflected in either a higher proportion of expressing cells, a higher expression in expressing cells, or both (FIG. 28D). While this test is different from the initial screen and thus no longer allows us to assess the FDR for negative regulators in the screen, Applicants hoped that it would allow us to determine a function for some of the additional candidate negative regulators. Indeed, re-testing 37 sgRNAs targeting 22 genes in this unsaturated condition, 24 (65%) sgRNAs targeting 18 genes were shown to act as negative regulators, six with two sgRNAs (Table S10). These include the translation initiation factor Eif5 and the DNA binding protein and Rela-homolog (Yamashita et al., 2001) Dnttip1 (TdIF1) (two sgRNAs for each, FIG. 28D), neither previously implicated with immune response or Tnf regulation.

A secondary pooled screen uncovers additional regulators with greater sensitivity and specificity The analysis shows that a genome-wide screen can successfully recover known and novel regulators, and suggests that (for the positive regulators), noise in the screen may arise primarily from the large number of sgRNAs screened in a pool in a limited number of cells. In particular, 6 out of 7 of the false negative genes above (defined as known positive regulators that did not hit in the top-0.5% (i.e. top 100; FDR=50%, ZS analysis) in the genome-wide screen but were verified with individual sgRNAs), were rated in the top 10% of genes in the screen (FDR=96% for the positive ZS analysis). Applicants reasoned that the relatively low ranking of these false negatives may result from low sampling of the sgRNA due to the size of the library relative to the limited number of primary cells and the need for sorting cells to select for low vs. high TNF levels. In addition, the false negative analysis suggested that additional sgRNAs with improved design can improve the assay's sensitivity.

To address these complexity challenges, and uncover additional regulators, Applicants performed a secondary pooled screen targeting 2,569 genes based on the top ranked genes from the genome-wide screen with each of 10 different sgRNAs (with the improved design of (Doench et al., 2014)). The new library contained 28,010 sgRNA (1.66-fold more sgRNAs per gene than the primary screen), including 2,500 non-targeting sgRNAs controls. Applicants used the same number of cells (200×106), resulting in 4.9-fold more cells per sgRNA.

Figure 24A:
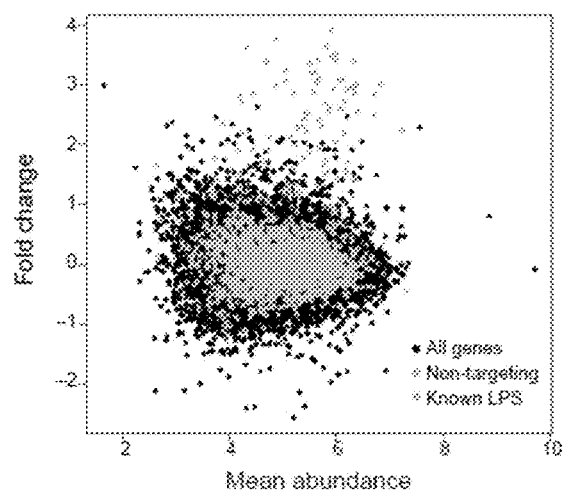
FIG. 24A-D Analysis of secondary screen. (A-B) sgRNAs targeting known regulators of LPS response (orange) have highly significant Z-scores, compared to other genes (black) and non-targeting controls (grey). Shown are MA-plots that relate for either sgRNAs (A) or genes (B) the z-score calculated fold-change between $TNF^{hi}$ and $TNF^{low}$ (Y axis) to the mean abundance of the sgRNA or gene (X axis). (C) Top ranked screen hits compare well between the DE and ZS approaches. Scatter plot compares the ranks of each gene by the DE (Y axis) and ZS (X axis) approaches, for the top ranked 200 genes, of which they share 170. The Spearman rank correlation coefficient is noted at the upper left corner. (D) Secondary screen improves specificity. Shown are the theoretically estimated FDRs (Y axis), based on shuffling the guides before collapsing to genes, for the secondary screen (orange) and the primary screen (calculated as elsewhere based on top 4 sgRNAs, black; or according to all sgRNAs, grey). The empirical FDR for the first screen, as determined by validation experiment, is marked by light blue at all ranks up to 100.
Figure 24B:
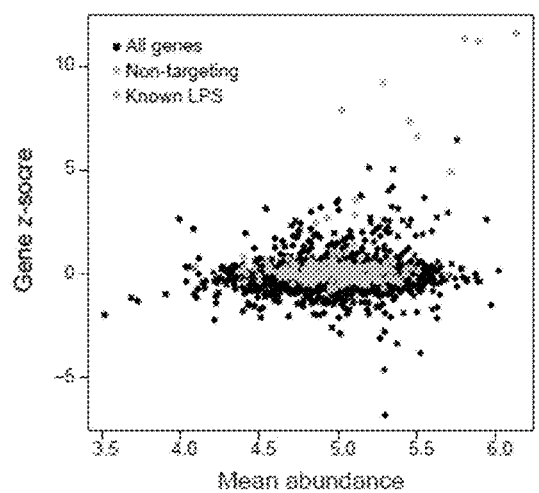
Figure 24C:
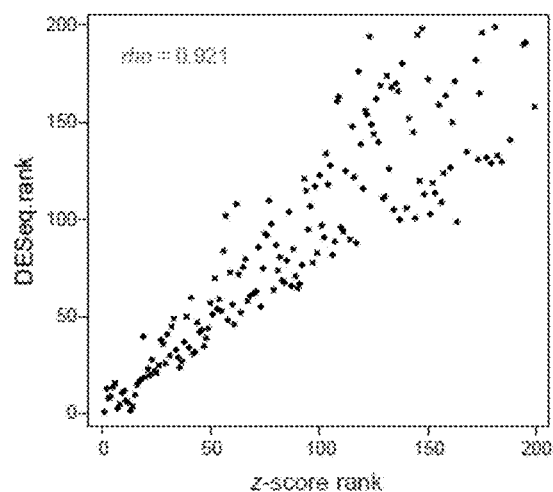
Figure 24D:
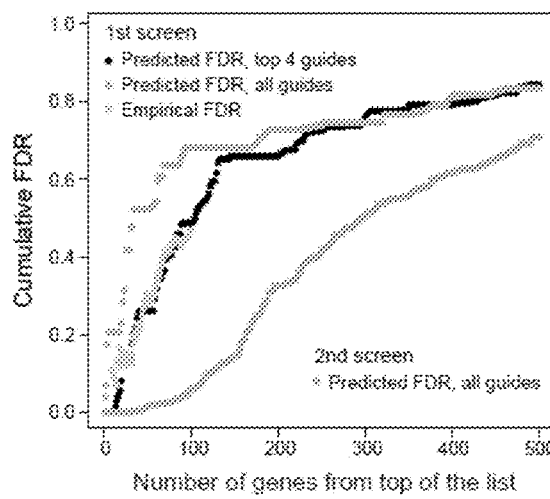

The secondary screen yielded more specific and sensitive results. On the one hand, a greater proportion of the known regulators were even more highly enriched in the Tnf-Low vs. Tnf-high libraries, (FIGS. 24A and 24B). The ranks from the ZS and DE analyses were highly correlated (Spearman ρ=0.92, FIG. 24C, Table S11 and S12), indicating that when noise is reduced, their solutions converge. The FDR was significantly smaller compared to the genome wide screen (e.g., FDR=6.7% at top-100 genes, FIG. 24D), with a much clearer inflection, leading to greater enrichment for true regulators. Among the new genes that ranked high in the secondary library were Irak1 (ranked 9 in the secondary screen vs. 187 in the primary screen) Irak4 (ranked 60 versus 992), Sharpin (another subunit of the LUBAC complex, ranked 36) and NEDD8 (ranked 52) and its E2 conjugation enzyme, Ube2f (ranked 25). Neddylation was shown to affect the secretion of cytokines by dendritic cells as well as their ability to activate T cells (Mathewson et al., 2013). The secondary screen also uncovered 21 regulators (Z>1.5 FDR=0.094) that had no prior immune annotation (Table S13) and were not found in the genome-wide screen, including genes with unknown function (e.g., Gpatch8). Thus, the secondary screen overcame some intrinsic limitations of the primary screen, including insufficient numbers of sgRNAs per genes and cells per sgRNAs. Following up a genome-wide screen with a higher depth secondary screen thus represents an effective strategy for maximizing CRISPR-based pooled screens in any biological system that has limits on the number of cells per screen.

Figure 25A:
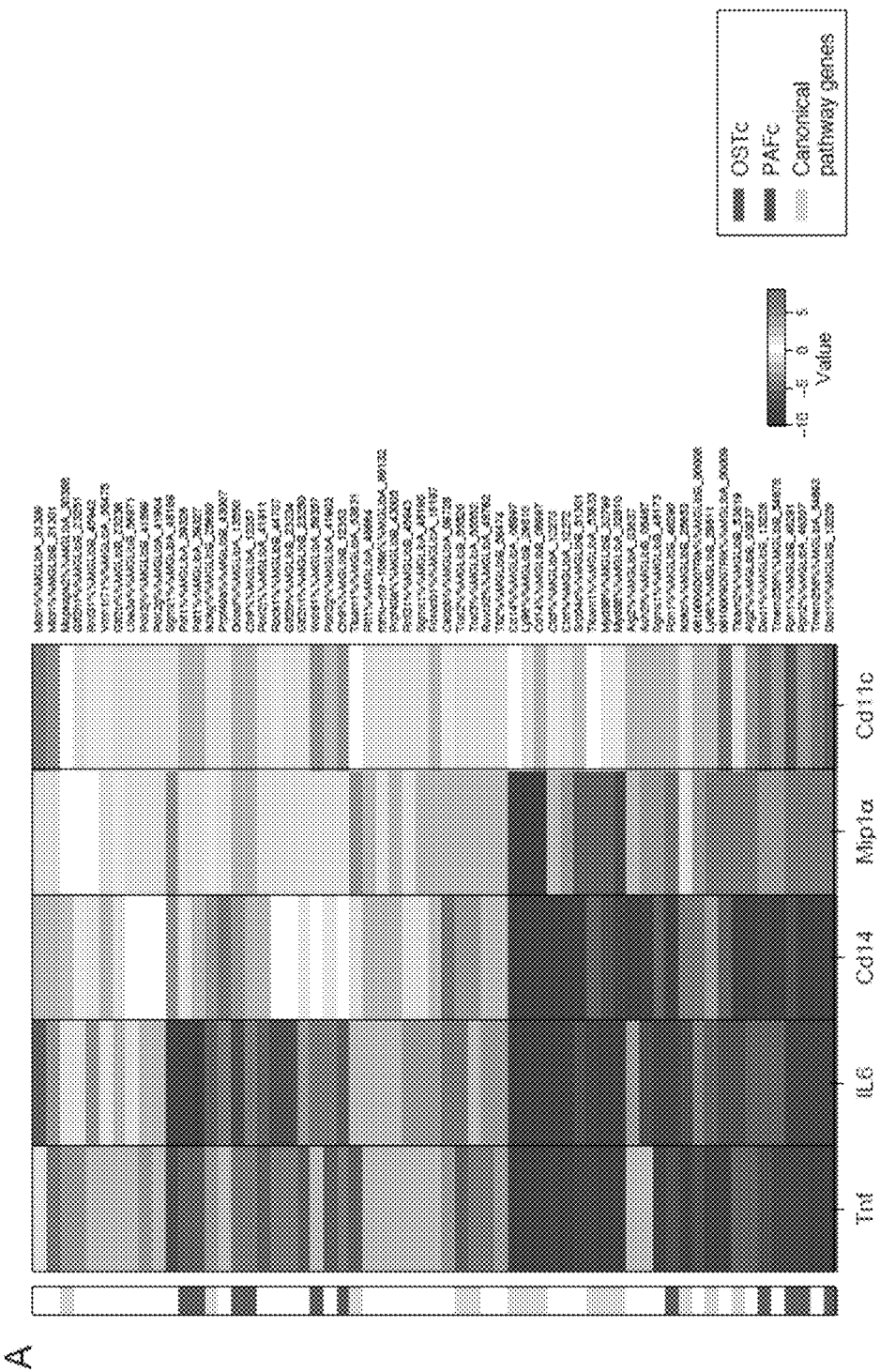
FIG. 25A-E Partitioning of the validated positive regulators into key modules by their effect on protein markers and RNA profiles. (A) Positive regulators group by distinct effects on protein expression. For each sgRNA targeting a positive regulator (rows) shown are its effects (Z score for each marker compared to non-target sgRNA; Experimental Procedures) on the expression of each of five proteins (columns) measured by staining with antibodies (Experimental Procedures). Three broad categories of responses can be defined, each preferentially associated with distinct proteins. Based on this matrix, sgRNAs were collapsed to score gene level effects as in FIG. 3A. (B-E) Positive regulators partition to modules based on their effect on mRNA profiles over time. Shown are clustered correlation matrix of verified positive regulators (rows, columns) based on global RNA expression profiles in cells where the regulator is targeted relative to non-targeting control (Experimental Procedures). Data from each time point is analyzed and clustered (B) t=0 h; (C) t=2 h; (D) t=4 h; (E) t=6 h). Genes in 3 key categories are color coded as in (A). Color bar is the Pearson correlation coefficient. Matrices are exactly as shown in FIG. 3D-F, except that a matrix is also shown for t=6 h, and that gene names are labeled.
Figure 25B:
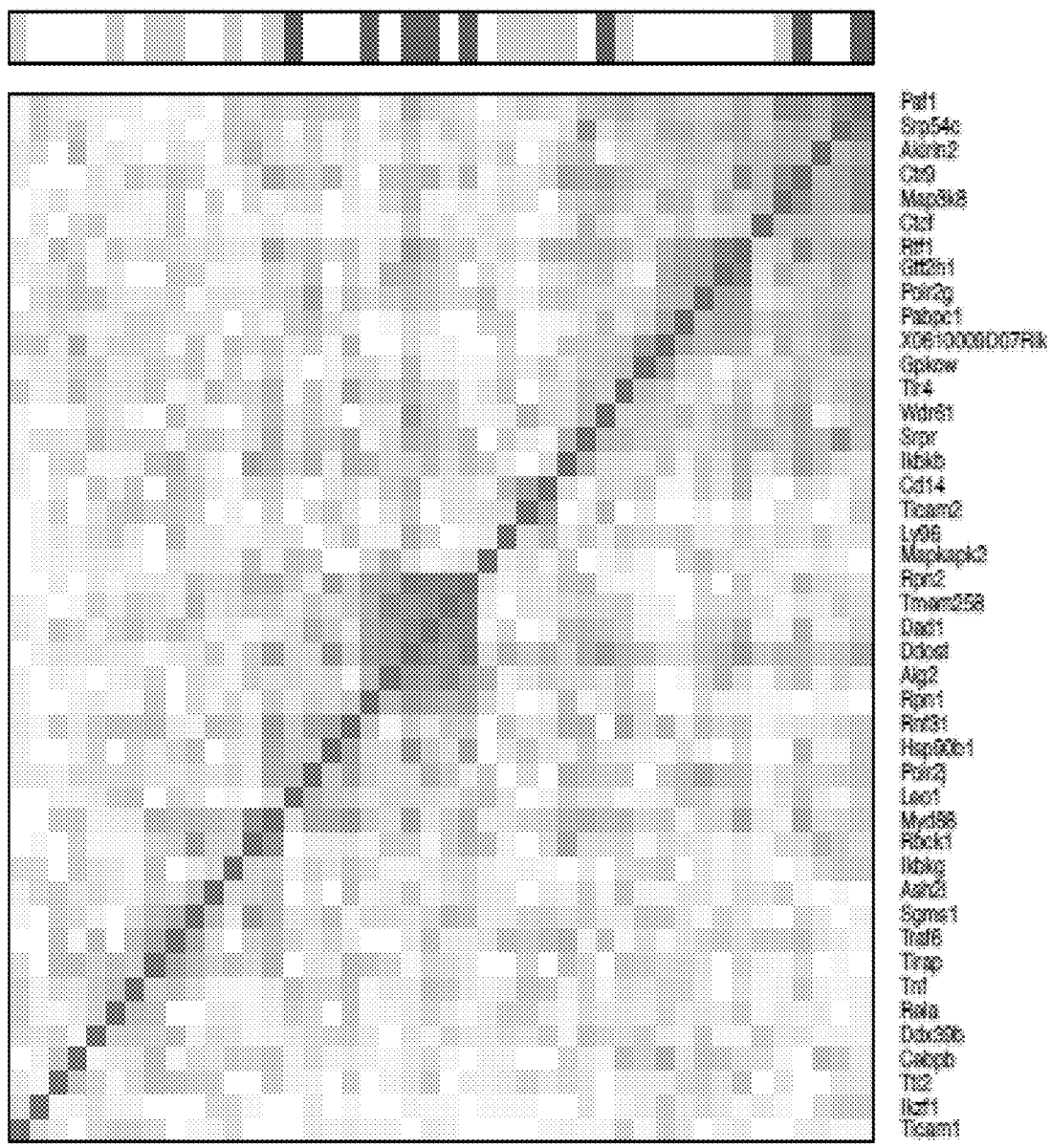
Figure 25C:
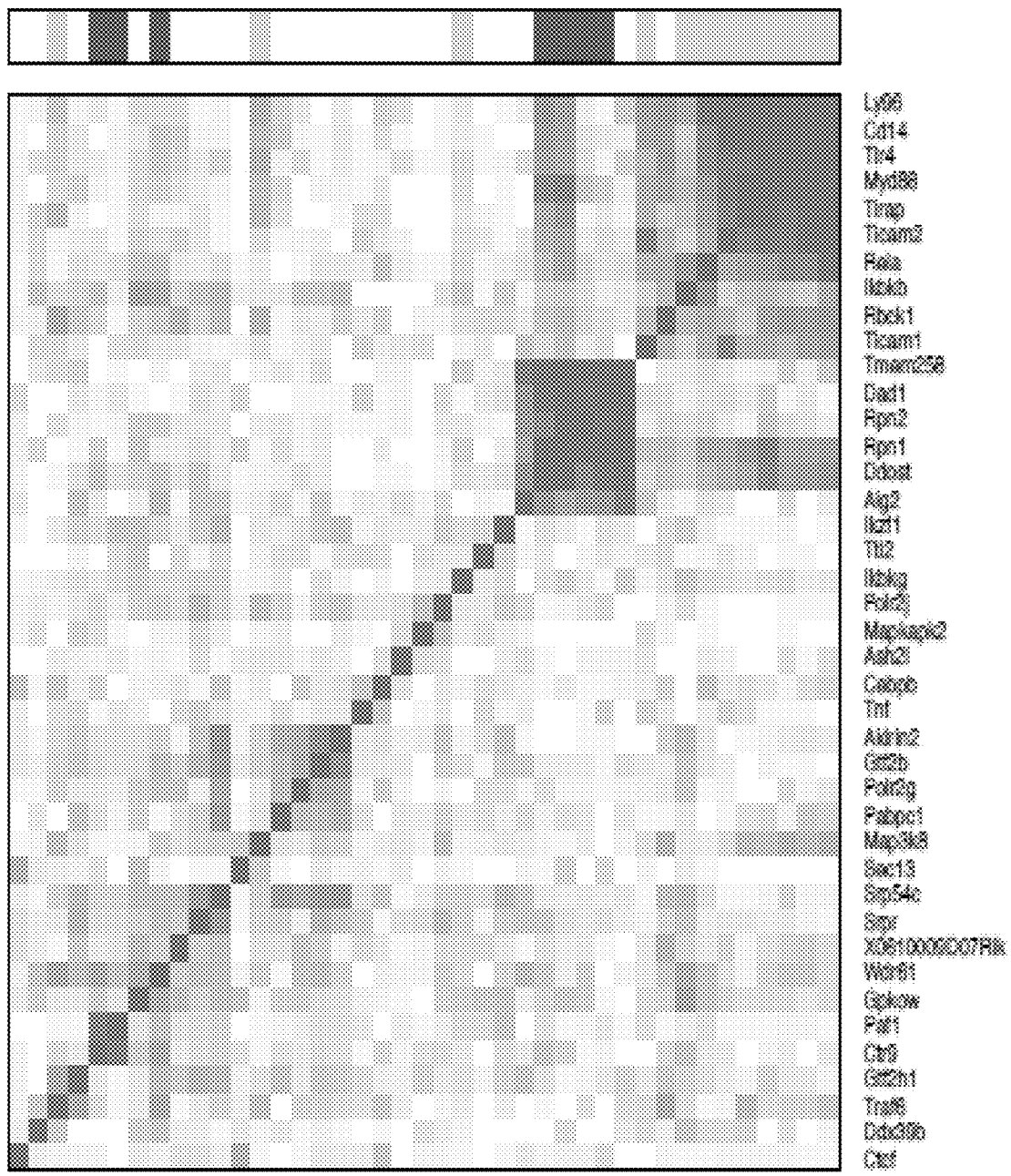
Figure 25D:
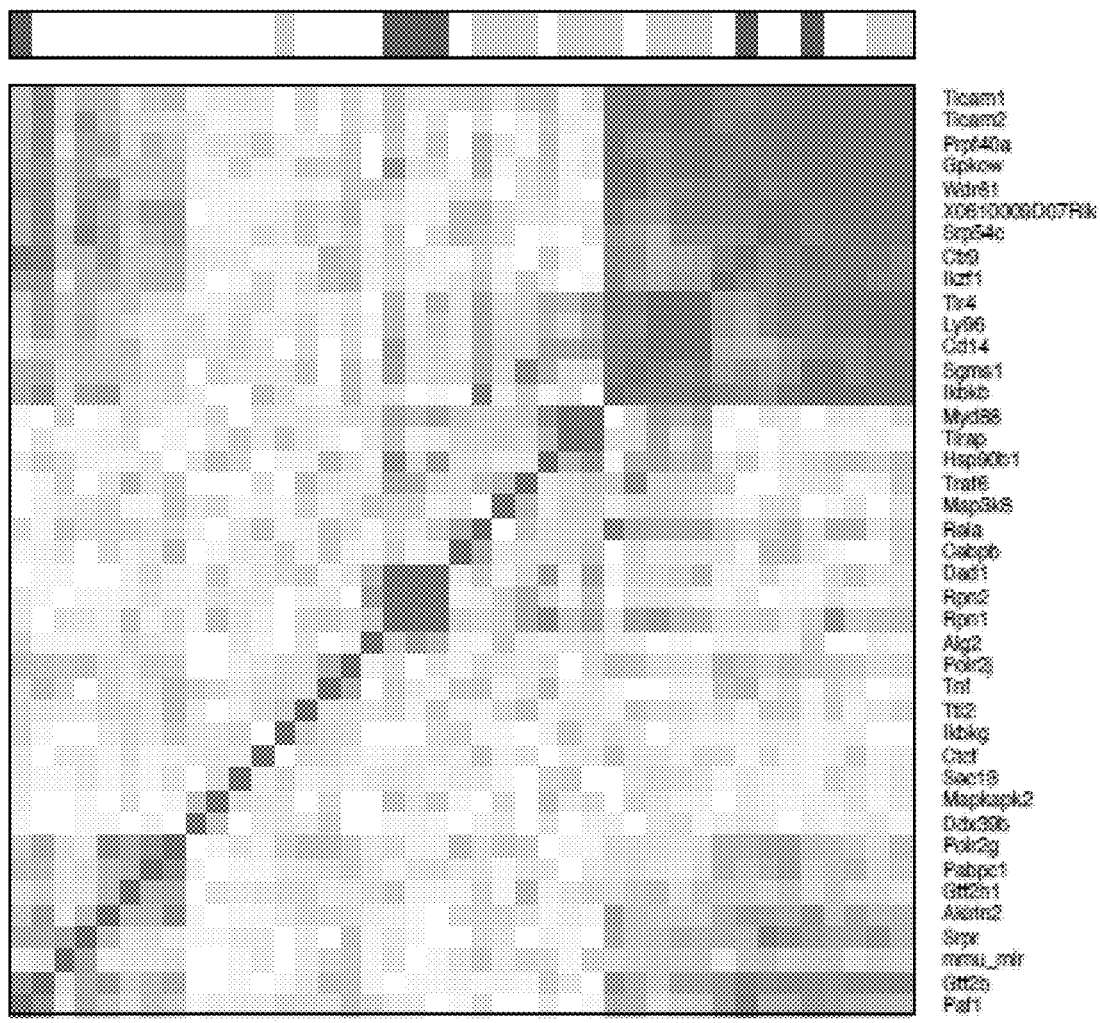
Figure 25E:
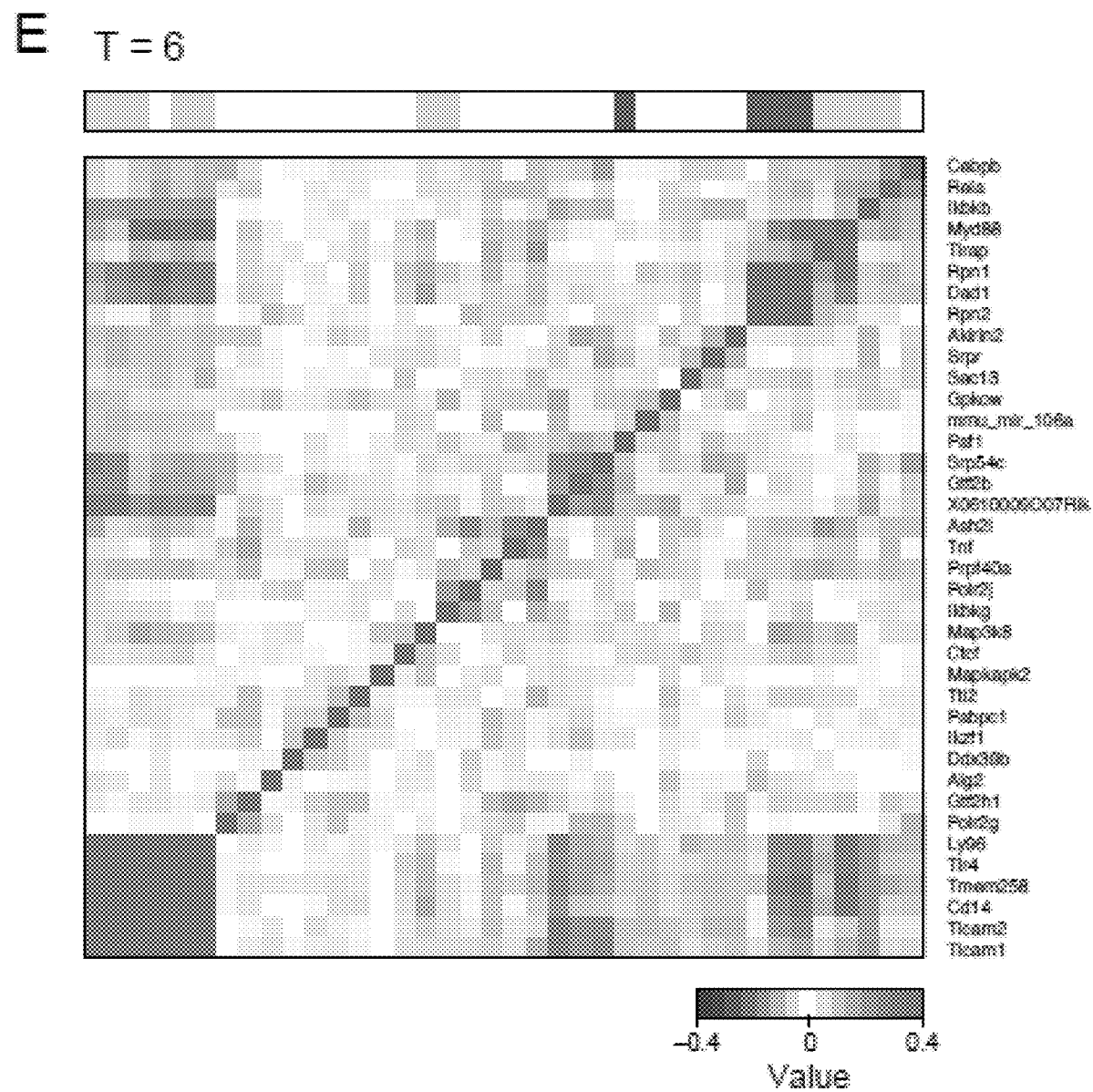

Positive Tnf regulators are organized in functional modules by their impact on RNA and protein expression While all the validated regulators affect Tnf levels, the pathways and mechanisms through which they act may be distinct. To help determine those, Applicants first measured the impact of the validated positive regulators on the expression of four additional protein markers at 8 hours post-LPS (Experimental Procedures), each reflecting distinct facets of BMDCs biology: Cd11c (the defining surface marker of BMDCs), Cd14 (a Tlr4 co-receptor), Mip1α (an induced chemokine), and Il6 (an induced inflammatory cytokine). For each sgRNA, Applicants assessed with a statistical test its effect on each protein's expression compared to a set of 6-8 non-targeting controls (Experimental Procedures), and then grouped genes based on the similarity of their effects (FIGS. 20A,B, and Table S14). Only genes where all the tested individual guides showed a similar phenotype (FIG. 25A, Experimental Procedures) were considered.

Figure 20B:
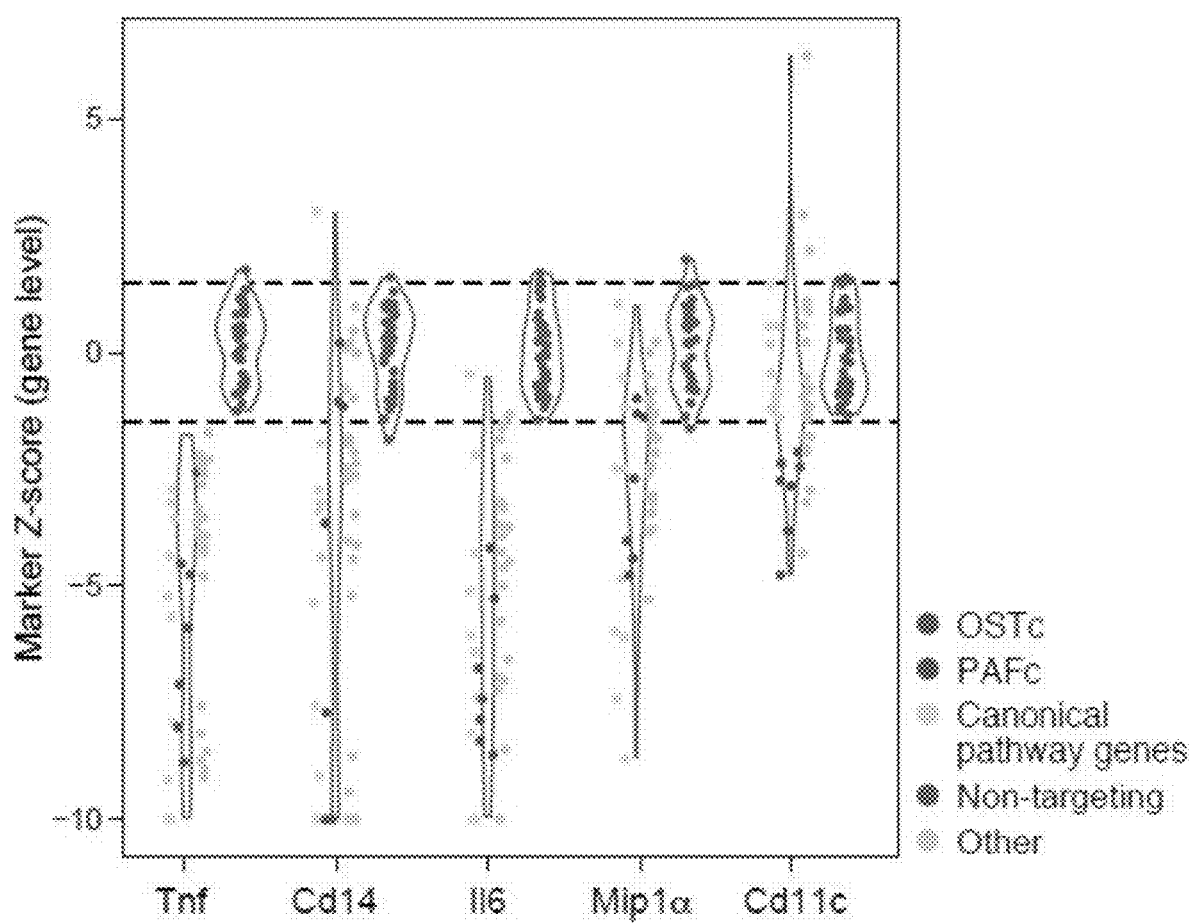
Figure 20C:
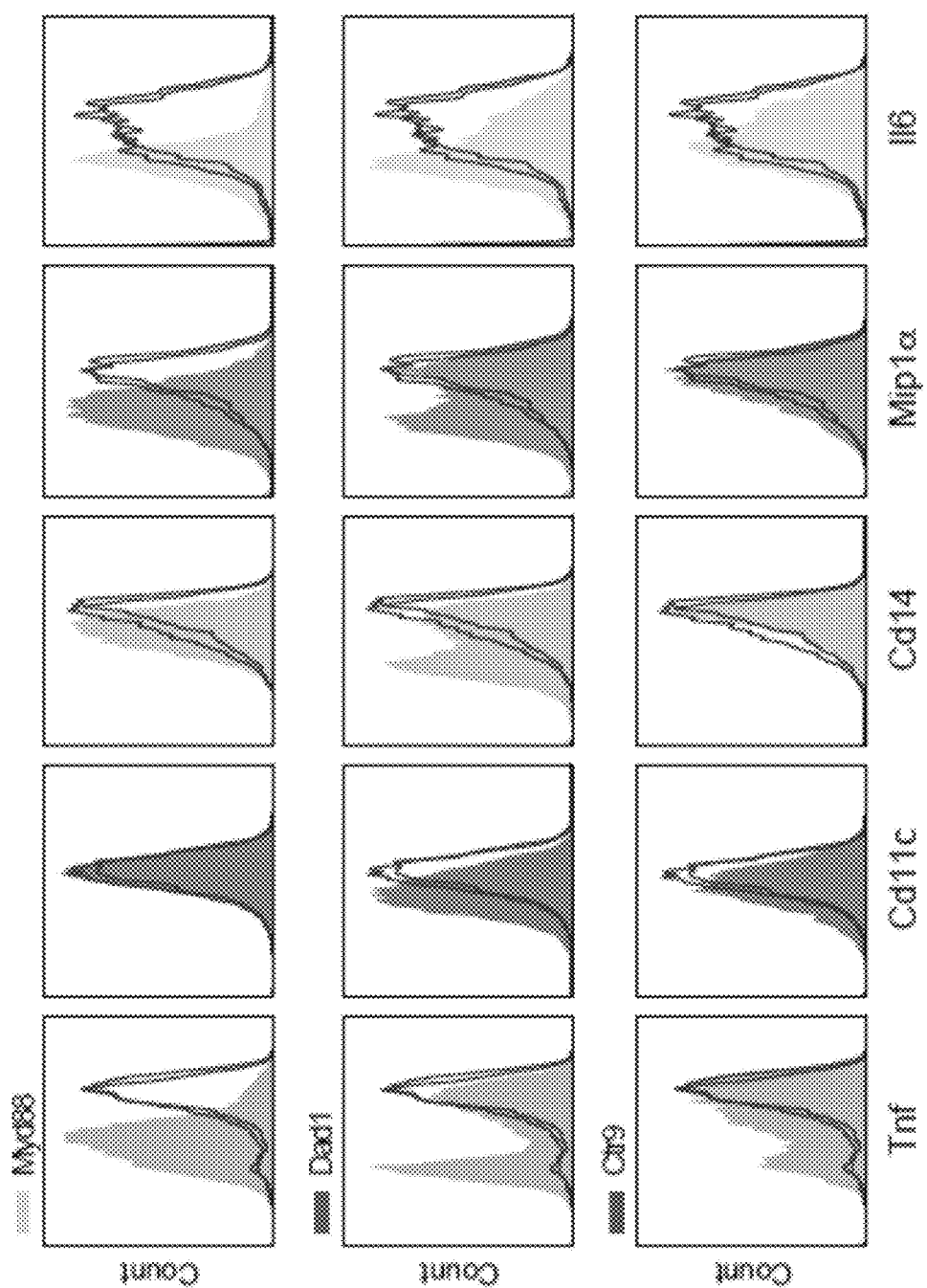
Figures 20D, 20E, 20F:
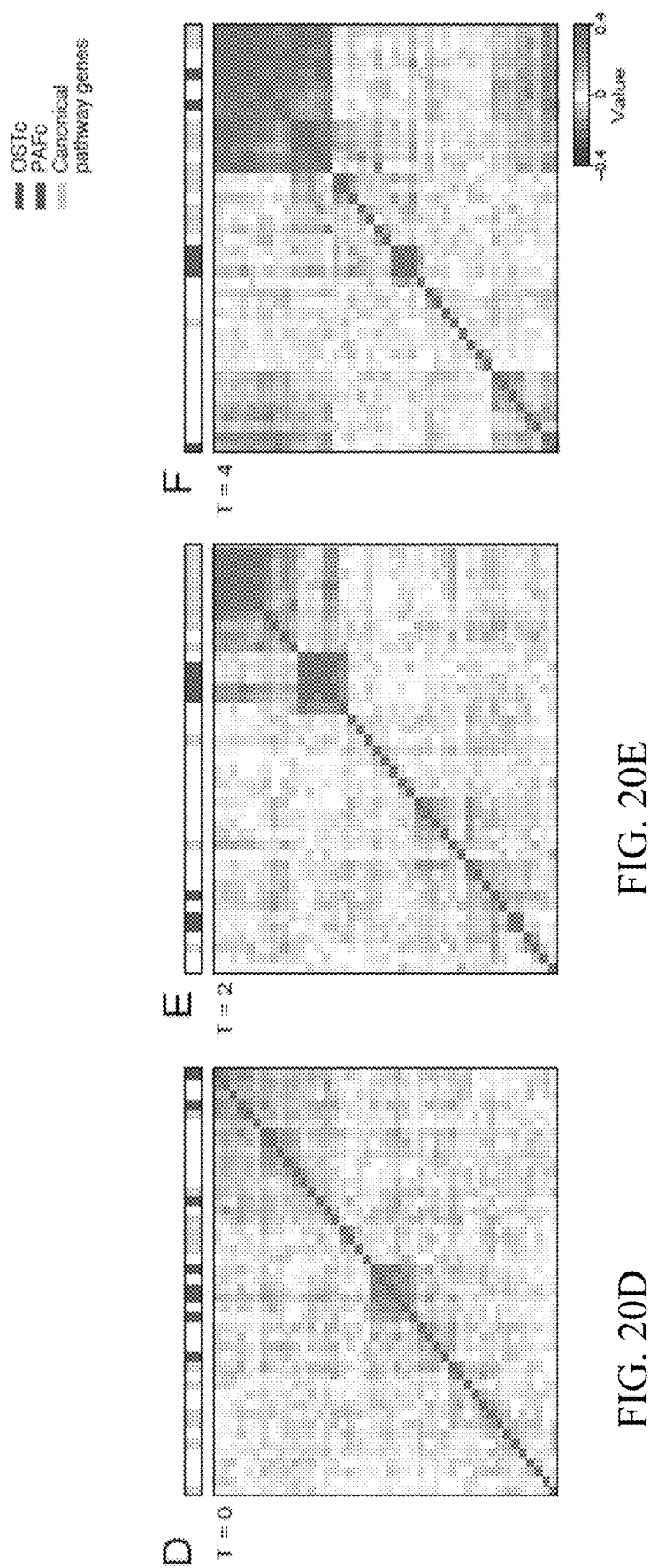

The genes are largely partitioned into several major modules (FIG. 20A), each with a distinct impact on the 4 markers, and often including multiple genes with related molecular functions. Module I consisted of sgRNAs targeting 17 genes, including 12 known regulators validated in the screen (Cd14, Ly96, Cebpb, Ikbkb, Ikbkg, Myd88, Ticam1, Ticam2, Traf2, Traf3), each reducing the levels of Cd14 and Il6, but not Cd11c (FIGS. 20A-C and Table S14). This is consistent with the known regulators' specific role in activating LPS signaling. Several additional module members were found (FIG. 20A) including Ctcf, previously implicated in DC differentiation, activation (Koesters et al., 2007), and Tnf (Nikolic et al., 2014) expression, but reported to have no effect on Il6, contrary to the observation (Table S14); and the miRNA gene, mmu-mir-106a (rank 77 DE, rank 648 ZS) not previously implicated in pro-inflammatory pathways. Module II included nine genes that each reduced the levels of all four proteins (FIG. 20A and Table S14). Among these were multiple subunits of the OST protein glycosylation complex (see below) and Alg2, a glycosyl-transferase involved in oligosaccharide synthesis (Haeuptle and Hennet, 2009; Huffaker and Robbins, 1983), as well as genes whose molecular function is currently unknown, such as Tmem-258 (FIG. 20A). Additional genes showed diverse patterns. For example, four genes Gtf2b, Rbck1, Gtf2h1, and Polr2j, only reduced the levels of TNF and IL-6. Module III consisted of sgRNAs targeting 4 regulators, each reducing Cd1 1c, and 116 expression, but had a very minor, albeit consistent, effect on Mip1α (FIG. 20B,C) and no effect on CD14. Among these were members of the PAF complex (below), as well as Polr2g (FIGS. 20A-C and Table S14), the only transcriptional and splicing regulator (among 6 Applicants tested here; Table S2) with this phenotype. PAFc and Pol2 are known to physically and functionally interact (Wade et al., 1996).

These findings suggests that regulators in each of the Modules I-III may affect Tnf levels through mechanisms that are shared by members of the same module, but distinct from those of the other modules. However, measuring only select protein markers, many of which are expressed only by a relatively late time point, limits the ability to distinguish these pathways. Applicants hypothesized that measuring the effect on global mRNA expression, at early time points, would allow us to further refine and elaborate these pathways.

Applicants therefore next measured the global effect of each regulator on mRNA levels at 0,2,4 and 6 hours post-LPS using RNA-Seq (Experimental Procedures). Applicants assessed the effect of each sgRNA on the level of each mRNA at each time point by comparing it to a set of 12-14 non-targeting guides per time point as controls with a statistical test, and then combined these sgRNA scores into a gene-level score, and correlated the regulators by their global effect (FIGS. 20D-F and FIGS. 25B-E, Experimental Procedures).

Applicants found that the regulator modules change over time—with the distinctions sharpened earlier in the response, and diminishing at later time points, as they converge through likely indirect effects. At time zero (pre-LPS, FIG. 20D), most regulators form a single module with little effect compared to non-targeting controls, except for one group of regulators with a distinct phenotype. This distinct module consists almost entirely of members of the OST complex, and also includes Alg2, functionally related to the OST complex (below) and Tmem258, a protein with unknown function. At time points 2 and 4 hours (FIGS. 20E,F), the regulators partition to several additional modules—including the known TLR regulators, a PAF complex module, and a module associated with RNA regulators including Akirin2, Polr2g and Pabpc1. Perturbation of the genes in the latter module reduces (p-value <0.001) the expression of genes involved in immune effector processes, and regulation of immune system process (GOrrila qFDR 0.0377 and 0.0246 at t=2 h Table S15). These are similar to the classification by the 4 protein markers, consistent with the prior observation that RNA regulation peaks ~4 hours prior to protein regulation in this system (Jovanovic et al., 2015). Finally, by 6 hours (FIG. 25E), the transcriptional effect of most regulators is more similar. Profiles were typically collected without Brefeldin (since it is not necessary for mRNA measurements). Comparing profiles collected with or without Brefeldin treatment, its effect was limited primarily to the antiviral module (FIG. 31), as expected (Shalek et al., 2014).

Figure 29:
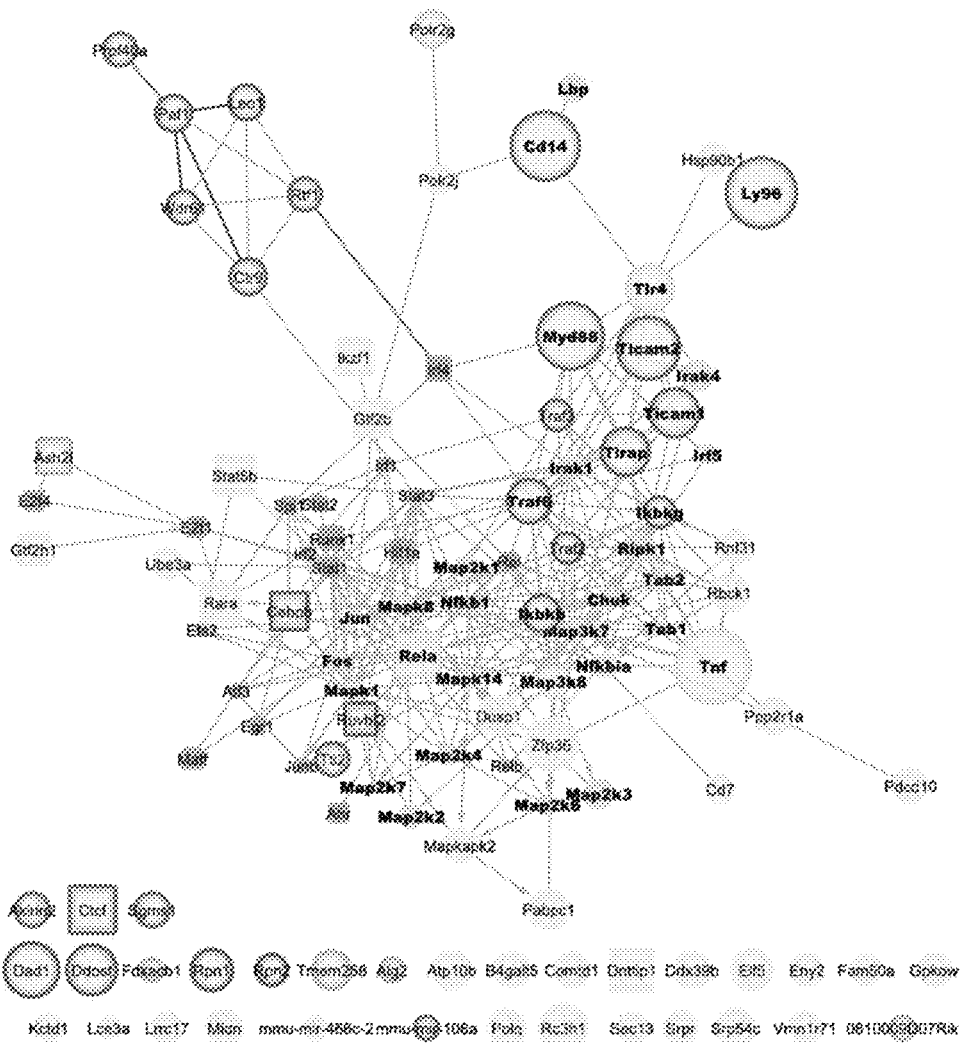
FIG. 29 A protein interaction map associating known regulators and validated all the validated positive and negative regulators from the screen. Applicants attempted to directly connect 75 Tnf regulators (57 positive and 18 negative) found in this study (beige nodes) to 35 known members of LPS-TLR4 pathway (boldfaced labels) and 23 relevant transcription factors (red nodes and Cebpb, Rela, and Nfkb1) previously identified (see Experimental procedure). Applicants used information from protein-protein interaction databases and AP-MS data collected in this study. The members of modules identified in various screens (see FIG. 3A) are marked by node rim colors as follows: PAF complex known members (dark blue) and other module members (light blue); OST complex (dark and light purple); LPS-TLR4 module members (dark green). Node sizes are linearly proportional to the absolute values of scores in the primary TNF screen. Rounded square nodes indicate transcription factors. Red edges indicate interactions found in the AP-MS experiment (bright red—novel, dark red—confirming).
Figure 30A:
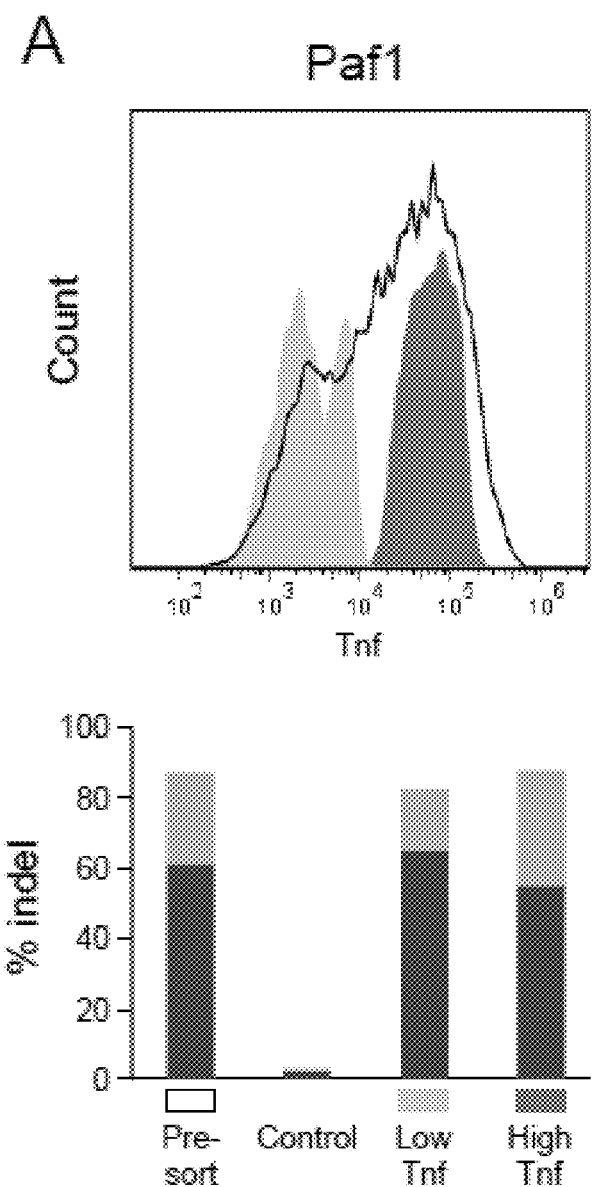
Figure 30B:
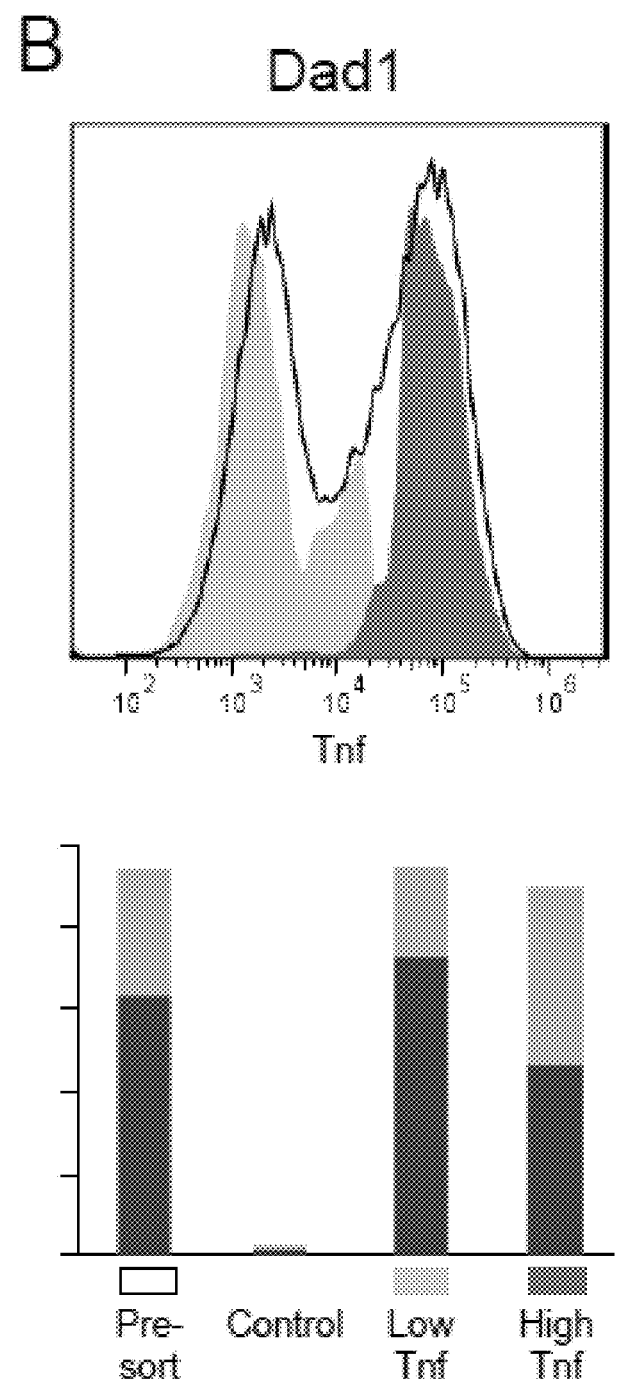

The modules are further supported by their organization in the context of the known LPS/TLR4 circuit and overall protein interaction network (FIG. 29). For example, the PAFc module is supported by known interactions and putatively connected to the core network through physical interactions with key TFs in the response. In other cases, individual factors "hit" in the screen are placed in context of known parts of the network, suggesting the basis for their impact. Nevertheless, little is known about how several of the validated regulators (e.g., members of the OSTc) are connected to the canonical pathway and thus they may suggest the involvement of additional parts of the molecular circuitry, as Applicants explored next.

Taken together, the data suggests up to four modules that impact Tnf levels in distinct ways: the key TLR signaling pathway, the effects of two complexes: OST and PAF and possibly associated processes, and the function of diverse RNA regulatory proteins. Applicants next explored these functions, focusing on the modules of the OST and PAF complexes.

Figures 21A, 21B, 21C, 21D, 21E:
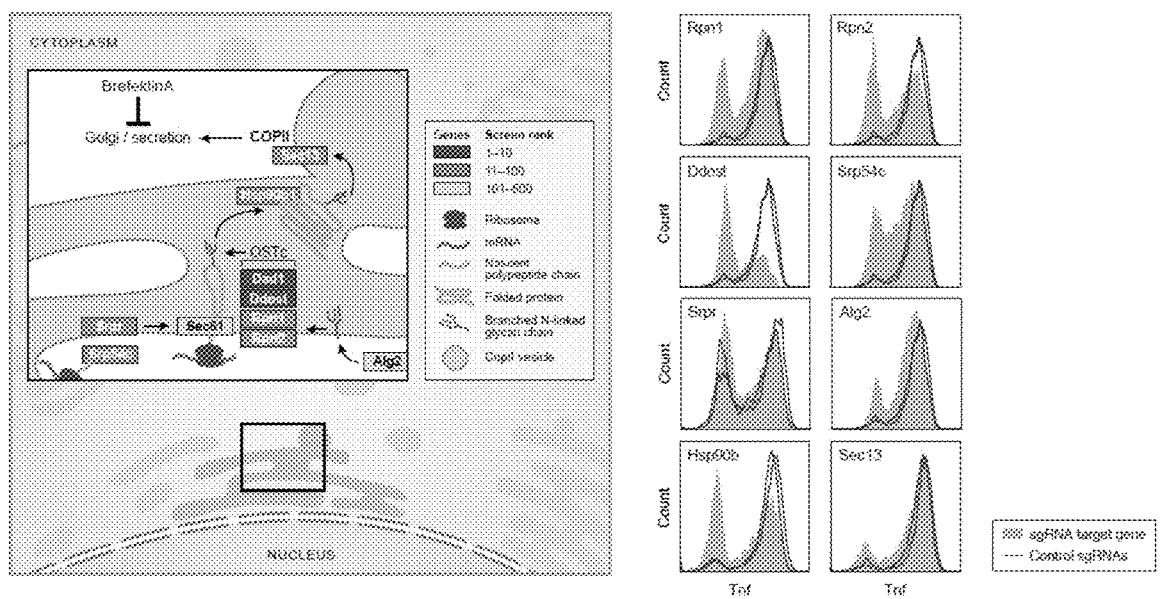
FIG. 21A-E The OST complex strongly affects the BMDC inflammatory response. (A) Positive regulators in the context of the secretory pathway. Left: Shown are proteins (blue rectangles) from the OST complex and the secretory pathway that ranked high in the genome wide CRISPR screen. Right: Flow cytometry staining of intracellular Tnf for each targeted gene (blue) compared to sgRNA controls (black). (B-E) Specific impact of OSTc perturbation on inflammatory gene expression at (B) basal state (t=0 h); (C) 2 hours post LPS; (D) 4 hours post LPS. Shown are heatmaps of all mRNAs (rows) that are differentially expressed (in at least one time point; adjusted p-value <0.001) between cells infected with non-targeting control sgRNAs (grey) and either cells where OSTc components were perturbed (purple columns) or cells where other canonical Tlr pathway genes (green) were perturbed. The genes are shown in the same order in all panels, and marked on left for their membership in the anti-viral module (orange), peaked inflammatory module and sustained inflammatory module (green) and ER-stress response module (green). Prior to stimulation (B), knockout of OSTc members induces a cluster of genes enriched for the 'unfolded protein response'; upon LPS stimulation (C-E), there is a reduction in the inflammatory response. Heatmap elements are colored by their row normalized Z-scores relative to non-targeting controls (color bar).

Components of the OST complex and the ER folding and translocation pathway are important for Tnf expression in response to LPS sensing Four of the nine structural subunits of the oligosaccharyltransferase complex (OSTc) are among the top 100 ranked positive regulators: Dad1, Ddost/OST48, Rpn1, and Rpn2 in ranks 6 7, 14 and 73, respectively, with each validated individually (FIG. 20C and FIG. 21), and all four are members of the same module by both protein (FIG. 20A) and RNA-Seq (FIG. 20D-F) analysis. Each of these 4 hits is an essential subunit for OSTc activity, while the remaining 5 known subunits appear to confer substrate selectivity (Mohorko et al., 2014), with some functional redundancy among 4 of these 5 (Aebi, 2013) (also scoring much lower, ranks 304-7,677 in the screen).

The ER-resident OSTc tags asparagine residues of newly-translated proteins with oligosaccharide chains that are critical for protein folding and transport through the ER. Consistent with the identification of OSTc, many other genes that are essential for the ER transport pathway (upstream or downstream of OSTc) were also among the top-ranking validated positive regulators (although not necessarily the OSTc module), including: (1) Srp54c (rank 17, FIG. 21A), a component of the SRP complex that interacts with the hydrophobic N terminus of the protein during protein synthesis and directs it to (2) Srpr (rank 55, FIG. 21A), a receptor on the ER membrane (Wild et al., 2004); (3) Sec61 (rank 101 DE rank and 461 ZS; not tested individually), a component of the ER channel through which proteins are translocated (Dudek et al., 2014); (4) Alg2 (rank 87 DE; 269 ZS, FIG. 21A) one of the enzymes necessary for synthesis of the oligosaccharide chain (Aebi, 2013); chaperones that help fold the protein after N-glycosylation, especially (5) Hsp90b (rank 63, FIG. 21A): and (6) Sec13 (rank 86, FIG. 21A), a structural component of COPII-coated vesicles that form after a protein is properly folded (Salama et al., 1997). Thus, ~16% (9/57) of the verified hits in the screen are known to affect protein translocation and folding that are critical for the secretory process, and six of them are in the "OSTc module" in the RNA-Seq and/or protein analysis.

Over 2,300 proteins are known to be N-glycosylated (Zielinska et al., 2010) and knocking out subunits of OSTc may affect Tnf levels directly or indirectly, and—in either case—could reflect a more global effect on N-glycosylated proteins and cell phenotype in LPS-stimulated BMDCs (Notably, there are no discernable differences in viability in the OSTc targeted cells pre-LPS). In particular, both LY96 and Tlr4 are N-glycosylated, and Tlr4 transport to the membrane is disrupted in the absence of tagged asparagines (da Silva Correia and Ulevitch, 2002). Furthermore, HSP90b (above) was shown to be important for Tlr4 folding and trafficking, with Tnf levels reduced in response to LPS in HSP90b-null macrophages (Lee et al., 2013; Randow and Seed, 2001; Yang et al., 2007). Thus, Applicants hypothesized that OSTc (and additional components of the broader pathway, such as Alg2) could affect Tnf levels by impacting Tlr4 and/or its signaling.

Supporting this hypothesis, targeting any of the four OSTc structural subunits or Alg2 (FIG. 20C and FIG. 26A) strongly reduces each of the four protein markers (FIG. 20A), including CD11c. This general reduction is consistent with either of two hypotheses: (1) the cells are not properly differentiated; or (2) the cells have differentiated properly but their sensing or response to LPS is compromised. In the latter case, OSTc mutants could have either (2a) a global signaling defect (e.g., due to a lack of key receptors on the membrane) or (2b) a more specific regulatory effect.

To distinguish between these hypotheses, Applicants examined the specific genes whose expression is affected in OSTc-targeted cells, compared to cells targeted by known regulators from the TLR pathway (which do not affect Cd11c expression), or in cells with non-targeting sgRNA controls, either before or after LPS stimulation (FIG. 21B-E, Experimental Procedures). Applicants reasoned that a global differentiation defect would be apparent in global gene expression profiles pre-LPS, whereas a global LPS signaling defect would be apparent post-LPS as a broad change in gene expression, while a specific regulatory effect would be manifested as a unique transcriptional signature.

Pre-LPS (FIG. 21B), while there are few transcriptional differences between cells where OSTc is targeted or not (Table S16), there is a group of 60 OST-induced genes that are enriched for genes in the ER stress response (FDR q-value=$5.83 \times 10^{-16}$, GOrrila). Furthermore, 42 of 60 (p value $<P<10^{-10}$, Hypergeometric test) of these genes are bound by the transcription factor XBP1 at their proximal promoter in bone marrow derived macrophages (Maxim Artyomov, Laurie Glimcher, and AR, unpublished results). Thus, OSTc perturbation has a limited and unique pre-LPS effect on ER stress response genes, likely mediated by XBP1, and the reduction in CD11c appears to reflect a secretory but not a differentiation defect (see Discussion).

Conversely, after LPS stimulation, sgRNAs targeting OSTc led to a reduction in LPS-responsive genes (FIG. 21B-E), especially the inflammatory response (FIG. 22D,E), including the Tnf mRNA (P=0.007; t-test FIG. 22F). In particular, the LPS response in DCs has been previously characterized (Shalek et al., 2014) by three distinct co-expression modules: (1) anti-viral genes ('Anti-viral'), (2) inflammatory genes, including Tnf, whose expression peaks at 2 h ('Peaked Inflammatory'); and (3) inflammatory genes with sustained expression within the 6 h time scale ('Sustained Inflammatory'). While mutants in known TLR genes are defective in activating all three modules (FIG. 22C-E), targeting OSTc members reduces the inflammatory modules (sustained: P=0.01; peaked: P=0.01, T=4 h t-test), but not the anti-viral module (P=0.24 t-test) (FIGS. 21B-E and FIGS. 22C-E), suggesting a specific rather than global effect on the TLR4 response.

Figure 26:
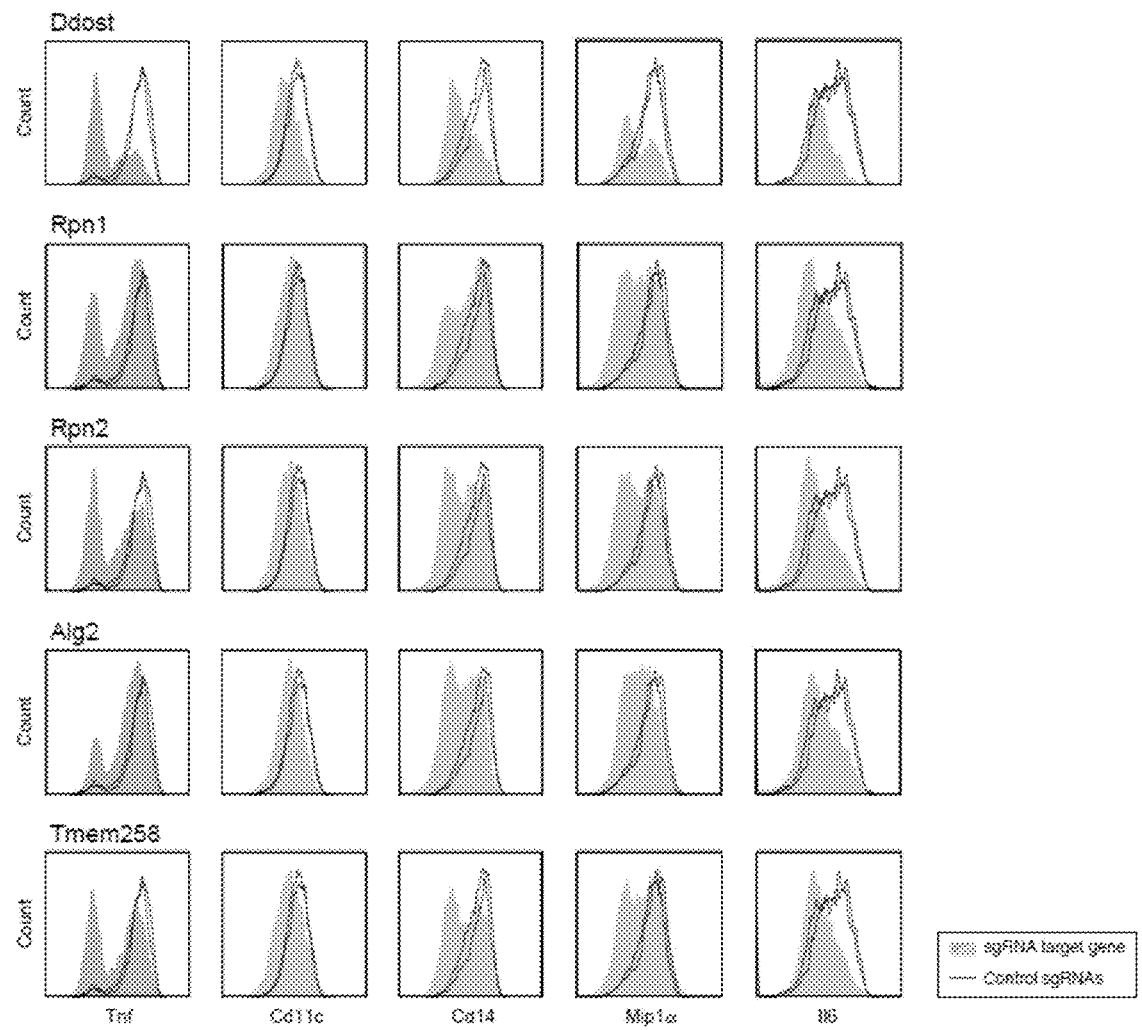
FIG. 26 Knockout of members of the OSTc module reduces the expression of five key protein markers. Each panel shows flow cytometry staining of the levels (X axis) of each of five protein markers (from left to right: Tnf, Cd11c, Cd14, Mip1α, Il6) in cells with individual sgRNA targeting specific genes (colored histogram; gene name in top left corner) compared to sgRNA controls (black curves). Data is shown (from top to bottom) for three representative members of OSTc (Ddost, Rpn1, Rpn2), and two other members of the module: Alg2 and Tmem258.

Additional regulators with the same profile as OSTc may regulate Tnf through related pathways. These include Hsp90b and Alg2, both of which are known members of the protein folding and secretion pathways (above), and Tmem258 (FIG. 20C and FIG. 26). In particular, human Tmem258, a molecularly uncharacterized gene, resides in a locus associated with Crohn's disease in Genome Wide Association Studies (Franke et al., 2010) and was reported to be targeted by ANRIL, a long non coding RNA associated with immune and metabolic diseases (Bochenek et al., 2013). In the study, targeting of Tmem258 induces the same ER stress genes pre-LPS as does targeting of OSTc (5/14 genes; $7.7 \times 10^{-5}$ Q-FDR GOrrila; Table S14), and has a similar impact on the protein markers and RNA-Seq profiles post-LPS, suggesting that a similar mechanism may underlie its function.

Taken together, the finding of an ER stress response in resting DCs supports a model by which OSTc perturbation affects protein folding and stability in the secretory pathway, consistent with previous studies (Aebi, 2013). While mutations in OSTc do not substantially affect BMDC differentiation, they do impact the expression and localization of membrane or secreted proteins in the LPS pathway. Furthermore, in addition to affecting the ER stress response, OSTc regulates specific inflammatory pathways, rather than merely differentiation or the global LPS response to exert its effect on Tnf and other factors.

The PAF complex and its physical interactors form a module that positively regulates Tnf protein expression Five of six known subunits of the PAF complex (PAFc; Paf1, Ctr9, Wdr61, $Rtf_1$, and Leo1), a regulator of transcription elongation (Jaehning, 2010) and 3' mRNA processing (Jaehning, 2010), were identified as positive regulators of Tnf expression among the top-100 ranked genes in the primary screen; each was validated individually (FIG. 20C, FIG. 22A, and FIG. 27A), did not significantly affect cell proliferation (data not shown) and had a similar effect on RNA and protein expression, and associated most strongly with a single module (FIG. 20, blue). The sixth subunit, Cdc73 (rank 842 in the primary screen) was likely a false negative, since two additionally-designed sgRNAs did reduce Tnf expression (FIG. 27B). Furthermore, the Ash2l subunit of the MLL complex, previously reported to physically interact with Cdc73 (Rozenblatt-Rosen et al., 2005), was also validated as a positive regulator of Tnf in the screen (rank 41, FIG. 27B). Both PAFc and MLL can affect H3K9 methylation (Krogan et al., 2003; Steward et al., 2006; Taniue et al., 2011).

PAFc is known to interact with RNA polymerase II with roles in transcription elongation and 3' mRNA processing (Jaehning, 2010), and regulation of transcription elongation was previously shown to be an important key step in the DC transcriptional response (Beaudoin and Jaffrin, 1989; Hargreaves et al., 2009). Prior studies have implicated Paf-1 or PAFc in regulation of antiviral gene expression either as an activator (Marazzi et al., 2012) following viral infection, or as a suppressor (Fonseca et al., 2013), with (Fonseca et al., 2013) or without (Kim et al., 2013a) viral infection. Although PAFc was not previously implicated in Tnf or inflammatory gene expression, LPS is known to induce the expression of both anti-viral and pro inflammatory genes (Amit et al., 2009).

To decipher the specific impact of PAFc, Applicants examined its transcriptional effect on each of the Antiviral, Peaked Inflammatory and Sustained Inflammatory Modules. Targeting the subunits of PAFc significantly reduces the expression of genes in the Anti-Viral Module (−1.9 shift in the mean of the Z scores, FIG. 22C, P=0.0002, t-test) and Sustained Inflammatory Modules (−0.8; FIG. 22D, P=0.001), but had a weaker (−0.6), albeit significant (P=0.01), effect on the Peaked Inflammatory Module, including Tnf mRNA (P=0.004 Z score of −1.3, FIGS. 22E and F). Thus, although PAFc targeting strongly affects Tnf protein expression, and although its direct molecular function is in RNA transcription and processing, its effect on Tnf mRNA is relatively weak. These results are further supported by the fact that targeting PAFc does not affect CD14 expression, but does reduce CD11c, MIP1, and IL-6 protein expression (FIG. 20A-C), suggesting that PAFc's effects are selective. PAFc may thus act to control transcription, and perhaps indirectly affect the levels of translation or stability of Tnf and other proteins.

In order to get a better mechanistic insight into PAFc's function Applicants aimed to identify additional PAFc interactors by immunoprecipitation of Paf1 from BMDCs followed by Mass Spectrometry (MS) (FIG. 22G and Table S18). Applicants re-identified all known complex components, except $Rtf_1$, and identified interactions with several RNA processing factors, including Srsf, Xab2 (rank 18) (Kuraoka et al., 2008) and the AU rich RNA binding and leucine metabolism protein AUH (rank 242) (Kurimoto et al., 2009; Nakagawa et al., 1995), the latter also confirmed by Western blot (FIG. 27E).

Although $Rtf_1$ interacts with Paf1 in lower organisms (Mueller and Jaehning, 2002), Applicants did not observe a direct interaction between PAFc and $Rtf_1$, when immunoprecipitating on either Paf1 (FIG. 22G) or $Rtf_1$ (FIG. 22H and Table S18 and S19). Of seven $Rtf_1$ interactors (Git1, Arhgef7, Gpx1, Sf3b1, Git2, Arhgef6 and Irf4), only one, Irf4, significantly reduced Tnf expression (FIG. 22G), consistent with its ranking in the secondary screen (rank 15). While Irf4 was previously reported to suppress Tnf (Lassen et al., 2010; Lech et al., 2011), it may be that targeting Irf4 affects DC differentiation (Lehtonen et al., 2005; Tussiwand et al., 2012). Indeed, CD1 1 c is strongly reduced in day 9 BMDCs where Irf4 was targeted (FIG. 27C). Taken together, these results suggest that in BMDC $Rtf_1$ may not be a bone fide member of PAFc, but may still act through the same pathway. Furthermore, the interaction between Irf4 and $Rtf_1$ may suggest that PAFc and its accessory proteins can perform immune specific transcriptional activation by recruiting sequence-specific transcription factors.

Finally, using individual sgRNA assays for each of the putative PAFc interactors, Applicants determined that at least two additional proteins that physically interact with PAFc also regulate Tnf expression: AUH and Xab2. Targeting Auh (FIG. 22I), but not Srsf (FIG. 27D), significantly reduces Tnf levels, whereas Xab2 targeting also dramatically reduced (with two sgRNAs) the number of cells by day 9 (data not shown). AUH binds AU-rich motifs in 3'UTRs, and the stability of the Tnf transcript is known to be regulated through such an AU rich motif by three other RNA binding proteins: AUF1 (Khabar, 2010), Zfp36 (Carballo et al., 1998) and HuR (Dean et al., 2001; Tiedje et al., 2012). It would be interesting to explore if AUH also interacts with the 3'UTR of Tnf directly to regulate Tnf levels.

Example 7: Ex vivo genome editing in primary cells by lentiviral-mediated sgRNA expression The CRISPR-CAS9 screen in primary cells described herein can be used in different primary cell types, including, but not limited to macrophages and T cells. The primary cells may be immune cells, endocrine cells, nervous system cells, muscle cells, exocrine secretory epithelial cells, hormone secreting cells, or metabolism and storage cells. "Primary cells" refer to any cells that are cultured directly from a subject. Different conditions can be used, such as, activation with another pathogenic signal or in the presence of cytokines. In addition, Applicants use other markers in addition to TNF as a phenotypic readout, including, but not limited to transcription factors, cell surface molecules, secreted cytokines, and secreted hormones.

The invention is further described by the following numbered paragraphs:

1. A method for modulating leukocyte activity, comprising delivering to a leukocyte a vector containing nucleic acid molecule(s), whereby the leukocyte contains or expresses or is able to be induced to express or conditionally expresses Cas9 and the vector expresses one or more RNAs to guide the Cas9 and optionally delivers donor template(s) to introduce mutations in one or more target genetic loci in the leukocyte, thereby modulating expression of one or more genes in the leukocyte.

2. The method of any paragraph 1 wherein the RNAs to guide Cas9 comprise chimeric single guide RNA (sgRNA).

3. The method of paragraph 2, wherein each sgRNA is driven by a U6 promoter.

4. The method of any one of paragraphs 1-3, wherein the vector is a lentiviral vector.

5. The method of paragraph 4, wherein the vector is a U6-sgRNA lentiviral vector.

6. The method of any one of paragraphs 2-5, wherein the sgRNAs target one or more genes expressed in the leukocyte so as to introduce loss-of-function or gain-of-function mutations.

7. The method of any one of paragraphs 1-6 wherein the leukocyte is a mammalian leukocyte.

8. The method of paragraph 7 wherein the leukocyte is derived from a non-human transgenic animal, such as a humanized mouse, having cells that contain or express or are able to be induced to express or conditionally express Cas9, and the vector is delivered to the leukocyte ex vivo.

9. The method of paragraph 8 wherein the non-human transgenic animal having cells that contain or express or are able to be induced to express or conditionally express Cas9 is a mammal or a primate, or a rodent, or a mouse, or a rat or a rabbit, or a canine or dog, or a cow or bovine, or a sheep or ovine or a goat or a pig, or fowl or poultry, or a chicken, or a fish.

10. The method of paragraph 7 wherein the mammalian leukocyte is a mouse leukocyte.

11. The method of paragraph 10 wherein the mouse leukocyte is from a transgenic mouse having cells that contain or express or are able to be induced to express or conditionally express Cas9.

12. The method of paragraph 11, wherein the transgenic mouse having cells that contain or express or are able to be induced to express or conditionally express Cas9 comprises a mouse that has had a Cas9 transgene knocked into the Rosa26 locus.

13. The method of any of paragraphs 1 to 7, wherein the vector is delivered to the leukocyte in vivo.

14. The method of any one of paragraphs 1-13, wherein the leukocyte is a dendritic cell.

15. The method of any one of paragraphs 1-13, wherein the leukocyte is a T cell.

16. The method of any one of paragraphs 1-13, wherein the leukocyte is a hematopoietic progenitor or stem cell.

17. The method of any one of paragraphs 1-16, wherein the vector is delivered to the leukocyte using a cell-penetrating peptide (CPP).

18. A method of identifying a gene associated with a leukocyte response, comprising:
(a) delivering to a plurality of leukocytes a plurality of different vectors containing nucleic acid molecule(s), whereby the leukocytes contain or express or are able to be induced to express or conditionally express Cas9 and each vector expresses one or more RNAs (i) to guide the Cas9 and optionally delivers donor template(s) to introduce mutations in different target genetic loci or (ii) to guide the Cas9 to activate or inhibit expression of a target gene in the leukocytes, thereby modulating expression of different genes expressed in the leukocytes;

(b) measuring a response in the leukocytes; and (c) isolating leukocyte(s) in which the response is modulated following delivery of the vector, thereby identifying gene(s) or genetic elements associated with the leukocyte response.

19. The method of paragraph 18, wherein the genes or genetic elements associated with the leukocyte response are identified by sequencing one or more nucleic acid molecules present in the isolated or sorted leukocytes.

20. The method of paragraph 18 or paragraph 19, wherein the leukocyte response is activation, inhibition, exhaustion, differentiation, migration, adhesion, death or proliferation.

21. The method of paragraphs 18-20, wherein the leukocytes comprise dendritic cells and the response comprises activation.

22. The method of paragraph 21, wherein the dendritic cells are stimulated with bacterial lipopolysaccharide (LPS).

23. The method of paragraph 22, wherein the dendritic cells are stimulated with LPS in the presence of interleukin-10 (IL-10).

24. The method of any of paragraphs 21 to 23, wherein activation is measured by determining TNF-α or CD86 expression in the dendritic cells.

25. The method of any of paragraphs 18-24, wherein the RNAs to guide Cas9 comprise chimeric single guide RNA (sgRNA).

26. The method of paragraph 25, wherein each sgRNA is driven by a U6 promoter.

27. The method of any one of paragraphs 18-26, wherein the vector is a lentiviral vector.

28. The method of paragraph 27, wherein the vector is a U6-sgRNA lentiviral vector.

29. The method of any one of paragraphs 25-28, wherein the sgRNAs target one or more genes expressed in the leukocytes so as to introduce loss-of-function or gain-of-function mutations.

30. The method of any of paragraphs 18-29, wherein the vectors are delivered to the leukocytes using a cell-penetrating peptide (CPP).

31. The method of any of paragraphs 18-30, wherein a decreased response in a leukocyte is indicative that a gene mutated in the leukocyte by delivery of the vector is a positive regulator of the response.

32. The method of any of paragraphs 18-30, wherein an increased response in a leukocyte is indicative that a gene mutated in the leukocyte by delivery of the vector is a negative regulator of the response.

33. The method of any one of paragraphs 18-32 wherein the leukocytes are mammalian leukocytes.

34. The method of paragraph 33 wherein the mammalian leukocytes are mouse leukocytes.

35. The method of paragraph 34 wherein the mouse leukocytes are from a transgenic mouse having cells that contain or express or are able to be induced to express or conditionally express Cas9.

36. The method of paragraph 35, wherein the transgenic mouse having cells that contain or express or are able to be induced to express or conditionally express Cas9 comprises a mouse that has had a Cas9 transgene knocked into the Rosa26 locus.

37. The method of paragraph 35, wherein the transgenic mouse having cells that contain or express or are able to be induced to express or conditionally express Cas9 comprises a mouse that has had a Cas9 transgene knocked into CRISPRa.

38. The method of paragraph 35, wherein the transgenic mouse having cells that contain or express or are able to be induced to express or conditionally express Cas9 comprises a mouse that has had a Cas9 transgene knocked into CRISPRi.

39. The method of any of paragraphs 18-20 or 25-38, wherein the leukocytes comprise T cells and the response comprises differentiation, exhaustion, activation, or inhibition.

40. The method of paragraph 39, wherein the T cells are stimulated with interleukin-12 and the response comprises differentiation to a Th1 phenotype.

41. The method of paragraph 39, wherein the T cells are stimulated with interleukin-4 and the response comprises differentiation to a Th2 phenotype.

42. The method of paragraph 39, wherein the T cells are stimulated with TGF-β and the response comprises differentiation to a Treg phenotype.

43. The method of paragraph 39, wherein the T cells are stimulated with TGF-β and interleukin-6 and the response comprises differentiation to a Th17 phenotype.

44. The method of any one of paragraphs 39 to 43, wherein the T cells are from a transgenic mouse having cells that express Cas9 and an ovalbumin-specific αβ-T cell receptor.

45. The method of any one of paragraphs 18 to 44, wherein a library of vectors are delivered to the leukocytes, each vector in the library expressing one or more RNAs targeted to a gene in a genome of the leukocytes, and wherein the library comprises at least one vector expressing an RNA targeted to each gene in the genome of the leukocytes.

46. The method of paragraph 45, wherein the library comprises vectors expressing two, three, four, five or six or more RNAs targeted to each gene in the genome of the leukocytes.

47. The method of any one of paragraph 18 to 46, wherein the one or more RNAs guide the Cas9 to activate or inhibit expression of a target gene, and the Cas9 is a mutant Cas9 lacking nuclease activity fused to a functional domain that activates or inhibits gene expression.

48. A method for modeling an aberrant leukocyte response or a disease associated with leukocytes, comprising delivering to leukocytes a vector containing nucleic acid molecule(s), whereby the leukocytes contain or express or are able to be induced to express or conditionally express Cas9 and the vector expresses one or more RNAs (i) to guide the Cas9 to introduce mutations in one or more target genetic loci or (ii) to guide the Cas9 to activate or inhibit expression of a target gene in the leukocytes, thereby modulating expression of one or more genes expressed in the leukocytes, and wherein expression of the one or more genes is associated with the response or disease.

49. The method of paragraph 48, wherein the leukocytes are derived from a non-human transgenic animal having cells that contain or express or are able to be induced to express or conditionally express Cas9, and the vector is delivered to the leukocyte ex vivo.

50. The method of paragraph 49, wherein the transgenic non-human animal is a transgenic mouse having cells that contain or express or are able to be induced to express or conditionally express Cas9.

51. The method of paragraph 50, wherein the transgenic mouse having cells that contain or express or are able to be induced to express or conditionally express Cas9 comprises a mouse that has had a Cas9 transgene knocked into the Rosa26 locus.

52. The method of paragraph 50, wherein the transgenic mouse having cells that contain or express or are able to be induced to express or conditionally express Cas9 comprises a mouse that has had a Cas9 transgene knocked into CRISPRa.

53. The method of paragraph 50, wherein the transgenic mouse having cells that contain or express or are able to be induced to express or conditionally express Cas9 comprises a mouse that has had a Cas9 transgene knocked into CRISPRi.

54. The method of any one of paragraphs 48-53, wherein the aberrant leukocyte response is deficient or excess activation, inhibition, exhaustion, migration, adhesion, differentiation or proliferation.

55. The method of any one of paragraphs 48-54, wherein the disease is an immune system disorder.

56. The method of any one of paragraphs 48-54, wherein the disease is cancer.

57. An individualized or personalized treatment of a leukocyte-associated disease in a subject in need of such treatment comprising:

(a) delivering to leukocytes ex vivo a vector containing nucleic acid molecule(s), whereby the leukocytes contain or express or are able to be induced to express or conditionally express Cas9 and the vector expresses one or more RNAs (i) to guide the Cas9 and optionally delivers one or more donor template(s) to introduce mutations in one or more target genetic loci or (ii) to guide the Cas9 to activate or inhibit expression of a target gene in the leukocytes, thereby modulating expression of one or more genes in the leukocytes;

(b) testing treatment(s) for the disease on the leukocytes to which the vector has been delivered; and (c) treating the subject based on results from the testing of treatment(s) of step (b).

58. The method of paragraph 57, wherein the leukocytes are derived from a non-human transgenic animal having cells that contain or express or are able to be induced to express or conditionally express Cas9, and the vector is delivered to the leukocyte ex vivo.

59. The method of paragraph 57 or paragraph 58, wherein the disease is an immune system disorder.

60. The method of any one of paragraphs 57-58, wherein the disease is cancer.

61. An isolated leukocyte comprising a vector containing a nucleic acid molecule(s), wherein the leukocyte contains or expresses or is able to be induced to express or conditionally express Cas9 and the vector encodes one or more RNAs capable of (i) guiding the Cas9 and optionally delivering one or more donor template(s) to introduce mutations in one or more target genetic loci or (ii) guiding the Cas9 to activate or inhibit expression of a target gene in the leukocyte, and thereby modulating expression of one or more genes in the leukocyte.

62. An isolated leukocyte comprising a vector containing a nucleic acid molecule(s), wherein the leukocyte contains or expresses or is able to be induced to express or conditionally express Cas9, (i) one or more target genetic loci in the leukocyte comprise mutations derived from Cas9 activity guided by one or more RNAs encoded by the vector or (ii) expression of one or more target genes in the leukocytes is activated or inhibited by Cas9 guided by one or more RNAs encoded by the vector, and wherein expression of one or more genes in the leukocyte is modulated thereby.

63. The isolated leukocyte of paragraph 61 or paragraph 62, wherein the RNAs to guide Cas9 comprise chimeric single guide RNA (sgRNA).

64. The isolated leukocyte of paragraph 63, wherein each sgRNA is driven by a U6 promoter.

65. The isolated leukocyte of any one of paragraphs 61 to 64, wherein the vector is a lentiviral vector.

66. The isolated leukocyte of paragraph 65, wherein the vector is a U6-sgRNA lentiviral vector.

67. The isolated leukocyte of any one of paragraphs 63-66, wherein the sgRNAs target one or more genes expressed in the leukocyte so as to introduce loss-of-function or gain-of-function mutations.

68. The isolated leukocyte of any one of paragraphs 61-67 wherein the leukocyte is a mammalian leukocyte.

69. The isolated leukocyte of paragraph 68, wherein the leukocyte is derived from a non-human transgenic animal having cells that contain or express or are able to be induced to express or conditionally express Cas9.

70. The isolated leukocyte of paragraph 69, wherein the non-human transgenic animal having cells that contain or express or are able to be induced to express or conditionally express Cas9 is a mammal or a primate, or a rodent, or a mouse, or a rat or a rabbit, or a canine or dog, or a cow or bovine, or a sheep or ovine or a goat or a pig, or fowl or poultry, or a chicken, or a fish.

71. The isolated leukocyte of paragraph 68, wherein the mammalian leukocyte is a mouse leukocyte.

72. The isolated leukocyte of paragraph 71, wherein the mouse leukocyte is from a transgenic mouse having cells that contain or express or are able to be induced to express or conditionally express Cas9.

73. The isolated leukocyte of paragraph 72, wherein the transgenic mouse having cells that contain or express or are able to be induced to express or conditionally express Cas9 comprises a mouse that has had a Cas9 transgene knocked into the Rosa26 locus.

74. The isolated leukocyte of paragraph 72, wherein the transgenic mouse having cells that contain or express or are able to be induced to express or conditionally express Cas9 comprises a mouse that has had a Cas9 transgene knocked into CRISPRa.

75. The isolated leukocyte of paragraph 72, wherein the transgenic mouse having cells that contain or express or are able to be induced to express or conditionally express Cas9 comprises a mouse that has had a Cas9 transgene knocked into CRISPRi.

76. The isolated leukocyte of any one of paragraphs 61-75, wherein the leukocyte is a dendritic cell.

77. The isolated leukocyte of any one of paragraphs 61-76, wherein the leukocyte is a T cell.

78. The isolated leukocyte of any one of paragraphs 61-77, wherein the one or more genes is associated with a leukocyte response or a leukocyte-associated disease.

79. A non-human transgenic eukaryote or mammal having leukocytes that express or that are able to be induced to express or that conditionally express Cas9, and one or more mutation(s) in one or more gene(s) associated with a leukocyte response or a leukocyte-associated disease.

\* \* \*

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

REFERENCES

Amit, I., Garber, M., Chevrier, N., Leite, A. P., Donner, Y., Eisenhaure, T., Guttman, M., Grenier, J. K., Li, W., Zuk, O., et al. (2009). Unbiased reconstruction of a mammalian transcriptional network mediating pathogen responses. Science (New York, N.Y.) 326, 257-263.

Bell, C. L., Vandenberghe, L. H., Bell, P., Limberis, M. P., Gao, G. P., Van Vliet, K., Agbandje-McKenna, M., and Wilson, J. M. (2011). The AAV9 receptor and its modification to improve in vivo lung gene transfer in mice. The Journal of clinical investigation 121, 2427-2435.

Chen, S., Xue, Y., Wu, X., Le, C., Bhutkar, A., Bell, E. L., Zhang, F., Langer, R., and Sharp, P. A. (2014). Global microRNA depletion suppresses tumor angiogenesis. Genes & development 28, 1054-1067.

Chevrier, N., Mertins, P., Artyomov, M. N., Shalek, A. K., Iannacone, M., Ciaccio, M. F., Gat-Viks, I., Tonti, E., DeGrace, M. M., Clauser, K. R., et al. (2011). Systematic discovery of TLR signaling components delineates viral-sensing circuits. Cell 147, 853-867.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Dull, T., Zufferey, R., Kelly, M., Mandel, R. J., Nguyen, M., Trono, D., and Naldini, L. (1998). A third-generation lentivirus vector with a conditional packaging system. Journal of virology 72, 8463-8471.

DuPage, M., Dooley, A. L., and Jacks, T. (2009). Conditional mouse lung cancer models using adenoviral or lentiviral delivery of Cre recombinase. Nature protocols 4, 1064-1072.

Frese, K. K., and Tuveson, D. A. (2007). Maximizing mouse cancer models. Nature reviews Cancer 7, 645-658.

Garber, M., Yosef, N., Goren, A., Raychowdhury, R., Thielke, A., Guttman, M., Robinson, J., Minie, B., Chevrier, N., Itzhaki, Z., et al. (2012). A high-throughput chromatin immunoprecipitation approach reveals principles of dynamic gene regulation in mammals. Molecular cell 47, 810-822.

Garraway, L. A., and Lander, E. S. (2013). Lessons from the cancer genome. Cell 153, 17-37.

Gasiunas, G., Barrangou, R., Horvath, P., and Siksnys, V. (2012). Cas9-crRNA ribonucleoprotein complex mediates specific DNA cleavage for adaptive immunity in bacteria. Proceedings of the National Academy of Sciences of the United States of America 109, E2579-2586.

Geiss et al., 2008, Direct multiplexed measurement of gene expression with color-coded probe pairs, Nat Biotechnol. 2008 March;26(3):317-25. doi: 10.1038/nbt1385. Epub 2008 Feb. 17.

Govindan, R., Ding, L., Griffith, M., Subramanian, J., Dees, N. D., Kanchi, K. L., Maher, C. A., Fulton, R., Fulton, L., Wallis, J., et al. (2012). Genomic landscape of non-small cell lung cancer in smokers and never-smokers. Cell 150, 1121-1134.

Halbert, C. L., Allen, J. M., and Miller, A. D. (2002). Efficient mouse airway transduction following recombination between AAV vectors carrying parts of a larger gene. Nature biotechnology 20, 697-701.

Herbst, R. S., Heymach, J. V., and Lippman, S. M. (2008). Lung cancer. The New England journal of medicine 359, 1367-1380.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology 31, 827-832.

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes & development 15, 3243-3248.

Ji, H., Ramsey, M. R., Hayes, D. N., Fan, C., McNamara, K., Kozlowski, P., Torrice, C., Wu, M. C., Shimamura, T., Perera, S. A., et al. (2007). LKB1 modulates lung cancer differentiation and metastasis. Nature 448, 807-810.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Johnson, L., Mercer, K., Greenbaum, D., Bronson, R. T., Crowley, D., Tuveson, D. A., and Jacks, T. (2001). Somatic activation of the K-ras oncogene causes early onset lung cancer in mice. Nature 410, 1111-1116.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Koboldt, D. C., Zhang, Q., Larson, D. E., Shen, D., McLellan, M. D., Lin, L., Miller, C. A., Mardis, E. R., Ding, L., and Wilson, R. K. (2012). VarScan 2: somatic mutation and copy number alteration discovery in cancer by exome sequencing. Genome research 22, 568-576.

Lawrence, M. S., Stojanov, P., Polak, P., Kryukov, G. V., Cibulskis, K., Sivachenko, A., Carter, S. L., Stewart, C., Mermel, C. H., Roberts, S. A., et al. (2013). Mutational heterogeneity in cancer and the search for new cancer-associated genes. Nature 499, 214-218.

Li, H., and Durbin, R. (2010). Fast and accurate long-read alignment with Burrows-Wheeler transform. Bioinformatics 26, 589-595.

Limberis, M. P., and Wilson, J. M. (2006). Adeno-associated virus serotype 9 vectors transduce murine alveolar and nasal epithelia and can be readministered. Proceedings of the National Academy of Sciences of the United States of America 103, 12993-12998.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Mitzner, W., Brown, R., and Lee, W. (2001). In vivo measurement of lung volumes in mice. Physiological genomics 4, 215-221.

Park, W. Y., Kim, M. H., Shin, D. H., Lee, J. H., Choi, K. U., Kim, J. Y., Park do, Y., Lee, C. H., and Sol, M. Y. (2012). Ciliated adenocarcinomas of the lung: a tumor of non-terminal respiratory unit origin. Modern pathology: an official journal of the United States and Canadian Academy of Pathology, Inc 25, 1265-1274.

Pylayeva-Gupta, Y., Grabocka, E., and Bar-Sagi, D. (2011). RAS oncogenes: weaving a tumorigenic web. Nature reviews Cancer 11, 761-774.

Sanjana, N. E., Shalem, O., and Zhang, F. (2014). Improved vectors and genome-wide libraries for CRISPR screening. Nature Methods 11, 783-784.

Schneider, C. A., Rasband, W. S., and Eliceiri, K. W. (2012). NIH Image to ImageJ: 25 years of image analysis. Nature methods 9, 671-675.

Shackelford, D. B., and Shaw, R. J. (2009). The LKB1-AMPK pathway: metabolism and growth control in tumour suppression. Nature reviews Cancer 9, 563-575.

Shalek, A. K., Satija, R., Adiconis, X., Gertner, R. S., Gaublomme, J. T., Raychowdhury, R., Schwartz, S., Yosef, N., Malboeuf, C., Lu, D., et al. (2013). Single-cell transcriptomics reveals bimodality in expression and splicing in immune cells. Nature 498, 236-240.

Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.

TCGA-Network (2014). Comprehensive molecular profiling of lung adenocarcinoma. Nature Published online 9 Jul. 2014.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Weinberg, R. A. (2007). The biology of cancer (New York, Garland Science).

Xue, W., Chen, S., Yin, H., Tammela, T., Papagiannakopoulos, T., Joshi, N. S., Cai, W., Yang, G., Bronson, R., Crowley, D. G., et al. (2014). CRISPR-mediated direct mutation of cancer genes in the mouse liver. Nature.

What is claimed is:

1. A method of identifying a gene(s) or genetic element(s) capable of modulating a leukocyte immune response, comprising:
(a) obtaining a plurality of leukocytes from a mouse genetically modified to contain a Cas9 transgene expression cassette integrated into the Rosa26 locus of each cell, wherein said transgene is able to express Cas9 protein or is able to be induced to express or conditionally express Cas9 protein in said leukocytes;
(b) delivering in vitro to the plurality of leukocytes a plurality of different vectors containing nucleic acid molecule(s) encoding a plurality of Cas9 RNA guide sequences (i) to guide the Cas9 to introduce mutations in different target genetic loci or (ii) to guide the Cas9 to activate or inhibit expression of target gene(s) in the leukocytes, thereby modulating expression of different genes or genetic elements expressed in the leukocytes;
(c) stimulating in vitro the plurality of leukocytes under conditions to induce an immune response;
(d) detecting one or more markers associated with the induced immune response in the leukocytes;
(e) isolating or sorting leukocyte(s) according to expression levels of the one or more markers; and
(f) identifying the RNA guide sequences from the plurality of Cas9 guides sequences delivered in (b) that are encoded for by the nucleic acid molecule(s) in the isolated or sorted leukocytes, thereby identifying gene(s) or genetic elements associated with the one or more markers.

2. The method of claim 1, wherein the genes or genetic elements are identified by sequencing one or more of the nucleic acid molecules present in the isolated or sorted leukocytes.

3. The method of claim 1, wherein the leukocyte immune response is associated with activation, inhibition, exhaustion, differentiation, migration, adhesion, death, or proliferation of the stimulated plurality of leukocytes.

4. The method of claim 1, wherein the one or more markers are selected from the group consisting of tumor necrosis factor alpha (TNF-α), CD86, interferon-γ (IFN γ), IL-4, TGFβ and IL-17.

5. The method of claim 1, wherein the one or more markers are detected by Fluorescence Activated Cell Sorting (FACS).

6. The method of claim 1, wherein the genetically modified mouse is a model as to a disease associated with leukocytes.

* * * * *

UNITED STATES PATENT AND TRADEMARK OFFICE
CERTIFICATE OF CORRECTION

| | |
|---|---|
| PATENT NO. | : 11,197,467 B2 |
| APPLICATION NO. | : 15/468652 |
| DATED | : December 14, 2021 |
| INVENTOR(S) | : Regev et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 40 days.

Signed and Sealed this
Fourth Day of April, 2023

Katherine Kelly Vidal
*Director of the United States Patent and Trademark Office*

SEQUENCE LISTING

```
<160> NUMBER OF SEQ ID NOS: 29

<210> SEQ ID NO 1
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 1
nnnnnnnnnn nnnnnnnnnn gttttgtac tctcaagatt tagaaataaa tcttgcagaa      60
gctacaaaga taaggcttca tgccgaaatc aacaccctgt cattttatgg cagggtgttt   120
tcgttattta attttt                                                   137

<210> SEQ ID NO 2
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 2
nnnnnnnnnn nnnnnnnnnn gttttgtac tctcagaaat gcagaagcta caaagataag      60
gcttcatgcc gaaatcaaca ccctgtcatt ttatggcagg gtgttttcgt tatttaattt   120
ttt                                                                 123

<210> SEQ ID NO 3
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
```

<221> NAME/KEY: modified_base
<222> LOCATION: (1)..(20)
<223> OTHER INFORMATION: a, c, t, g, unknown or other

<400> SEQUENCE: 3
nnnnnnnnnn nnnnnnnnnn gttttgtac tctcagaaat gcagaagcta caaagataag    60
gcttcatgcc gaaatcaaca ccctgtcatt ttatggcagg gtgttttttt              110

<210> SEQ ID NO 4
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 4
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 5
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 5
nnnnnnnnnn nnnnnnnnnn gttttagagc tagaaatagc aagttaaaat aaggctagtc    60
cgttatcaac ttgaaaaagt gttttttt                                      88

<210> SEQ ID NO 6
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 6
nnnnnnnnnn nnnnnnnnnn gttttagagc tagaaatagc aagttaaaat aaggctagtc    60
cgttatcatt tttttt                                                   76

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 7
gagtccgagc agaagaagaa                                                    20

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gagtcctagc aggagaagaa                                                    20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gagtctaagc agaagaagaa                                                    20

<210> SEQ ID NO 10
<211> LENGTH: 7
<212> TYPE: PRT
<213> ORGANISM: Simian virus 40

<400> SEQUENCE: 10

Pro Lys Lys Lys Arg Lys Val
1               5

<210> SEQ ID NO 11
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 11

Lys Arg Pro Ala Ala Thr Lys Lys Ala Gly Gln Ala Lys Lys Lys Lys
1               5                   10                  15

<210> SEQ ID NO 12
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 12

Pro Ala Ala Lys Arg Val Lys Leu Asp
1               5

<210> SEQ ID NO 13
<211> LENGTH: 11
<212> TYPE: PRT
<213> ORGANISM: Unknown
```

```
<220> FEATURE:
<221> NAME/KEY: source
<223> OTHER INFORMATION: /note="Description of Unknown:
      C-myc NLS sequence"

<400> SEQUENCE: 13

Arg Gln Arg Arg Asn Glu Leu Lys Arg Ser Pro
1               5                   10

<210> SEQ ID NO 14
<211> LENGTH: 38
<212> TYPE: PRT
<213> ORGANISM: Homo sapiens

<400> SEQUENCE: 14

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 15
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 15

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 16
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 16

Val Ser Arg Lys Arg Pro Arg Pro
1               5

<210> SEQ ID NO 17
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 17

Pro Pro Lys Lys Ala Arg Glu Asp
1               5
```

```
<210> SEQ ID NO 18
<211> LENGTH: 8
<212> TYPE: PRT
<213> ORGANISM: Homo sapiens

<400> SEQUENCE: 18

Pro Gln Pro Lys Lys Lys Pro Leu
1               5

<210> SEQ ID NO 19
<211> LENGTH: 12
<212> TYPE: PRT
<213> ORGANISM: Mus sp.

<400> SEQUENCE: 19

Ser Ala Leu Ile Lys Lys Lys Lys Lys Met Ala Pro
1               5                   10

<210> SEQ ID NO 20
<211> LENGTH: 5
<212> TYPE: PRT
<213> ORGANISM: Influenza virus

<400> SEQUENCE: 20

Asp Arg Leu Arg Arg
1               5

<210> SEQ ID NO 21
<211> LENGTH: 7
<212> TYPE: PRT
<213> ORGANISM: Influenza virus

<400> SEQUENCE: 21

Pro Lys Gln Lys Lys Arg Lys
1               5

<210> SEQ ID NO 22
<211> LENGTH: 10
<212> TYPE: PRT
<213> ORGANISM: Hepatitis virus

<400> SEQUENCE: 22

Arg Lys Leu Lys Lys Lys Ile Lys Lys Leu
1               5                   10

<210> SEQ ID NO 23
<211> LENGTH: 10
<212> TYPE: PRT
<213> ORGANISM: Mus sp.

<400> SEQUENCE: 23

Arg Glu Lys Lys Lys Phe Leu Lys Arg Arg
1               5                   10

<210> SEQ ID NO 24
<211> LENGTH: 20
<212> TYPE: PRT
<213> ORGANISM: Homo sapiens

<400> SEQUENCE: 24

Lys Arg Lys Gly Asp Glu Val Asp Gly Val Asp Glu Val Ala Lys Lys
1               5                   10                  15

Lys Ser Lys Lys
            20
```

```
<210> SEQ ID NO 25
<211> LENGTH: 17
<212> TYPE: PRT
<213> ORGANISM: Homo sapiens

<400> SEQUENCE: 25

Arg Lys Cys Leu Gln Ala Gly Met Asn Leu Glu Ala Arg Lys Thr Lys
1               5                   10                  15

Lys

<210> SEQ ID NO 26
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
guuuuagagc ua                                                              12

<210> SEQ ID NO 27
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
acccttggtc gcgcttaacg tgggaa                                               26

<210> SEQ ID NO 28
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
aaccatgcac cgatacacgc tggaga                                               26

<210> SEQ ID NO 29
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
cccacagttc cgagagatca tcc                                                  23
```